(12) United States Patent
Sumaru et al.

(10) Patent No.: US 11,566,093 B2
(45) Date of Patent: Jan. 31, 2023

(54) POLYMER COMPOUND AND METHOD FOR MANIPULATING CELL USING SAME

(71) Applicant: NATIONAL INSTITUTE OF ADVANCED INDUSTRIAL SCIENCE AND TECHNOLOGY, Tokyo (JP)

(72) Inventors: Kimio Sumaru, Tsukuba (JP); Toshiyuki Takagi, Tsukuba (JP); Toshiyuki Kanamori, Tsukuba (JP); Kana Morishita, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 1100 days.

(21) Appl. No.: 16/305,220

(22) PCT Filed: Jun. 8, 2017

(86) PCT No.: PCT/JP2017/021332
§ 371 (c)(1),
(2) Date: Nov. 28, 2018

(87) PCT Pub. No.: WO2017/213226
PCT Pub. Date: Dec. 14, 2017

(65) Prior Publication Data
US 2020/0317839 A1      Oct. 8, 2020

(30) Foreign Application Priority Data

Jun. 8, 2016      (JP) .............................. JP2016-114432

(51) Int. Cl.
*C08F 220/36* (2006.01)
*C08F 220/60* (2006.01)
(Continued)

(52) U.S. Cl.
CPC .......... *C08F 220/603* (2020.02); *B32B 27/08* (2013.01); *B32B 27/308* (2013.01);
(Continued)

(58) Field of Classification Search
CPC ........ C12M 23/20; C08J 3/28; C08F 220/603; C08F 220/36; C08F 220/14; C32C 27/308; C32C 27/06
See application file for complete search history.

(56) References Cited

U.S. PATENT DOCUMENTS

2012/0301942 A1    11/2012   Tamiya ..................... 435/182

FOREIGN PATENT DOCUMENTS

| JP | 05-066436 A | 3/1993 |
| JP | 2004-346161 A | 12/2004 |

(Continued)

OTHER PUBLICATIONS

/Chang et al. Photolithographic Hole-Transport Layer Derived from Electrochemical Deposition of Oligo(5-vinyl-2-nitrobenzyl triphenylamine-4-carboxylate). Chemistry of Materials 2008, 20, 18, 5816-5821 (Year: 2005).*

(Continued)

*Primary Examiner* — Sanza L. McClendon
(74) *Attorney, Agent, or Firm* — Ostrolenk Faber LLP

(57) ABSTRACT

A polymer compound is provided which is changed from a water-insoluble state to a water-soluble state by irradiation with light. The polymer compound is represented by Formula (5), where A and B are a single bond or a functional group, $R^3$, $R^4$, and $R^9$ are hydrogen or an alkyl group, and $R^6$ and $R^7$ are hydrogen, an alkyl group, or the like.

9 Claims, 33 Drawing Sheets

(51) Int. Cl.
      B32B 27/08         (2006.01)
      B32B 27/30         (2006.01)
      C08F 220/14       (2006.01)
      C08J 3/28           (2006.01)
      C12M 1/00         (2006.01)

(52) U.S. Cl.
      CPC .......... *C08F 220/14* (2013.01); *C08F 220/36* (2013.01); *C08J 3/28* (2013.01); *C12M 23/20* (2013.01)

(56) References Cited

FOREIGN PATENT DOCUMENTS

JP          2006-131852 A     5/2006
WO    WO 2007/040118 A1   4/2007
WO    WO 2018/088271 A    5/2016

OTHER PUBLICATIONS

Shinji Sugiura et al, "A Photodegradable Hydrogel Sheet For Microscale Optical Control Of Cell Adhesion and Detachment" (Oct. 28, 2012) *16th International Conference on Miniaturized Systems for Chemistry and Life Sciences.* Japan XP055263835, pp. 671-672. And p. 673.
International Search Report dated Aug. 15, 2017 in corresponding PCT International Application No. PCT/JP2017/021332.
Written Opinion dated Aug. 15, 2017 in corresponding PCT International Application No. PCT/JP2017/021332.
T. Nishi et al., Chemical and Pharmaceutical Bulletin, 33(3): 1140-1147 (1985).

\* cited by examiner

R = COOH or COOCH$_2$CH$_2$H (a)

(b)

(a)

(b)

(a)

(b)

(a)

(b)

(b)

(c)

(a)

(b)

(a)

(b)

(c)

(d)

(e)

(a)

(b) (c)

(a) pH 4.0

(b) pH 5.0

(c) pH 7.4

"光溶解" means "light dissolution".

(a)

(b)

POLYMER COMPOUND AND METHOD FOR MANIPULATING CELL USING SAME

CROSS-REFERENCE TO RELATED APPLICATIONS

The present application is a 35 U.S.C. §§ 371 national phase conversion of PCT/JP2017/021332, filed Jun. 8, 2017, which claims priority to Japanese Patent Application No. 2016-114432, filed Jun. 8, 2016, the contents of which are incorporated herein by reference. The PCT International Application was published in the Japanese language.

TECHNICAL FIELD

The present invention relates to a polymer compound of which physical properties are changed by irradiation with light, and a method for manipulating a cell using the polymer compound.

BACKGROUND ART

Application of materials of which physical properties are changed by external stimuli has been actively studied in fields such as biotechnology and medical care. As a member for a bio-device that handles cells, proteins, and the like, there is a demand for a material of which physical properties are greatly changed in a water system. In these days when utilization of human iPS-derived cells has been seriously studied and needs for individually manipulating cultured cells have rapidly increased, usefulness of a material of which physical properties can be controlled with light that enables a local action on a μm scale is immeasurable.

To date, polymer materials of which a hydration property is increased by light have been reported. However, in these polymer materials, physical properties are changed at a temperature or pH which is not suitable for cell culture or insufficient changes in physical properties are exhibited. In addition, there is a report on a polymer material which has a photoacid-generating group and exhibits large changes in optical properties. However, this polymer material does not reach a level to which its insolubility or solubility in water can be controlled by light. Furthermore, this polymer material has problems that do not permit application thereof to cellular systems, such as being accompanied with liberation of low-molecular-weight components due to light-cleavage reaction, and strong acid generation. On the other hand, materials crosslinked by light are utilized for photolithography and the like. However, most of these materials require a high-temperature heat treatment.

CITATION LIST

Non-Patent Literature

[NPL 1] T. Nishi, F. Tabusa, T. Tanaka, T. Shimizu, K. Nakagawa, Chemical and Pharmaceutical Bulletin, 1985, vol. 33, No. 3, pp. 1140 to 1147

SUMMARY OF INVENTION

Technical Problem

The present invention has been made in view of such circumstances, and an object of the present invention is to provide a polymer compound which does not require a high-temperature treatment, hardly liberates low-molecular-weight components, and is changed from a water-insoluble state to a water-soluble state by irradiation with light.

Solution to Problem

A polymer compound of the present invention has a main chain and a side chain, in which the side chain contains an aromatic ring, the aromatic ring contains a first carbon atom in which a hydrogen atom bonded thereto is substituted with a nitro group and a second carbon atom in which a hydrogen atom bonded thereto is substituted with an aldehyde group or a functional group represented by Formula (1), and the first carbon atom and the second carbon atom are adjacent in the same benzene ring.

(1)

The polymer compound of the present invention is represented by Formula (2).

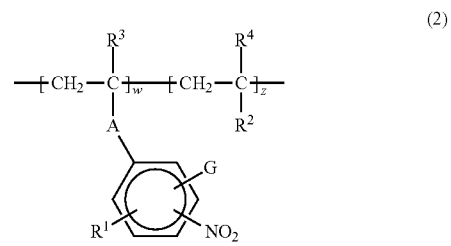
(2)

In the formula, A is a single bond or a functional group, $R^1$ is an aldehyde group or a functional group represented by Formula (1), $R^1$ and $NO_2$ are bonded to adjacent carbon atoms, $R^2$ is at least one member selected from hydrogen, an alkyl group, a functional group represented by Formula (3), and a functional group represented by Formula (4) ($R^6$ and $R^7$ are hydrogen, an alkyl group, or an aromatic ring, and $R^8$ is an alkyl group)

(3)

(4)

$R^3$ and $R^4$ are hydrogen or an alkyl group, G is 3 or less alkyl groups with which hydrogen in the benzene ring may be substituted, and w and z represent molar percentages, in which $0 < w \leq 100$ and $0 \leq z < 100$.

The polymer compound of the present invention is represented by Formula (5).

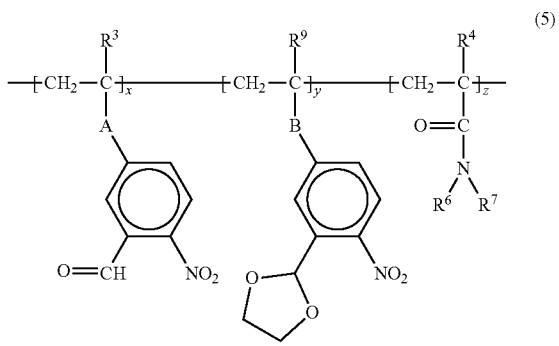

(5)

In the formula, A and B are a single bond or a functional group, $R^3$, $R^4$, and $R^9$ are hydrogen or an alkyl group, $R^6$ and $R^7$ are hydrogen, an alkyl group, or an aromatic ring, and x, y, and z represent molar percentages, in which $0 \leq x < 100$, $0 \leq y < 100$, and $0 \leq z < 100$ (where x=y=0 is excluded).

A composite material of the present invention has a base material, and a layer containing the polymer compound of the present invention provided on a surface of the base material.

A light-driven actuator of the present invention has a light source and the composite material of the present invention.

A method for manipulating a cell of the present invention has a culturing step of culturing cells on a surface of the layer containing the polymer compound in the composite material of the present invention, a light-irradiating step of causing at least a part of a region of the surface of the layer containing the polymer compound to be irradiated with light, after the culturing step, and a removing step of removing cells that exist in the region which has been irradiated with light in the light-irradiating step.

A compound of the present invention is represented by Formula (6).

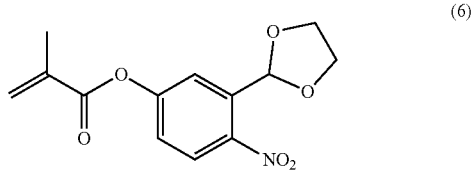 [SMILES: C=C(C)C(=O)Oc1ccc([N+](=O)[O-])c(C2OCCO2)c1]

(6)

Another compound of the present invention is represented by Formula (7).

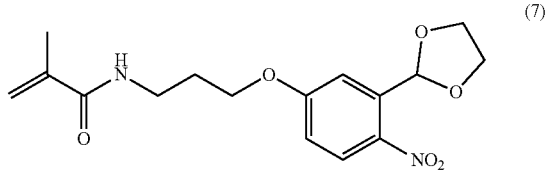 [SMILES: C=C(C)C(=O)NCCCOc1ccc([N+](=O)[O-])c(C2OCCO2)c1]

(7)

Advantageous Effects of Invention

According to the present invention, it is possible to obtain a polymer compound of which physical properties are changed, such as being changed from a water-insoluble state to a water-soluble state by irradiation with light.

BRIEF DESCRIPTION OF DRAWINGS

FIG. 20(c) is an image of the bottom surface of the composite material after irradiation with ultraviolet light.

FIG. 26 shows images showing light-responsive pH changes in a NBA copolymer aqueous solution containing BTB, in which FIG. 26(a) is an image of the aqueous solution before irradiation with light, FIG. 26(b) is an image of the aqueous solution after irradiation with light onto a lower half, and FIG. 26(c) is an image of the aqueous solution after irradiation with light onto the entire solution.

FIG. 30 shows images showing light-induced dissolution of a pNBANIPAAm solution, in which FIG. 30(a) is an image at pH 4.0, FIG. 30(b) is an image at pH 5.0, and FIG. 30(c) is an image at pH 7.4.

FIG. 33 shows images showing patterning and light-selective peeling of cultured cells using an NBA copolymer-coated film on a cell adhesion inhibition surface, in which FIG. 33(a) is an image of cultured patterns formed, FIG. 33(b) is an image during selective irradiation with light, and FIG. 33(c) is an image after spraying with a medium onto a surface.

DESCRIPTION OF EMBODIMENTS

Figure 1:
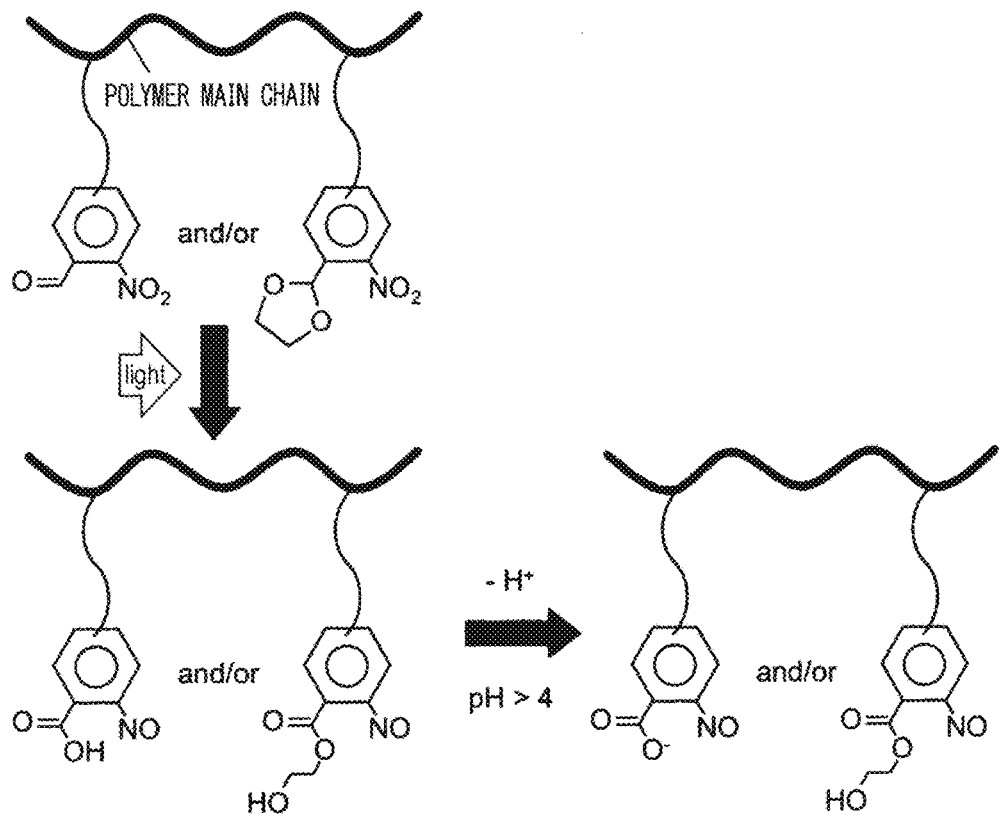
FIG. 1 is a schematic diagram showing a structural change of a polymer compound of the present embodiment.

Hereinafter, a polymer compound, a composite material, a light-driven actuator, and a method for manipulating a cell of the present invention will be described based on embodiments and examples. Redundant descriptions will be omitted as appropriate. In a case where "to" is described between two numerical values to represent a range of numerical values, these two numerical values are also included in the range of numerical values.

The polymer compound according to the embodiment of the present invention has a main chain and a side chain, in which the side chain contains an aromatic ring.

The aromatic ring contains a first carbon atom in which a hydrogen atom bonded thereto is substituted with a nitro group and a second carbon atom in which a hydrogen atom bonded thereto is substituted with an aldehyde group or a functional group represented by Formula (1). The first carbon atom and the second carbon atom are adjacent in the same benzene ring.

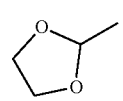

(1)

In the polymer compound of the present embodiment, solvent solubility, for example, water solubility is greatly changed by irradiation with light. For this reason, a manipulation of immobilizing an object to be manipulated, for example, a cell to a surface of a layer containing the polymer compound of the present embodiment or an manipulation of removing the object to be manipulated from the surface of the layer can be freely carried out by irradiation with light from a micrometer-scale to a macro-scale. In these days when utilization of human iPS-derived cells has been actively studied, needs for novel cell manipulation such as selection of useful cells and removal of unnecessary cells on a culture substrate are rapidly increasing. In particular, the polymer compound of the present embodiment, of which solubility in water at around neutrality can be controlled by irradiation with light, is extremely useful as a material that meets such needs.

In the polymer compound of the present embodiment, a solvent-soluble property is developed by irradiation with light. For this reason, the object to be manipulated which is immobilized to a base material via a layer containing the polymer compound can be easily removed using light and a solvent therefor. In addition, in a case where the polymer compound of the present embodiment is used, unlike a low-molecular-weight compound, it can be expected that the object to be manipulated is strongly adhered thereto due to a strong cohesive force similarly to many adhesives. The polymer compound of the present embodiment, which is changed from a water-insoluble state to a water-soluble state by irradiation with light, can be manipulated using water, so that an environmental burden is small as compared with a manipulation using an organic solvent. In addition, a material of which physical properties are changed in a water system by irradiation with light can be used for controlling a bio-system including cell culture. For this reason, it is easy to manipulate cells, such as operating cell peeling from a base material with light or patterning cells with light.

As the polymer compound of the present embodiment, a polymer compound of a random copolymer represented by Formula (2) can be mentioned.

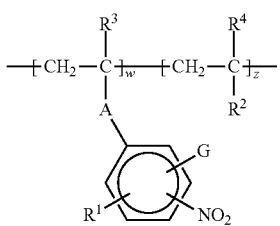
(2)

In the formula, A is a single bond or a functional group, $R^1$ is an aldehyde group or a functional group represented by Formula (1), $R^1$ and $NO_2$ are bonded to adjacent carbon atoms, $R^2$ is at least one member selected from hydrogen, an alkyl group, a functional group represented by Formula (3), and a functional group represented by Formula (4) ($R^6$ and $R^7$ are hydrogen, an alkyl group, or an aromatic ring, and $R^8$ is an alkyl group),

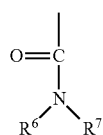
(3)

-continued

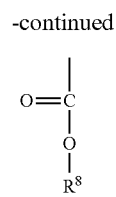
(4)

$R^3$ and $R^4$ are hydrogen or an alkyl group, G is 3 or less alkyl groups with which hydrogen in the benzene ring may be substituted, and w and z represent molar percentages in which $0<w\leq100$ and $0\leq z<100$. This polymer compound may contain other components as long as this polymer compound does not lose changes in solvent solubility due to irradiation with light.

As a more specific example of the polymer compound of the present embodiment, a polymer compound of a random copolymer represented by Formula (5) can be mentioned.

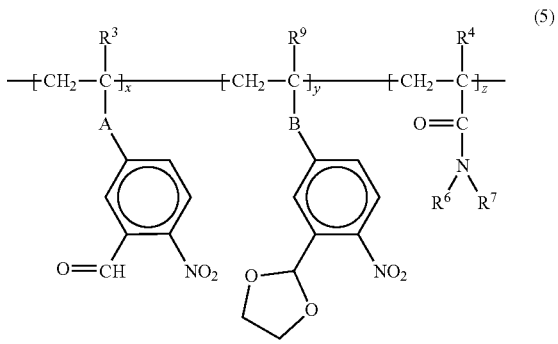
(5)

In the formula, A and B are a single bond or a functional group, $R^3$, $R^4$, and $R^9$ are hydrogen or an alkyl group, $R^6$ and $R^7$ are hydrogen, an alkyl group, or an aromatic ring, and x, y, and z represent molar percentages in which $0\leq x<100$, $0\leq y<100$, and $0\leq z<100$ (where x=y=0 is excluded). This polymer compound may contain other components as long as this polymer compound does not lose changes in solvent solubility due to irradiation with light.

Structures of A and B which connect the main chain and the benzene ring to each other are not particularly limited. As the A and B, a single bond, or a functional group including an ester bond, an ether bond, an amide bond, a thioether bond, a thioester bond, a urethane bond, or an alkylene group can be mentioned. That is, the main chain and the benzene ring may be directly bonded to each other by a single bond, may be bonded to each other via an ester bond, an ether bond, an amide bond, a thioether bond, a thioester bond, a urethane bond, or an alkylene group, or may be bonded to each other via another functional group including an ester bond, an ether bond, an amide bond, a thioether bond, a thioester bond, a urethane bond, or an alkylene group.

The polymer compound of the present embodiment can be produced by the following method. First, a polymerizable acid chloride such as methacryloyl chloride or alkyl chloride is reacted with a compound containing an aromatic ring having a hydroxyl group or amino group, to synthesize a polymerizable monomer. This compound also contains a 2-nitrobenzaldehyde (hereinafter referred to as "NBA" in some cases) site or an acetal-protected 2-nitrobenzaldehyde (hereinafter referred to as "ANBA" in some cases) site.

Next, the polymerizable monomer can be polymerized or copolymerized to obtain the polymer compound of the present embodiment.

Examples of the polymerizable monomer include a compound represented by Formula (6) or a compound represented by Formula (7). Like these compounds, it is preferable to prepare a polymer compound containing NBA or ANBA of the present embodiment by using a compound having an acetalized aldehyde group, from the viewpoint of yield and the like.

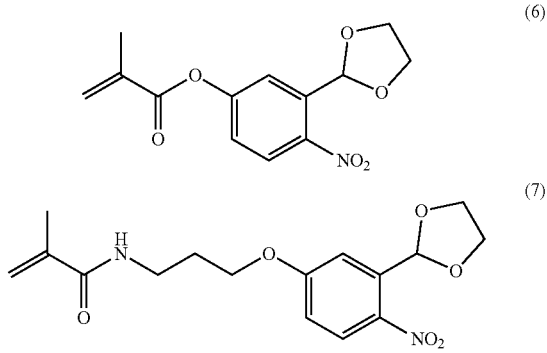

In addition, the polymer compound of the present embodiment can also be produced by reacting a reactive polymer having acid chloride or alkyl chloride, a NBA site or an ANBA site, and a compound containing an aromatic ring having a hydroxyl group or an amino group. For a compound having a hydroxyl group and NBA, a commercially available product can be used as it is. A compound having an amino group and NBA can be obtained by introducing a nitro group at an ortho position of a methyl group by nitration of commercially available p-toluidine and then converting the methyl group to an aldehyde group by oxidation. The compound having an amino group and NBA can also be obtained by reducing a carboxyl group in a state where an amino group of commercially available 5-amino-2-nitrobenzoic acid is protected by acetylation.

FIG. 1 schematically shows a structural change of the polymer compound of the present embodiment. A first carbon atom to which a nitro group is bonded and a second carbon atom to which an aldehyde group or a functional group represented by Formula (1) is bonded are adjacent in the same benzene ring. For this reason, in a case where the polymer compound of the present embodiment is irradiated with light having a wavelength of 300 nm to 410 nm in water or another solvent, as shown in FIG. 1, NBA is changed to 2-nitrosobenzoic acid having high proton dissociation capability, and ANBA is changed to a phenyl ester structure of ethylene glycol.

In a case where a pH exceeds 4, a proton dissociates from 2-nitrosobenzoic acid and the polymer compound is negatively charged. Thus, a polymer compound having a moderate hydration property such as a polymer compound obtained from an acrylamide-based monomer such as N-isopropylacrylamide, N-tert-butylacrylamide, or N,N-dimethylacrylamide, or a polymer compound obtained by (co)polymerizing a vinyl ether-based monomer is changed from a water-insoluble state to a water-soluble state by irradiation with light.

Figure 2:
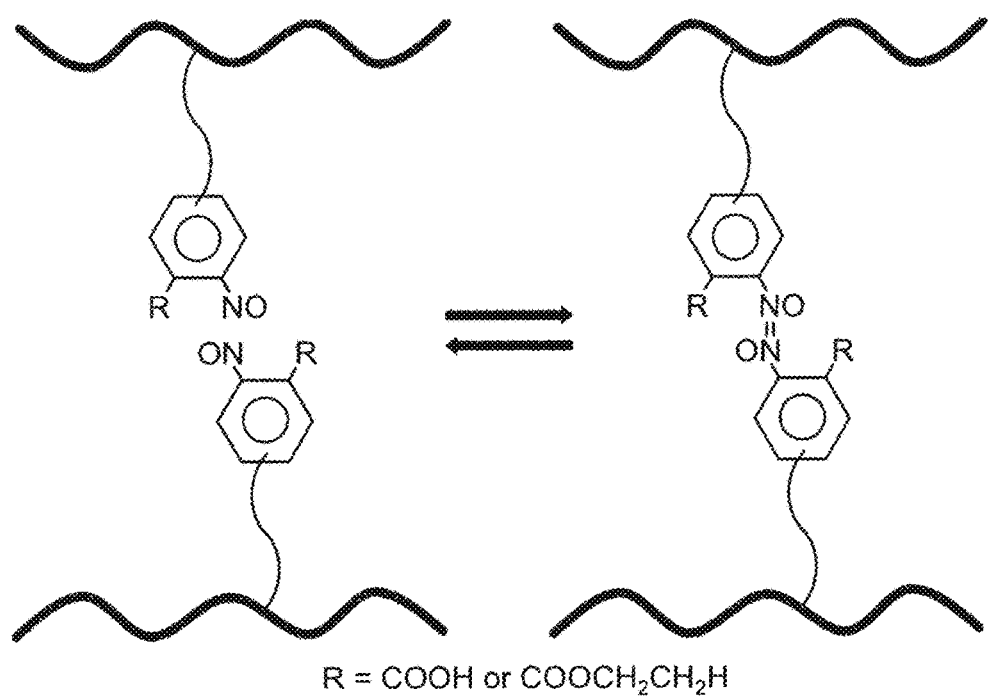
FIG. 2 is a schematic diagram showing light-responsive crosslinking of a polymer compound of the present embodiment.

FIG. 2 schematically shows light-responsive crosslinking of the polymer compound of the present embodiment. In a case where the polymer compound of the present embodiment is irradiated with light in a solid phase state such as in the air or a poor solvent, as shown in FIG. 2, crosslinking between polymers is brought about due to equilibrium dimerization or the like of a nitroso group generated from at least a part of NBA groups or ANBA groups. For this reason, in a case where the polymer compound of the present embodiment in a solid phase state is irradiated with light, solvent solubility is decreased.

A composite material according to an embodiment of the present invention includes a base material and a layer containing the polymer compound of the present embodiment provided on a surface of the base material. In the composite material of the present embodiment, physical properties of a surface can be changed by irradiation with light. More specifically, solubility of the polymer compound present on a surface of the composite material in a solvent such as water, or crosslinking reaction of the polymer compound can be induced by irradiation with light. Light can be irradiated from a base material side of the composite material to the layer containing the polymer compound of the present embodiment. Thus, it is preferable that the base material be formed of a material that transmits light. As the base material, a plastic substrate or film such as polystyrene, polymethylpentene, polycarbonate, and cycloolefin polymer, glass, quartz, silicone resin, or a cellulose-based film material such as a dialysis membrane are mentioned.

In addition, a composite layer obtained by mixing the polymer compound of the present embodiment and a polymer compound which is not responsive to light can also be used as a layer containing a polymer compound in the composite material of the present embodiment. In a material in which a layered material formed of a gel or the like is additionally carried on the composite layer, depending on changes in physical properties of a region of the polymer compound of the present embodiment with which light is irradiated, promotion or suppression in peeling of the carried layered material can be controlled. In the composite material of the present embodiment, it is possible to change cell adhesiveness on a surface by irradiation with light.

Therefore, by using the composite material of the present embodiment as a culture substrate for cells, it is possible to control cell adhesiveness by causing all or a part of a surface of the composite material to be irradiated with light, thereby allowing cell sorting manipulations such as selectively peeling or capturing cultured cells. In particular, with the composite material of the present embodiment, it is possible to perform individual peeling of adherent cells and a colony as well as peeling of only a specific part (for example, pseudopodium) in a cell. For this reason, it is strongly expected that the polymer compound of the present embodiment will be a useful and powerful means of realization for detailed analysis of individual cell adhesion states in addition to cell sorting manipulations including refinement and selective acquisition.

A method for manipulating a cell according to an embodiment of the present invention includes a culturing step of culturing cells on a surface of the layer containing the polymer compound in the composite material of the present embodiment, a light-irradiating step of causing at least a part of a region of the surface of the layer containing the polymer compound to be irradiated with light, after the culturing step, and a removing step of removing cells that exist in the region which has been irradiated with light in the light-irradiating step. In the light-irradiation step, light can be irradiated from a base material side. In the removing step, it is possible to dissolve the layer containing the polymer compound in water so that a part of cultured cells is dissolved.

The polymer compound of the present embodiment in a solid phase state, such as a case where the polymer compound of the present embodiment is dried and a case where the polymer compound of the present embodiment is present in a poor solvent, is irradiated with light so that a crosslinked structure having solvent resistance is easily formed. For this reason, a separate material such as a crosslinked polymer can be carried, by spin coating, on a surface of a layer containing the polymer compound of the present embodiment.

A soluble property can also be induced by limiting a light-crosslinking reaction of the polymer compound of the present embodiment to some extent so that light-responsive groups remain and irradiating the polymer compound of the present embodiment with light in water or another solvent. For this reason, in a case where a gel that swells in a solvent is carried on the layer containing the polymer compound of the present embodiment, a gel layer is stably immobilized on the surface of the layer containing the polymer compound in a dark place, whereas the gel layer can be rapidly swelled and peeled off from the layer containing the polymer compound by irradiation with light. Since floating of the gel layer at that time is accompanied with a large movement, this makes it possible to use as a unidirectional light-driven actuator. That is, the light-driven actuator according to the embodiment of the present invention includes a light source and the composite material of the present embodiment.

EXAMPLES

The present invention will be described in detail in the following examples. However, the present invention is not limited to these examples. In addition, unless otherwise specified, ratio and % mean a mass ratio and % by mass, respectively.

Example 1: Synthesis of Compound 1 (Reaction Scheme (I))

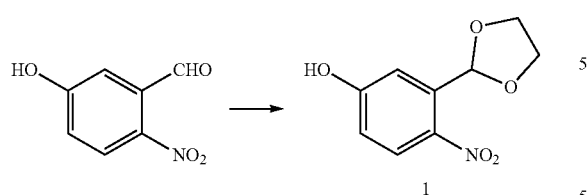

A benzene suspension of 5-hydroxy-2-nitrobenzaldehyde (1 equivalent), ethylene glycol (1.5 equivalents), and p-toluenesulfonic acid monohydrate (catalytic amount) were heated to reflux for several hours using a Dean-Stark apparatus. After cooling, the solvent was distilled off under reduced pressure, and the residue was separated and purified by a silica gel column (Merck 7734, ethyl acetate:hexane=1:4 to 3:7 (volume ratio)). Compound 1 was obtained in a yield of 80% to 95%. Compound 1 can also be synthesized by the method described in NPL 1.

Example 2: Synthesis of Compound 2 (Reaction Scheme (II))

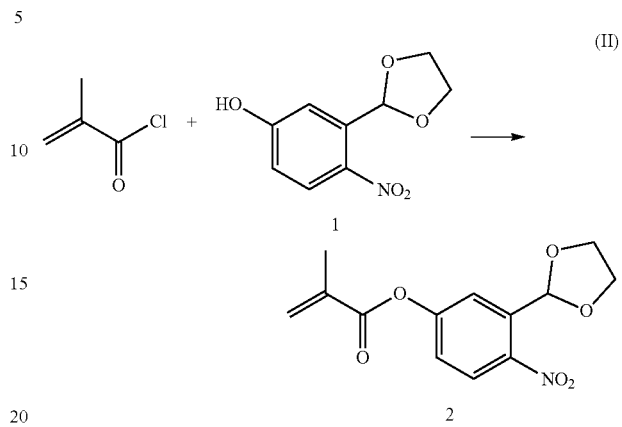

After stirring a dichloromethane solution of methacryloyl chloride (1 equivalent), Compound 1 (1.1 equivalent), and triethylamine (1.2 equivalent) at room temperature for several hours to a whole day and night, the reaction solution was treated with dilute hydrochloric acid. Thereafter, the mixture was extracted with dichloromethane, and the concentrated residue was purified with a silica gel column (Merck 7734, ethyl acetate:hexane=3:7 (volume ratio)). Compound 2 (compound represented by Formula (6)) was obtained in a yield of 90% or more.

$^1$H-NMR (CDCl$_3$): 8.02 (1H, d, J=8.8 Hz), 7.57 (1H, d, J=2.6 Hz), 7.29 (1H, dd, J=8.8, 2.6 Hz), 6.54 (1H, s), 6.39 (1H, m), 5.84 (1H, m), 4.04 (4H, m), 2.07 (3H, dd, J=1.5, 1.0 Hz)

Example 3: Synthesis of Compound 3 (Reaction Scheme (III))

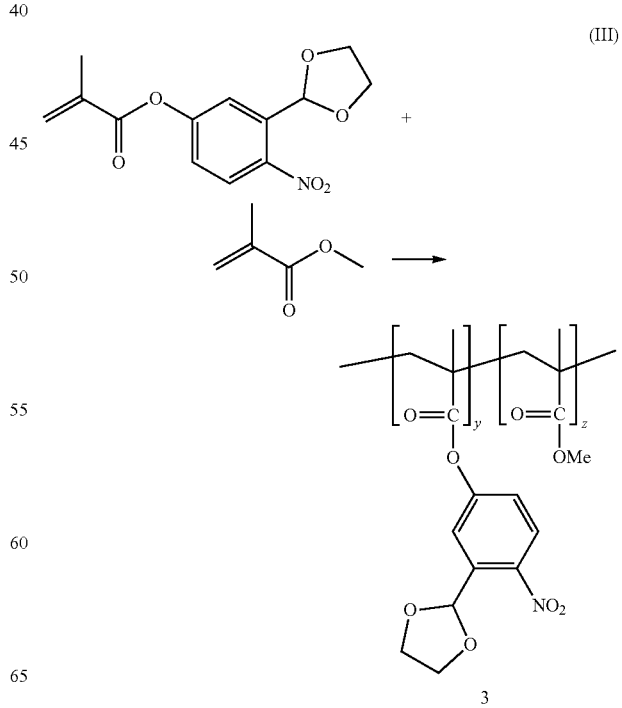

A solution of Compound 2, methyl methacrylate, and azoisobutyronitrile in anhydrous tetrahydrofuran was stirred at 65° C. for a whole day and night under a nitrogen stream. After cooling, the precipitate generated by being added dropwise to ether was collected by filtration. Reprecipitation was carried out using tetrahydrofuran-ether solution to obtain Compound 3. Specifically, weighing was carried out so that Compound 2:methyl methacrylate:azoisobutyronitrile became about 50:50:1 to 2 (molar ratio), and then polymerization and purification were carried out to obtain Compound 3 in a yield of 60% to 70%. From a $^1$H-NMR spectrum, a compositional ratio y:z of Compound 3 was estimated to be 49:51.

$^1$H-NMR (d-acetone): 8.04 (1H, bs), 7.58 (1H, bs), 7.45 (1H, bs), 6.42 (1H, bs), 3.97 (4H, m, OCH$_2$OCH$_2$O), 3.65 (3H, m), 2.67-1.71 (4H, m), 1.71-0.77 (6H, m)

Example 4: Synthesis of Compound 4 (Reaction Scheme (IV))

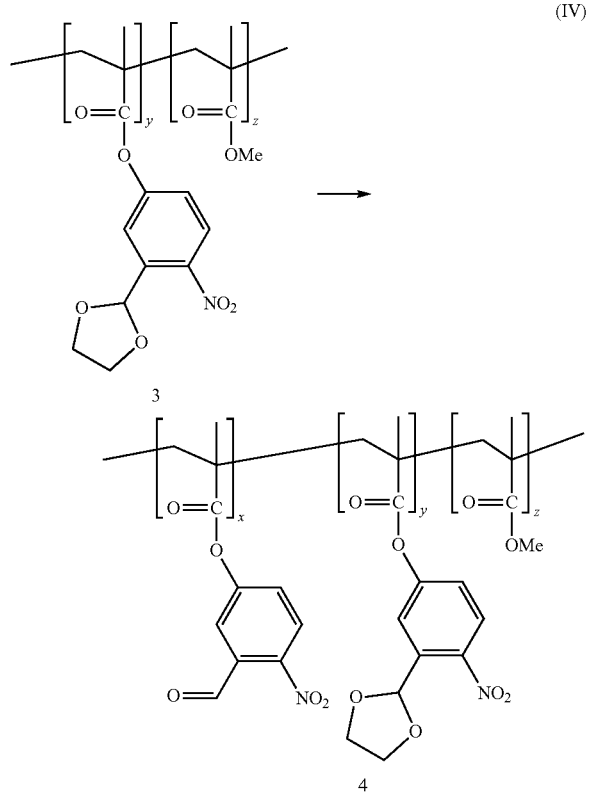

Dilute hydrochloric acid or concentrated hydrochloric acid was added to a chloroform solution of Compound 3, and the mixture was stirred at 40° C. to 70° C. for several hours to several days. After concentration, the precipitate generated by being added dropwise to ether was collected by filtration. Reprecipitation was carried out using a tetrahydrofuran-ether solution to obtain Compound 4. In a $^1$H-NMR (CDCl$_3$) spectrum, disappearance of peaks at 3.97 ppm and 6.42 ppm derived from acetal which had protected an aldehyde group, and appearance of a peak at 10.36 ppm derived from the aldehyde group confirmed production of Compound 4. In addition, a compositional ratio x:y:z of Compound 4 in the present example was estimated to be x:y:z=49:0:51 from an integrated value of peaks at around 7 to 8 ppm and 10 ppm derived from an aromatic ring of a nitrobenzaldehyde group and an integrated value of a peak at around 3.6 ppm derived from a methoxy group.

Example 5 Synthesis of Compound 5 (Reaction Formula (V))

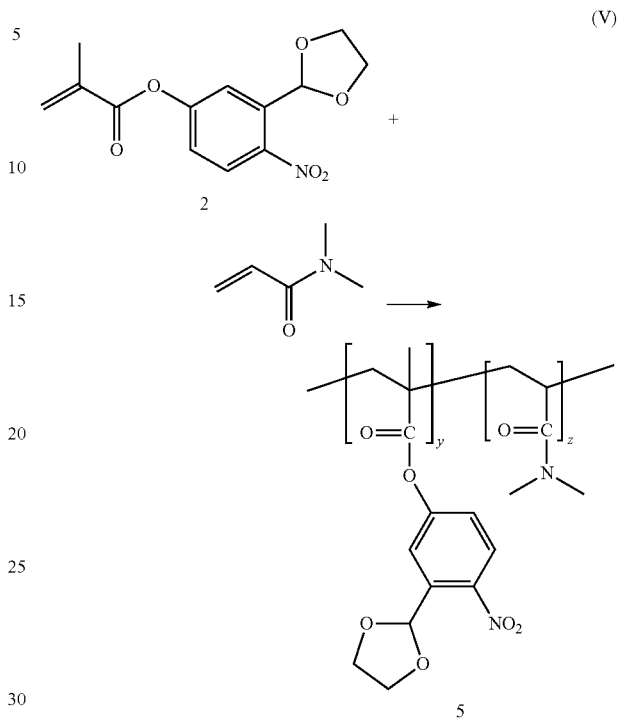

A solution of Compound 2, N, N-dimethylacrylamide, and azoisobutyronitrile in anhydrous tetrahydrofuran was stirred at 65° C. for a whole day and night under a nitrogen stream. After cooling, the precipitate generated by being added dropwise to ether was collected by filtration. Reprecipitation was carried out using tetrahydrofuran-ether solution to obtain Compound 5. Specifically, weighing was carried out so that Compound 2:N, N-dimethylacrylamide: azoisobutyronitrile became about 10:90:1 (molar ratio), and then polymerization and purification were carried out to obtain Compound 5 in a yield of 51%. From a $^1$H-NMR spectrum, a compositional ratio y:z of Compound 5 was estimated to be 14:86.

$^1$H-NMR (CDCl$_3$): 7.97 (1H, bs), 7.47 (1H, bs), 7.23 (1H, bs), 6.39 (1H, bs), 4.02 (4H, bs, OCH$_2$CH$_2$O), 3.25-0.86 (60H, m)

Example 6: Synthesis of Compound 6 (Reaction Scheme (VI))

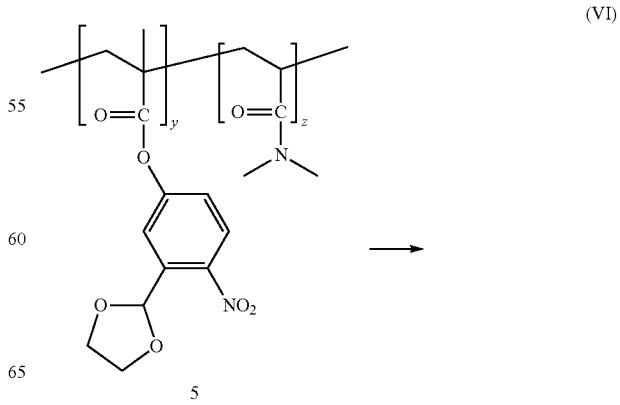

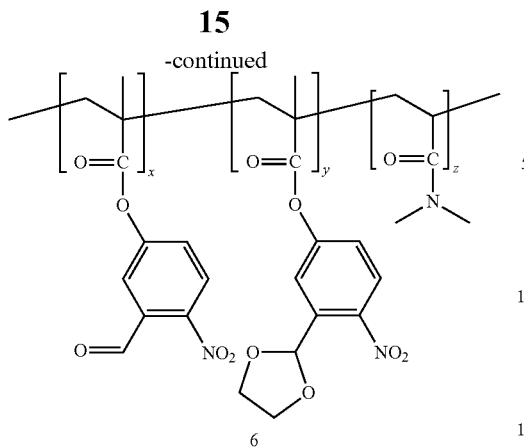

Concentrated hydrochloric acid was added to a chloroform or tetrahydrofuran solution of Compound 5, and the mixture was stirred at 60° C. for several hours to several days. The precipitate generated by dilution with ether was reprecipitated using tetrahydrofuran-ether to obtain Compound 6. In a $^1$H-NMR (CDCl$_3$) spectrum, a compositional ratio x:y:z of Compound 6 was calculated as 32:11:57 from an integrated value of a peak at around 4 ppm derived from acetal which had protected an aldehyde group and a peak at around 10 ppm derived from the aldehyde group.

Example 7: Synthesis of Compound 7 (Reaction Formula (VII))

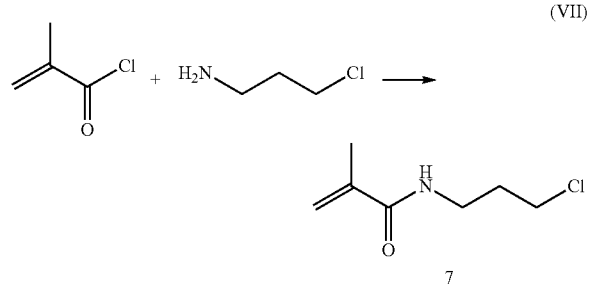

A solution of methacryloyl chloride (1 equivalent) in anhydrous dichloromethane was added dropwise to an anhydrous dichloromethane solution of ice-cooled 3-chloropropylamine hydrochloride (1.5 equivalents) and triethylamine (3 equivalents) under a nitrogen stream, and the mixture was stirred for a whole day and night. After treatment with dilute hydrochloric acid, extraction with dichloromethane was carried out, and the residue obtained by concentration was purified with a silica gel column (Merck 7734, ethyl acetate:hexane=3:2 (volume ratio)). Compound 7 was obtained in a yield of 50% to 60%.

$^1$H-NMR (CDCl$_3$): 6.08 (1H, bs), 5.69 (1H, bs), 5.34 (1H, bs), 3.61 (2H, t, J=6.3 Hz), 3.46 (2H, dt, J=6.0, 6.6 Hz), 2.05 (2H, tt, J=6.6, 6.3 Hz), 1.97 (3H, bs)

Example 8: Synthesis of Compound 8 (Reaction Formula (VIII))

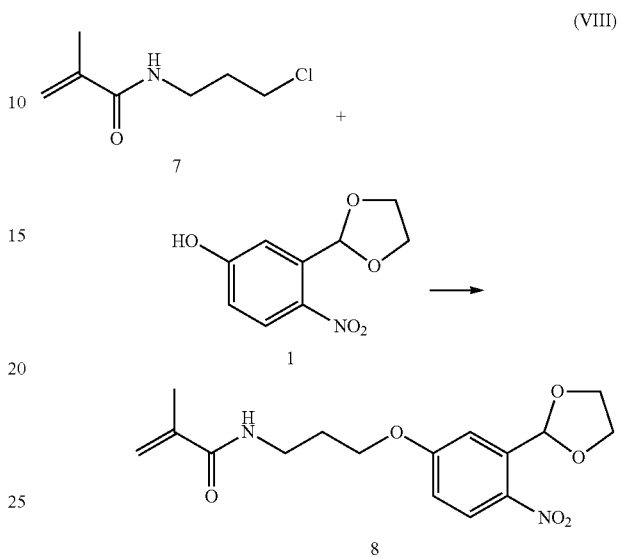

A solution of Compound 7 (1.1 equivalents), Compound 1 (1 equivalent), and anhydrous potassium carbonate (1.2 equivalents) in N,N-dimethylformamide was stirred at 120° C. for several hours and then treated with ice water. After extraction with ether, the residue obtained by concentration was purified with a silica gel column (Merck 7734, ethyl acetate:hexane=9:1 (volume ratio)). Compound 8 (a compound represented by Formula (7)) was obtained in a yield of 50% to 60%.

$^1$H-NMR (CDCl$_3$): 8.03 (1H, d, J=9.0 Hz), 7.29 (1H, d, J=2.8 Hz), 6.91 (1H, dd, J=9.0, 2.8 Hz), 6.55 (1H, s), 6.12 (1H, bs), 5.70 (1H, bs), 5.35 (1H, m), 4.15 (2H, t, J=5.9 Hz), 4.05 (4H, m), 3.54 (2H, m), 2.10 (2H, m), 1.98 (3H, bs)

Example 9: Synthesis of Compound 9 (Reaction Scheme (IX))

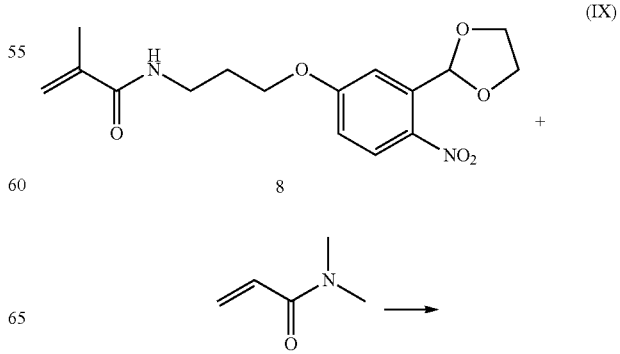

-continued

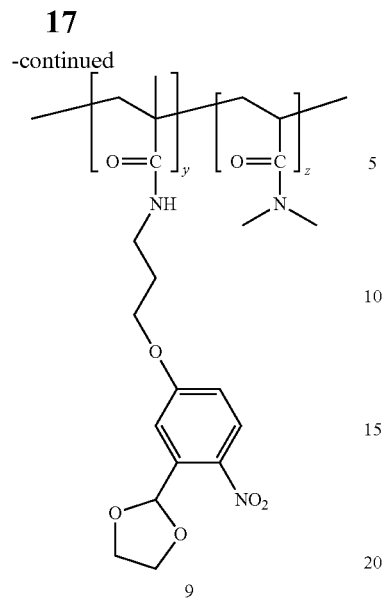

9

An anhydrous tetrahydrofuran solution containing Compound 8:N,N-dimethylacrylamide:azoisobutyronitrile in a molar ratio of 25:75:1 was stirred at 65° C. for a whole day and night under a nitrogen stream. After cooling, the precipitate generated by being added dropwise to ether was collected by filtration. Reprecipitation was carried out using tetrahydrofuran-ether solution to obtain Compound 9. In a $^1$H-NMR (CDCl$_3$) spectrum, a compositional ratio y:z of Compound 9 was estimated to be 22:78 from an integrated value of peaks at 6 to 8 ppm derived from Compound 8 and other peaks appearing at 1 to 4 ppm.

Example 10: Synthesis of Compound 10 (Reaction Scheme (X))

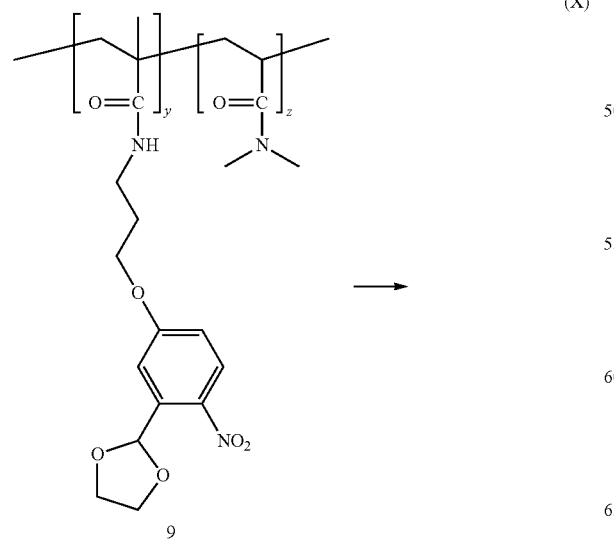

-continued

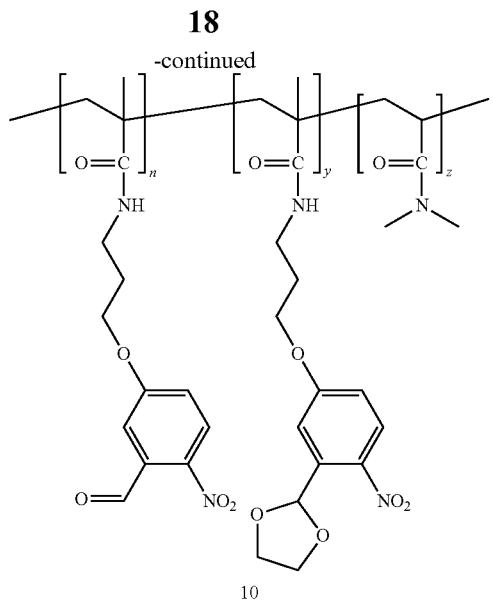

10

Dilute hydrochloric acid was added to a chloroform solution of Compound 9, and the mixture was stirred at 60° C. for 3 days. The precipitate generated by dilution with ether was reprecipitated using tetrahydrofuran-ether to obtain compound 10. In a $^1$H-NMR (CDCl$_3$) spectrum, a compositional ratio x:y:z of Compound 10 was estimated to be 17:5:78 from an integrated value of a peak at 4 ppm derived from acetal which had protected an aldehyde group and peaks at 7 to 8 ppm derived from an aromatic and an NH group.

Example 11: Synthesis of Compound 11 (Reaction Scheme (XI))

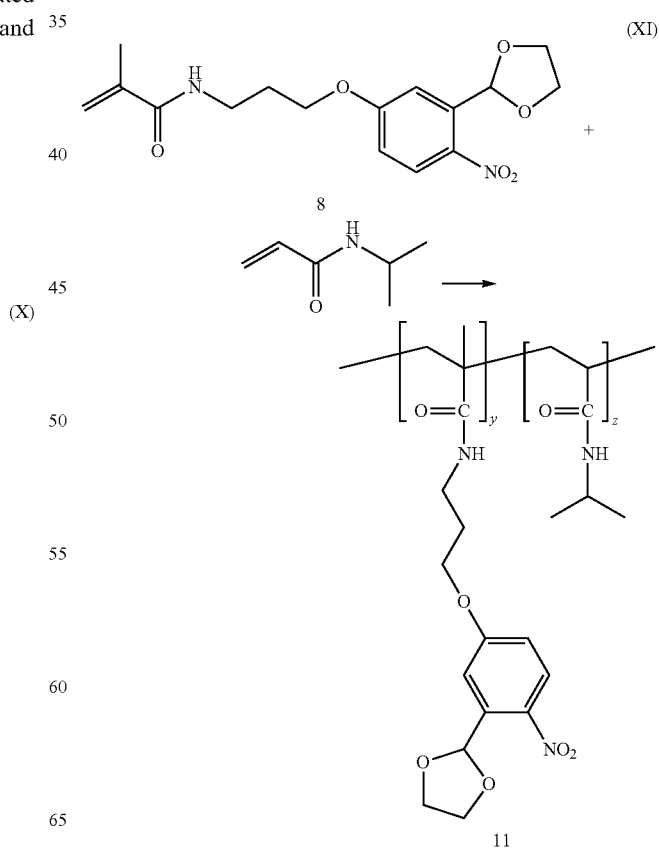

11

Compound 8: Anhydrous tetrahydrofuran solution containing N:isopropylacrylamide:azoisobutyronitrile in a molar ratio of 25:75:1 was stirred for a whole day and night at 65° C. under a nitrogen stream. After cooling, the precipitate generated by being added dropwise to ether was collected by filtration. Reprecipitation was carried out using tetrahydrofuran-ether solution to obtain Compound 11. In a $^1$H-NMR (CDCl$_3$) spectrum, a compositional ratio y:z of Compound 11 was estimated to be 25:75 from an integrated value of peaks at 7 to 8 ppm derived from an aromatic of Compound 8 and other peaks appearing at 1 to 4 ppm. The compositional ratio of Compound 11 was almost in agreement with a charging ratio of raw materials.

Example 12: Synthesis of Compound 12 (Reaction Scheme (XII))

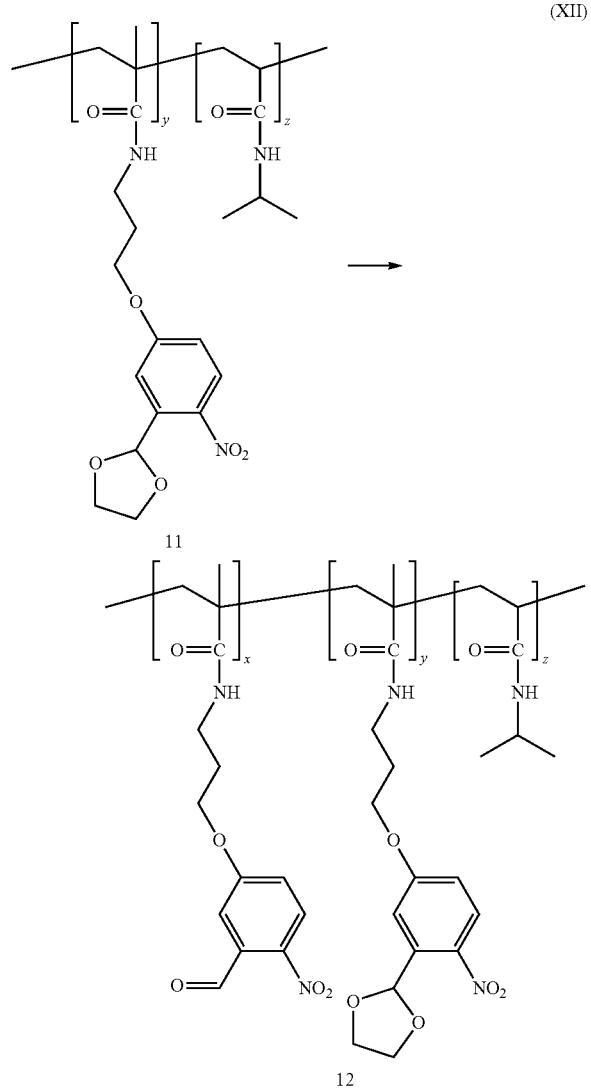

Dilute hydrochloric acid was added to a chloroform solution of Compound 11, and the mixture was stirred at 60° C. for 3 days. The precipitate generated by dilution with ether was reprecipitated with tetrahydrofuran-ether to obtain Compound 12. In a $^1$H-NMR (CDCl$_3$) spectrum, a compositional ratio x:y:z of Compound 12 was estimated to be 25:0:75 from disappearance of a peak at 4 ppm derived from acetal which had protected an aldehyde group. That is, Compound 12 was a compound in which most of acetal-protected aldehyde groups of Compound 11 were changed to aldehyde groups.

Example 13: Synthesis of Compound 13 (Reaction Scheme (XIII))

After stirring an anhydrous dichloromethane solution of methacryloyl chloride (1.1 equivalents), 5-hydroxy-2-nitrobenzaldehyde (1 equivalent), and triethylamine (1.2 equivalents) for a whole day and night, the reaction solution was treated with dilute hydrochloric acid. After extraction with dichloromethane, the residue obtained by concentration was purified with a silica gel column (Merck 7734, ethyl acetate:hexane=3:7 (volume ratio)). Compound 13 was obtained in a yield of 87% or more.

$^1$H-NMR (CDCl$_3$): 10.45 (1H, s), 8.22 (1H, d, J=8.8 Hz), 7.71 (1H, d, J=2.6 Hz), 7.55 (1H, dd, J=8.8, 2.6 Hz), 6.41 (1H, s), 5.88 (1H, m), 2.08 (3H, dd, J=1.4, 1.0 Hz)

Example 14: Light-Responsive Swelling of Compound 4 (x=33, y=16, z=51)

Figure 3:
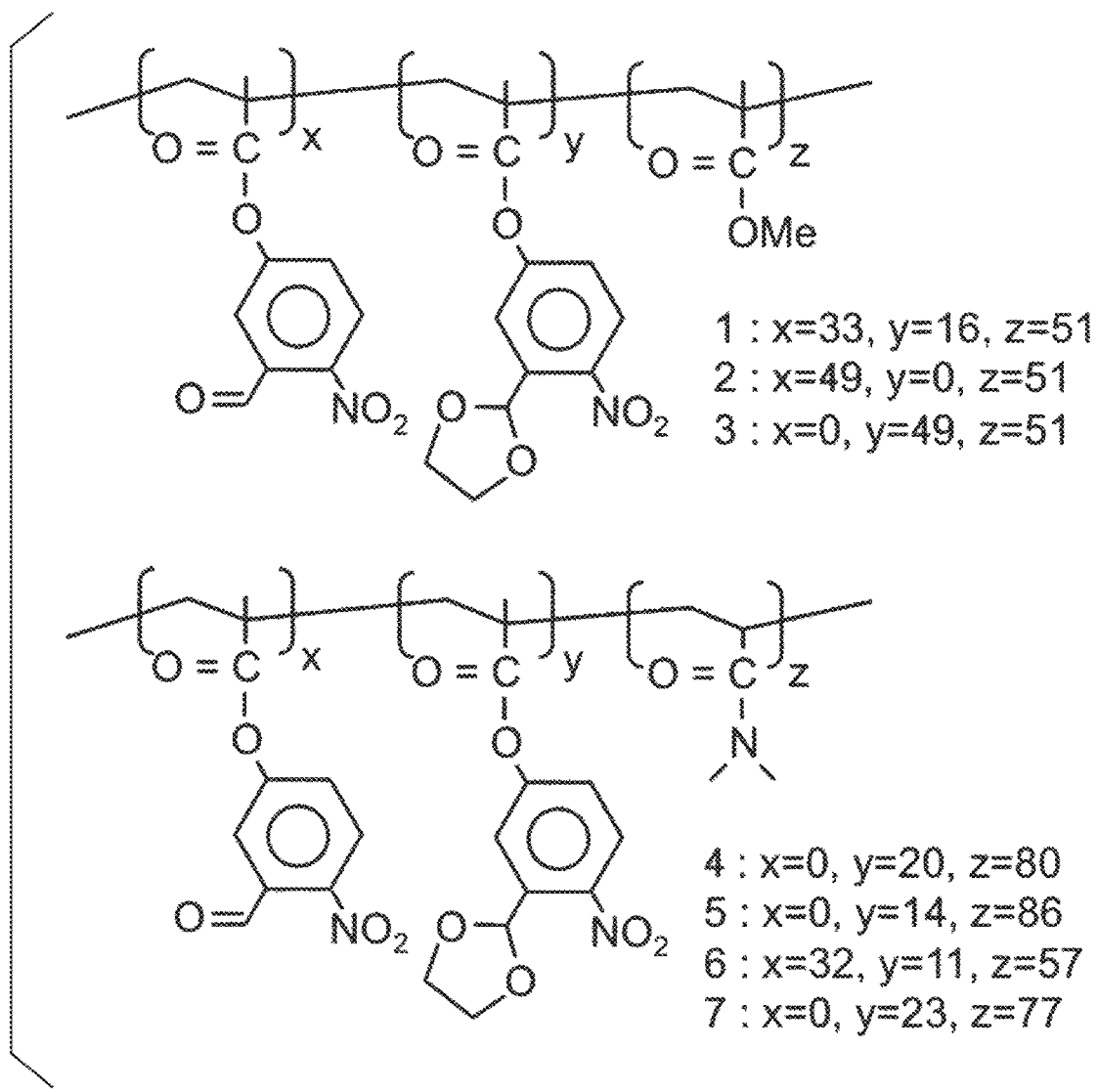
FIG. 3 is formulas of polymer compounds of the present embodiment used in Examples 14 to 21.
Figure 4:
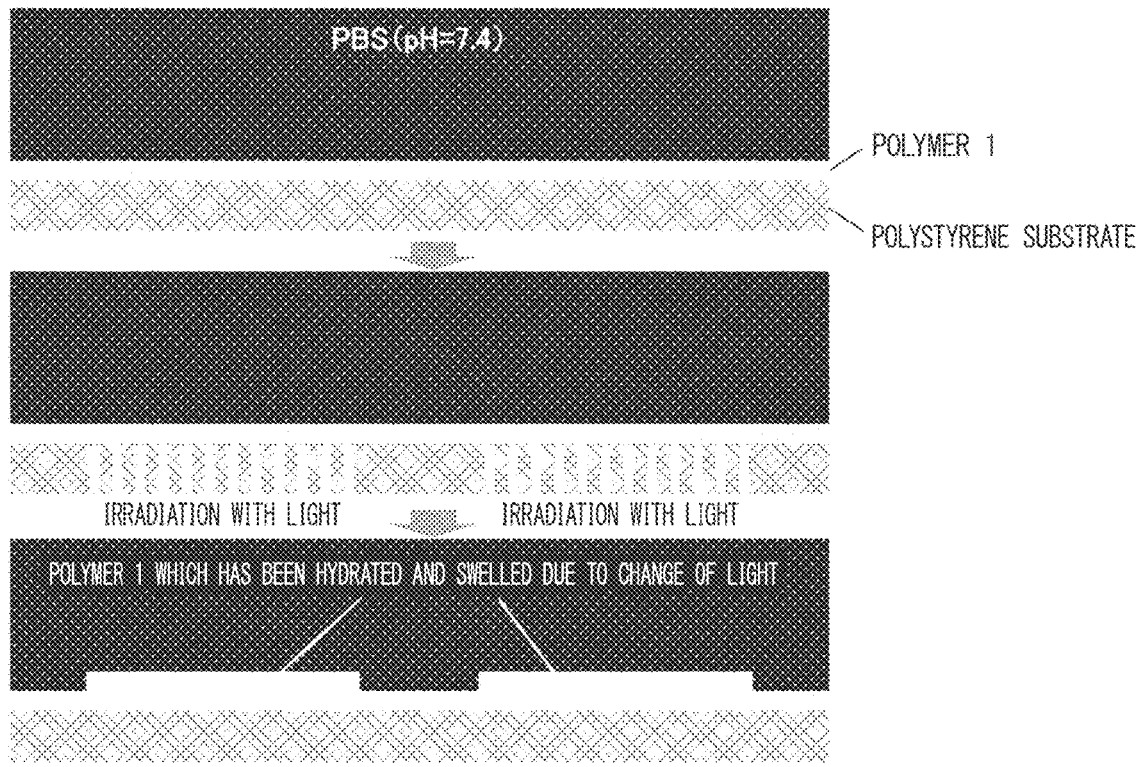
FIG. 4(a) is a schematic diagram for describing light-responsive swelling of Example 14.
FIG. 4(b) is an image of a bottom surface of a composite material after the light-responsive swelling.
Figure 4:
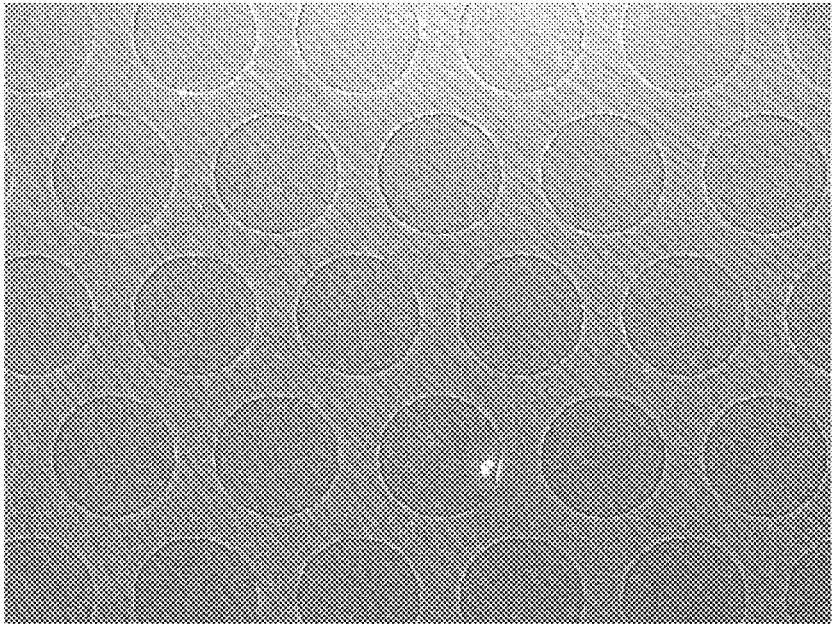

Polymer 1 (Compound 4 in which x=33, y=16, z=51) shown in FIG. 3 was prepared in the same manner as in Example 4. A solution of Polymer 1 in 2% 2,2,2-trifluoroethanol (TFE) was spin-coated on a hydrophilically-treated polystyrene substrate and heated at 85° C. for 1 hour to obtain a composite material. With this composite material immersed in a phosphate buffer solution (PBS) at pH 7.4, as shown in FIG. 4(a), in a case where Polymer 1 was irradiated with light having a wavelength of 365 nm and an intensity of 120 mW/cm$^2$ in a dot shape of a predetermined pattern for 10 seconds from a polystyrene substrate side, Polymer 1 in a region which had been irradiated with light swelled immediately. FIG. 4(b) is an image obtained by observing the composite material from a bottom surface with an inverted microscope after light-responsive swelling.

Example 15: Light-Responsive Peeling of Compound 4 (x=49, y=0, z=51)

Figure 5:
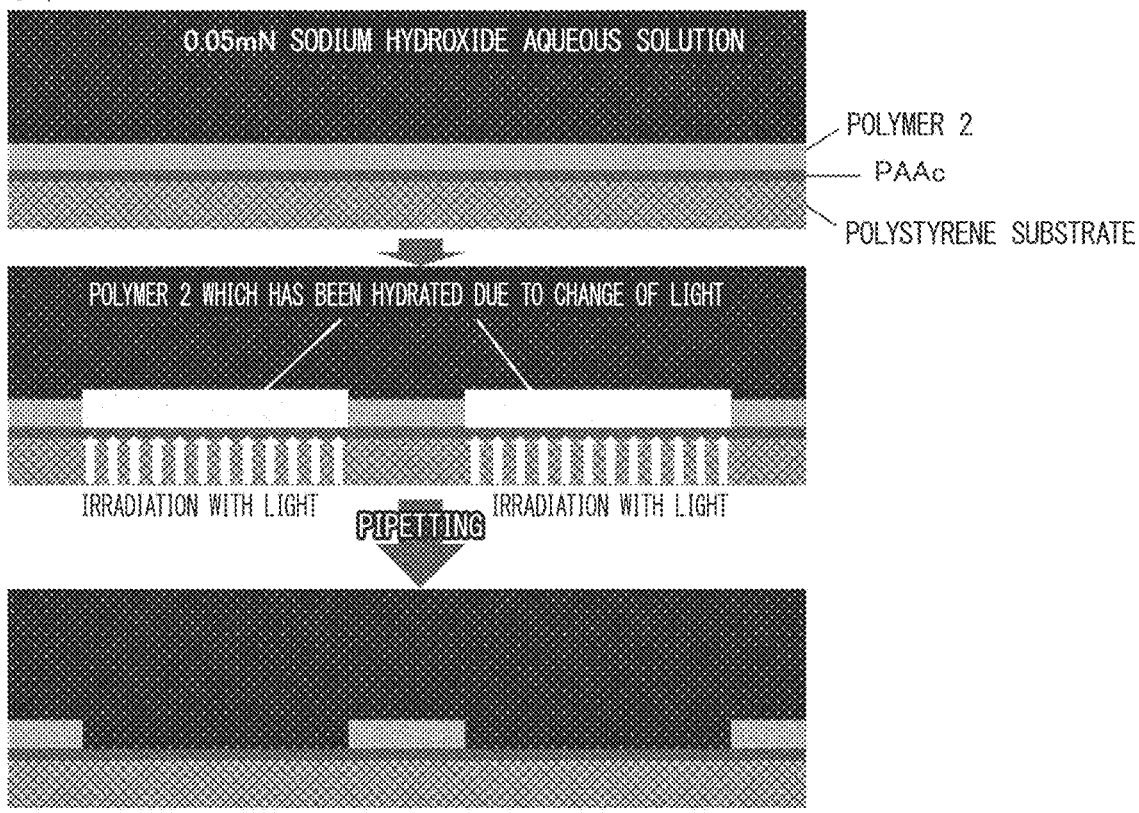
FIG. 5(a) is a schematic diagram for describing light-responsive peeling of Example 15.
FIG. 5(b) is an image of a bottom surface of a composite material after the light-responsive peeling.
Figure 5:
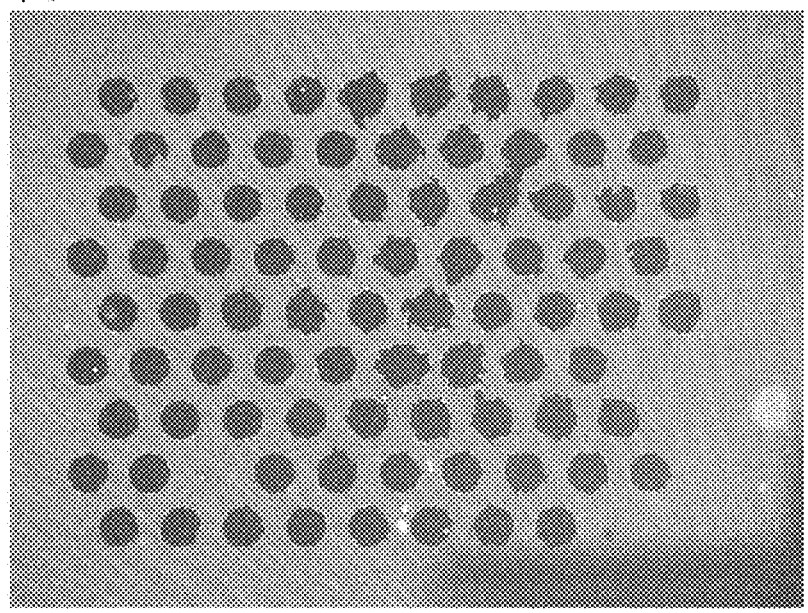

A solution of polyacrylic acid (PAAc) in 0.05% methanol was spin-coated on a polystyrene substrate for tissue culture and heated at 85° C. for 2 hours to prepare a PAAc-modified polystyrene base material. In addition, Polymer 2 (Compound 4 in which x=49, y=0, z=51) shown in FIG. 3 was prepared in the same manner as in Example 4. A solution obtained by dissolving 0.2% of Polymer 2 in a mixed solvent of 2,2,2,3,3,3-hexafluoroisopropanol (HFIP) and TFE was spin-coated on this base material and heated at 85° C. for 30 minutes to obtain a composite material. With this composite material immersed in a 0.05 mN sodium hydroxide aqueous solution, as shown in FIG. 5(a), Polymer 2 was irradiated with light having a wavelength of 365 nm and an intensity of 66 mW/cm$^2$ in a dot shape of a predetermined pattern for 30 seconds from a polystyrene substrate side. Thereafter, in a case where a surface of the composite material was pipetted, Polymer 2 was peeled off from a region which had been irradiated with light.

Example 16: Light-Responsive Peeling of Compound 4 (x=0, y=49, z=51)

Figure 6:
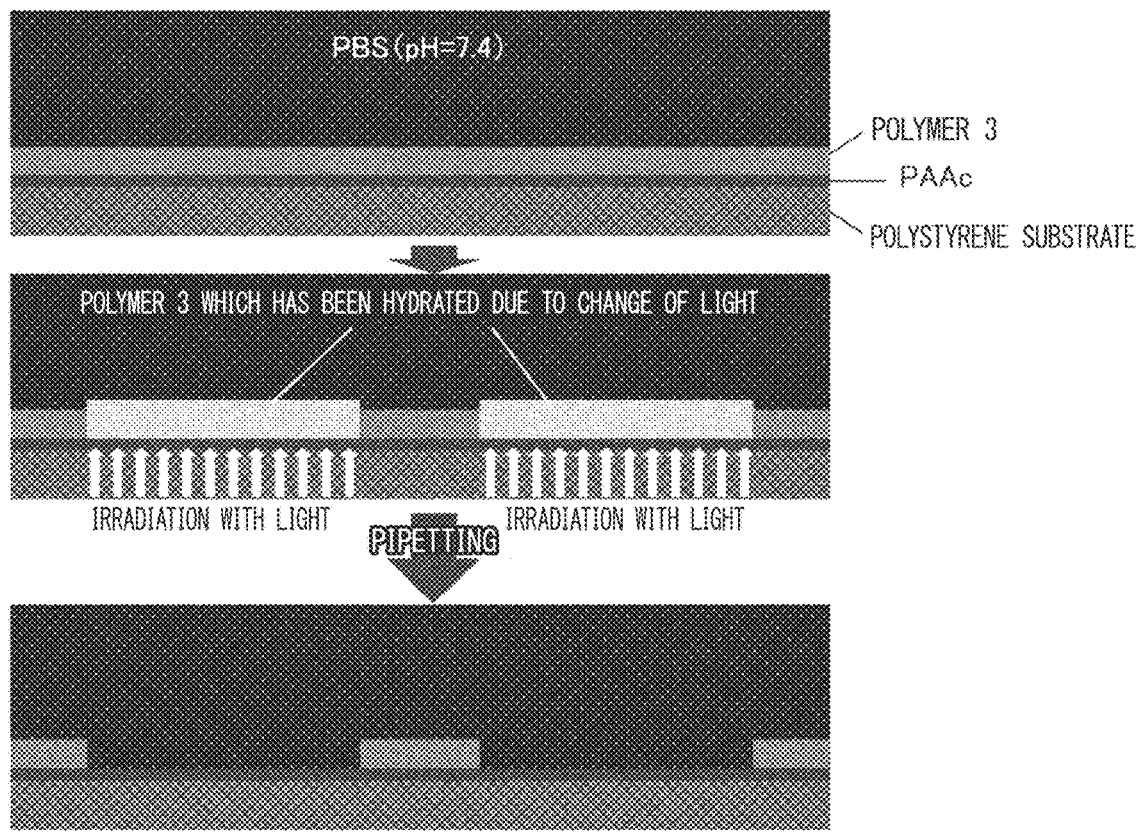
FIG. 6(a) is a schematic diagram for describing light-responsive peeling of Example 16.
FIG. 6(b) is an image of a bottom surface of a composite material after the light-responsive peeling.
Figure 6:
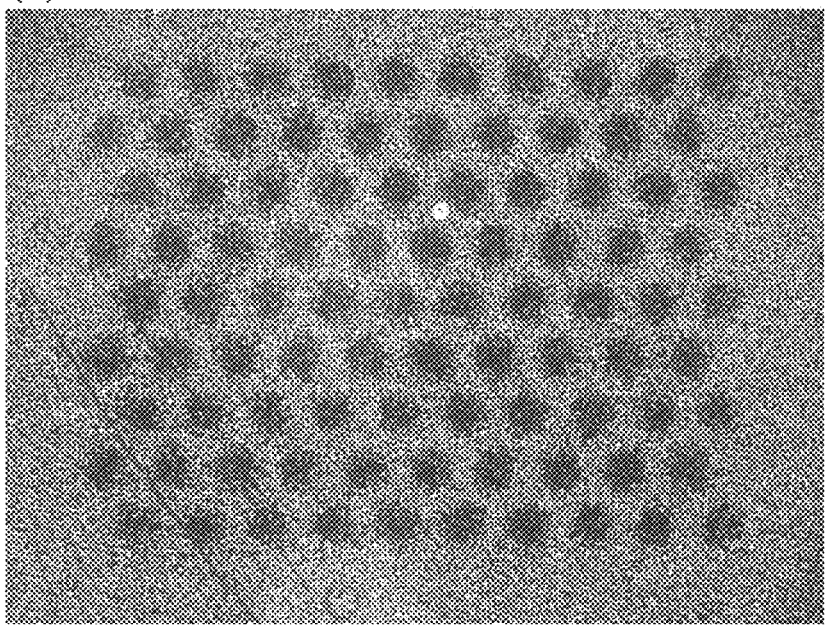

A solution of PAAc in 0.1% methanol was spin-coated on a polystyrene substrate for tissue culture and heated at 85° C. for 2 hours to prepare a PAAc-modified polystyrene base material. In addition, Polymer 3 (Compound 4 in which x=0, y=49, z=51) shown in FIG. 3 was prepared in the same manner as in Example 4. A solution obtained by dissolving 0.41% of Polymer 3 in a mixed solvent of 77% of HFIP and 23% of TFE was spin-coated on this base material and heated at 85° C. for 2 hours to obtain a composite material. With this composite material immersed in PBS at pH 7.4, as shown in FIG. 6(a), Polymer 3 was irradiated with light having a wavelength of 365 nm and an intensity of 120 mW/cm$^2$ in a dot shape of a predetermined pattern for 2 minutes from a polystyrene substrate side. Thereafter, in a case where a surface of the composite material was pipetted, Polymer 3 was peeled off from a region which had been irradiated with light.

Example 17: Light-Responsive Peeling of Hydroxypropyl Cellulose Gel Layer from Composite Layer of Compound 4 (x=0, y=49, z=51) and Partially Hydrolyzed PMMA A mixed solution obtained by mixing a 2% TFE solution of Polymer 3 shown in FIG. 3 and a 0.2% TFE solution of partially hydrolyzed PMMA at 1:5 was spin-coated on a polystyrene substrate to obtain a composite material with a composite layer of Polymer 3 and the partially hydrolyzed PMMA provided on a surface thereof. A methanol solution containing 2% of hydroxypropylcellulose (HPC), 0.015% of tetramethoxymethyl glycoluril (TMMGU), and 3 mmol/kg of $H_2SO_4$, was spin-coated on the composite layer of the composite material and heated for 2 hours at 85° C. to form a crosslinked HPC layer.

Figure 7:
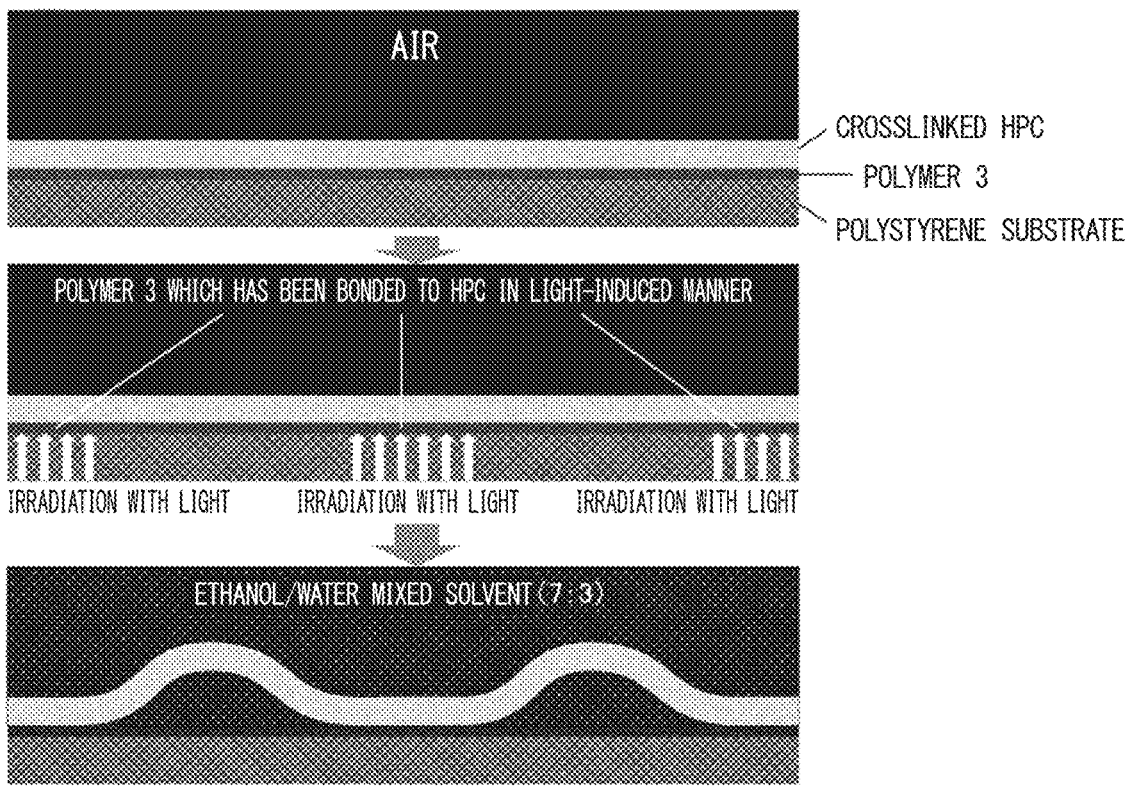
FIG. 7(a) is a schematic diagram for describing light-responsive peeling of Example 17.
FIG. 7(b) is an image of a bottom surface of a composite material after the light-responsive peeling.
Figure 7:

As shown in FIG. 7(a), the composite layer was irradiated with light having a wavelength of 365 nm and an intensity of 66 mW/cm$^2$ in a reversed dot shape of a predetermined pattern for 4 minutes from a polystyrene substrate side of this material on which the crosslinked HPC layer had been formed. Thereafter, in a case where this material was immersed in a mixed solution obtained by mixing ethanol and water at 7:3, the crosslinked HPC layer was spontaneously peeled off from the composite layer in a dot-shaped region which had not been irradiated with light. On the contrary, in a reversed dot-shaped region which had been irradiated with light, peeling of the crosslinked HPC layer from the composite layer was suppressed.

Example 18: Light-Responsive Dissolution Suppression of Compound 6 (x=0, y=20, z=80)

Figure 8:
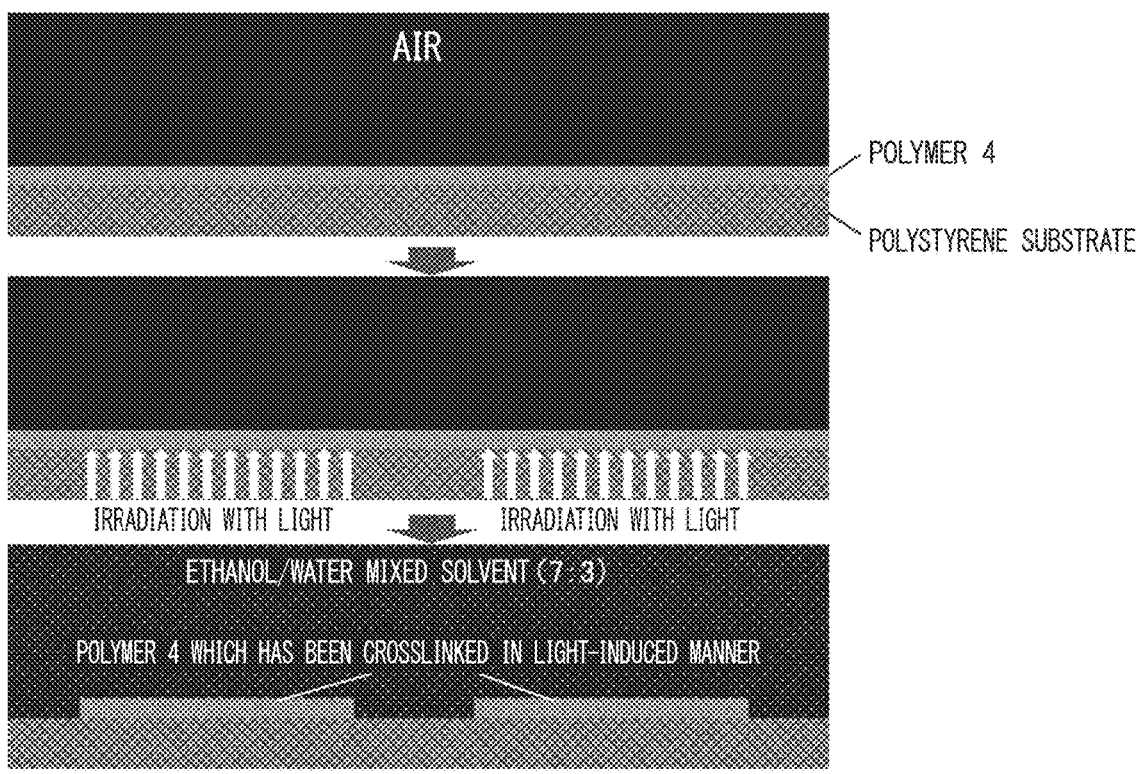
FIG. 8(a) is a schematic diagram for describing light-responsive dissolution suppression of Example 18.
FIG. 8(b) is an image of a bottom surface of a composite material after the light-responsive dissolution suppression.
Figure 8:
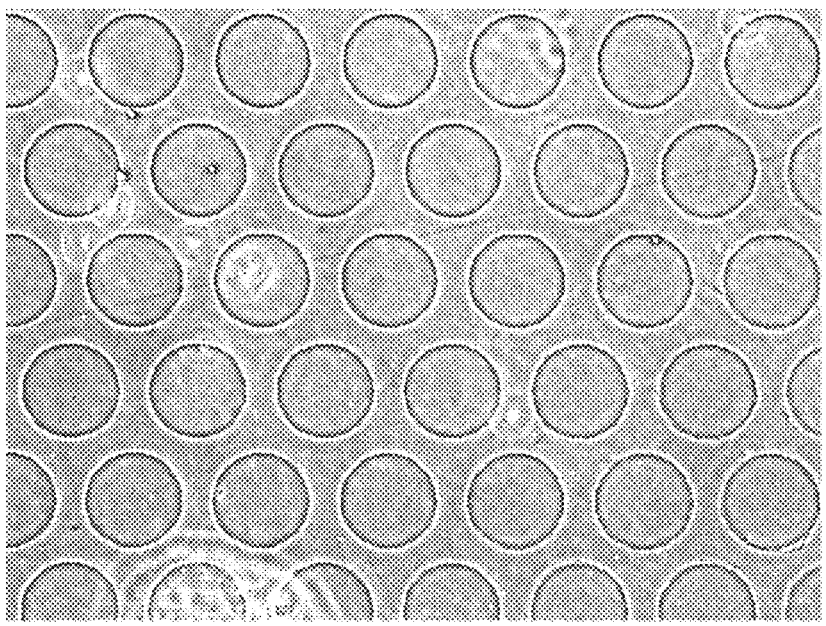

Polymer 4 (Compound 6 in which x=0, y=20, z=80) shown in FIG. 3 was prepared in the same manner as in Example 6. A solution of polymer 4 in 1% TFE was spin-coated on a polystyrene substrate and heated at 85° C. for 30 minutes to obtain a composite material. As shown in FIG. 8(a), Polymer 4 was irradiated with light having a wavelength of 365 nm and an intensity of 66 mW/cm$^2$ in a dot shape of a predetermined pattern in the air for 30 seconds from a polystyrene substrate side of the composite material. Thereafter, the composite material was immersed in a mixed solution obtained by mixing ethanol and water at 7:3. In a region which had not been irradiated with light, Polymer 4 was dissolved in the mixed solution and removed from the composite material, whereas in a region which had been irradiated with light, dissolution of Polymer 4 in the mixed solution was suppressed by crosslinking reaction of Polymer 4 and a crosslinked product of Polymer 4 remained in the composite material.

Figure 9:
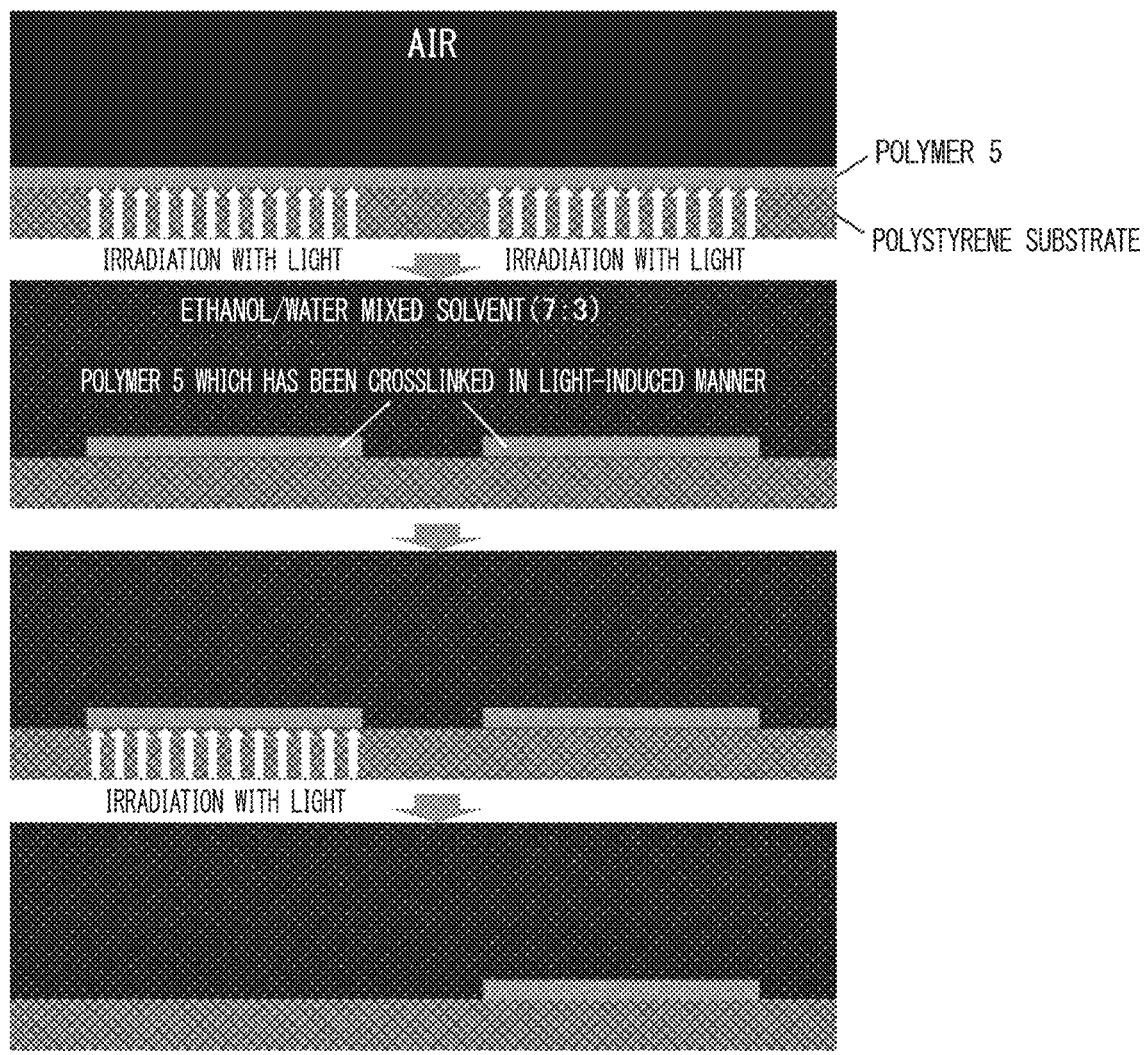
FIG. 9(a) is a schematic diagram for describing light-responsive crosslinking and light-responsive dissolution of a crosslinked body in Example 19.
FIG. 9(b) is an image of a bottom surface of a composite material after the light-responsive crosslinking.
FIG. 9(c) is an image of a bottom surface of a composite material after the light-responsive dissolution of the crosslinked body.

Example 19: Light-Responsive Crosslinking of Compound 6 (x=0, y=14, z=86) and Light-Responsive Dissolution of Crosslinked Product Polymer 5 (Compound 6 in which x=0, y=14, z=86) shown in FIG. 3 was prepared in the same manner as in Example 6. A solution of Polymer 5 in 1% TFE was spin-coated on a polystyrene substrate to obtain a composite material. As shown in FIG. 9(a), Polymer 5 was irradiated with light having a wavelength of 365 nm and an intensity of 66 mW/cm$^2$ in a dot shape of a predetermined pattern in the air for 20 seconds from a polystyrene substrate side of the composite material.

Thereafter, in a case where the composite material was immersed in a mixed solution obtained by mixing ethanol and water at 7:3, in a region which had not been irradiated with light, Polymer 5 was dissolved in the mixed solution and removed from the composite material, whereas in a region which had been irradiated with light, dissolution of Polymer 5 in the mixed solution was suppressed by crosslinking reaction of Polymer 5 and a crosslinked product of Polymer 5 remained in the composite material. Furthermore, Polymer 5 was locally irradiated with light having a wavelength of 360 to 440 nm and an intensity of 400 mW/cm$^2$ in a dot shape of a predetermined pattern for 1 minute. As a result, in a local region which had been irradiated with the additional light, a crosslinked product of Polymer 5 was dissolved in the mixed solution and removed from the composite material.

Example 20: Light-Responsive Peeling and Swelling of Compound 6 (x=32, y=11, z=57)

Figure 10:
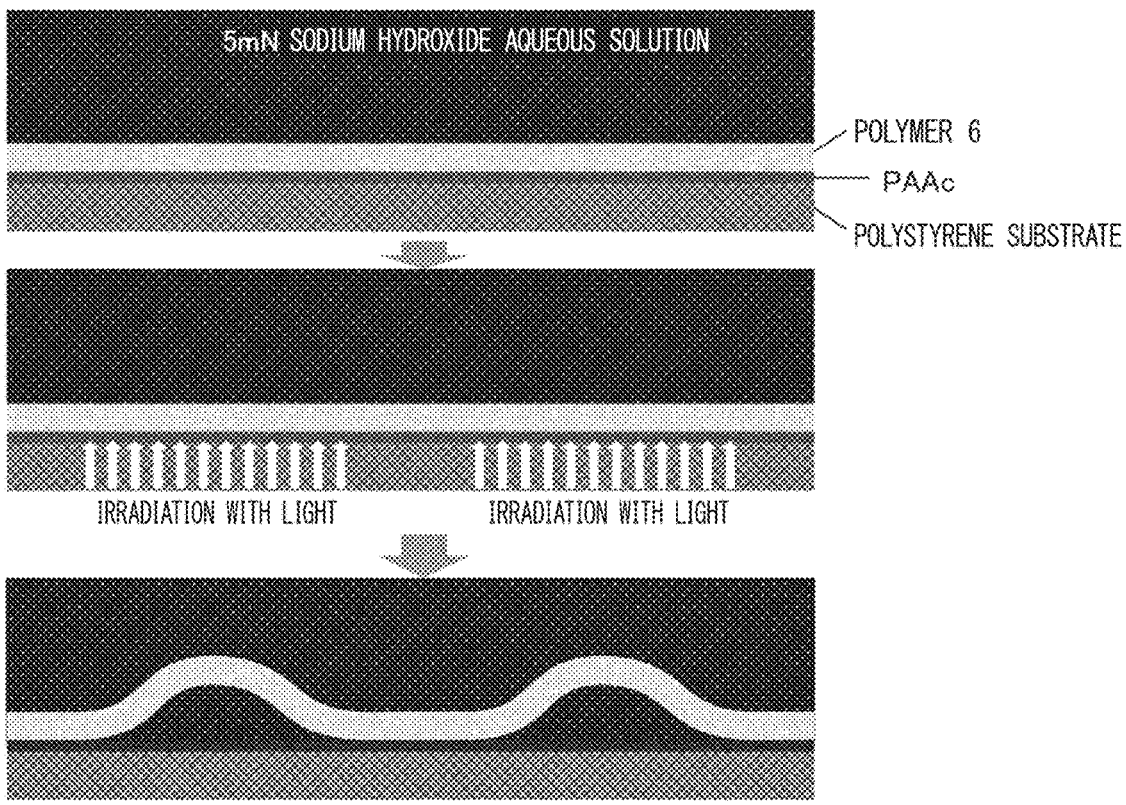
FIG. 10(a) is a schematic diagram for describing light-responsive peeling and swelling of Example 20.
FIG. 10(b) is an image of a bottom surface of a composite material after the light-responsive peeling and swelling.
Figure 10:
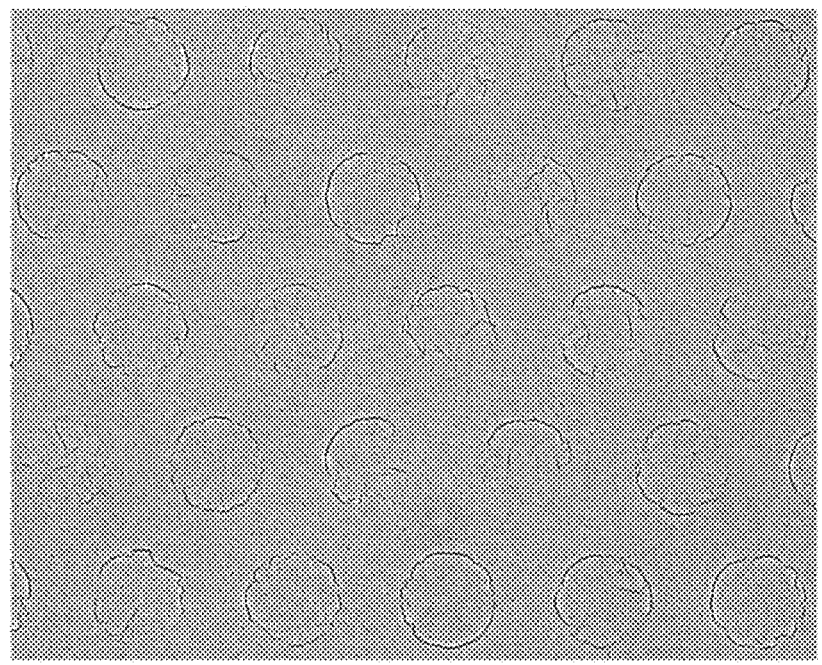

A solution of PAAc in 0.05% methanol was spin-coated on a polystyrene substrate for tissue culture and heated at 85° C. for 2 hours to prepare a PAAc-modified polystyrene base material. In addition, Polymer 6 (Compound 6 in which x=32, y=11, z=57) shown in FIG. 3 was prepared in the same manner as in Example 6. A solution of Polymer 6 in 0.5% TFE was spin-coated on this base material to obtain a composite material. With this composite material immersed in a 5 mN NaOH aqueous solution, as shown in FIG. 10(a), Polymer 6 was irradiated with light having a wavelength of 360 to 440 nm and an intensity of 400 mW/cm$^2$ in a dot shape of a predetermined pattern for 10 seconds from a polystyrene substrate side. In a region which had been irradiated with light, Polymer 6 was immediately peeled off from the PAAc layer and swelled.

Example 21: Light-Crosslinked Cell Patterning of Compound 6 (x=0, y=23, z=77)

Polymer 7 (Compound 6 in which x=0, y=23, z=77) shown in FIG. 3 was prepared in the same manner as in Example 6. In addition, a methanol solution containing 0.2% of HPC, 0.0015% of TMMGU, and 0.5 mmol/kg of $H_2SO_4$ was spin-coated on a polystyrene substrate for tissue culture and heated at 85° C. for 2 hours to form a crosslinked HPC layer having a cell adhesion inhibition property, so that an HPC gel-modified polystyrene base material was prepared. Furthermore, a solution in which 0.7% of Polymer 7 was dissolved in a mixed solvent obtained by mixing TFE and n-butanol at 7:3 was spin-coated on the crosslinked HPC layer to obtain a composite material.

Figure 11:
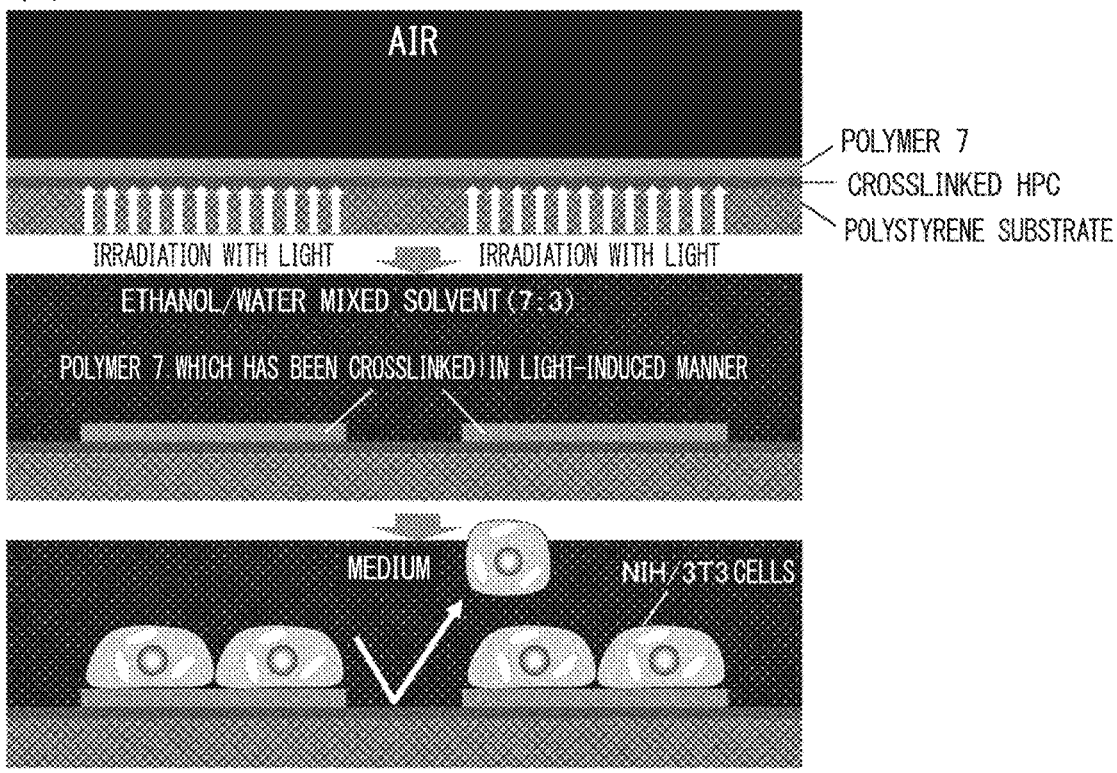
FIG. 11(a) is a schematic diagram for describing light-crosslinked cell patterning of Example 21.
FIG. 11(b) is an image of a bottom surface of a composite material after the light-crosslinked cell patterning.
Figure 11:
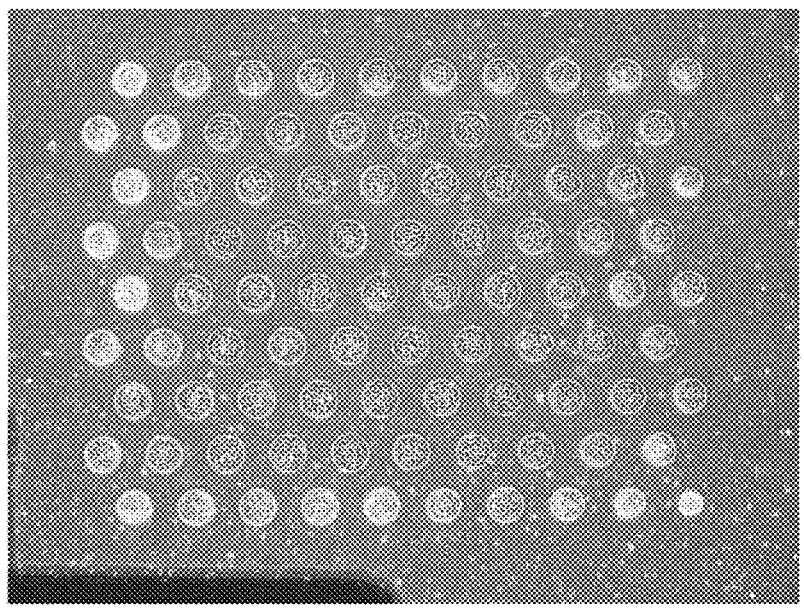

As shown in FIG. 11(a), Polymer 7 was irradiated with light having a wavelength of 365 nm and an intensity of 120 mW/cm$^2$ in a dot shape of a predetermined pattern in the air for 1 minute from a polystyrene substrate side of the composite material. A mixed solution obtained by mixing ethanol and water at 7:3 was sprayed onto a surface of the composite material and allowed to stand for 2 minutes. After gently shaking, the mixture solution was removed by suction. Thereafter, the composite material was washed twice with water. As a result, in a region which had not been irradiated with light, Polymer 7 was removed from the crosslinked HPC layer. On the other hand, in a region which had been irradiated with light, a crosslinked product of Polymer 7 remained on the crosslinked HPC layer. Then, NIH/3T3 cells dispersed in a medium were seeded on the composite material and cultured until the next day. As a result, the cells adhered to a surface of the crosslinked product of Polymer 7 that remained in the region which had been irradiated with light.

Example 22: Light-Responsive Dissolution of Compound 10 (x=17, y=5, z=78)

Figure 12:
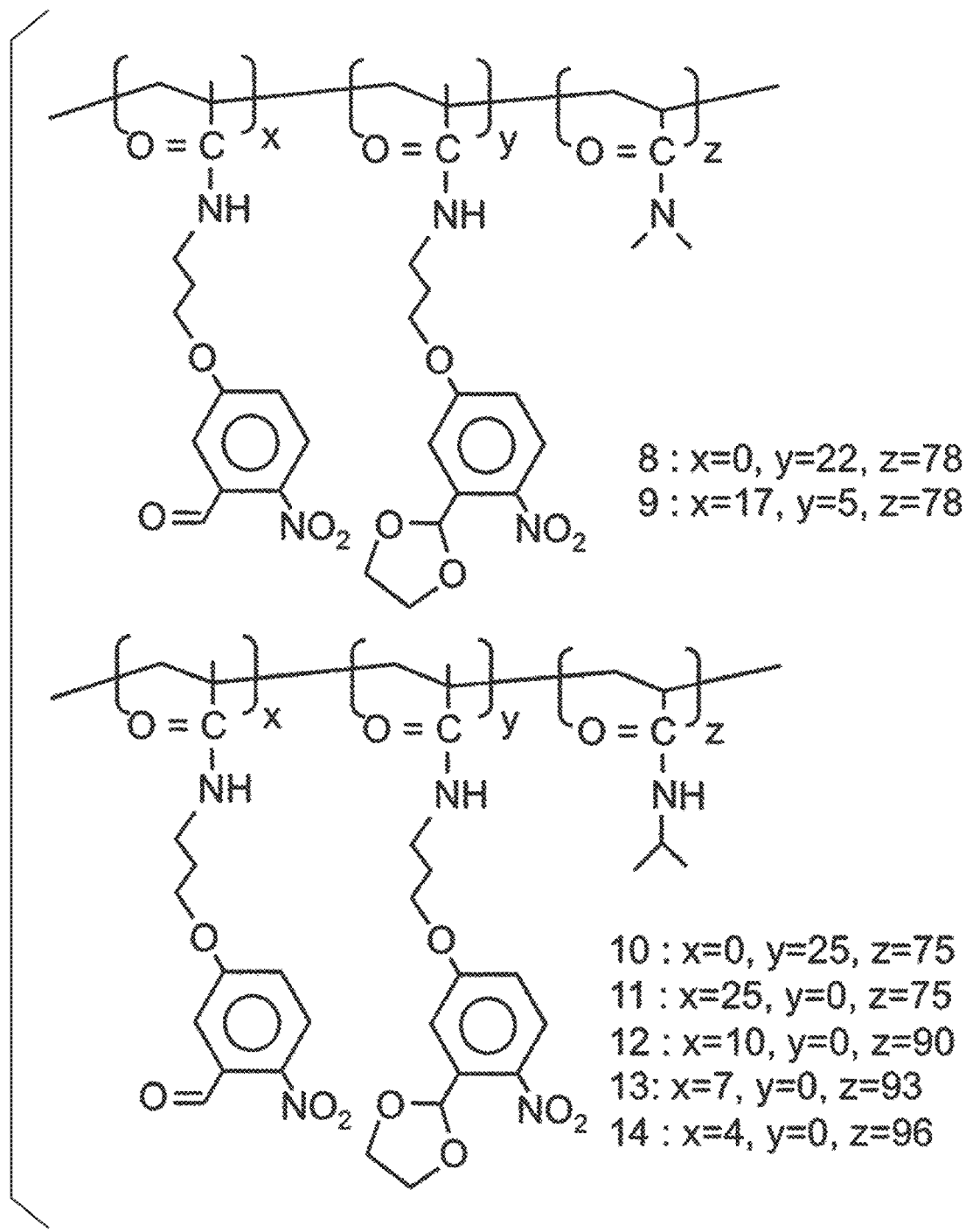
FIG. 12 is formulas of polymer compounds of the present embodiment used in Examples 22 to 33.
Figure 13:
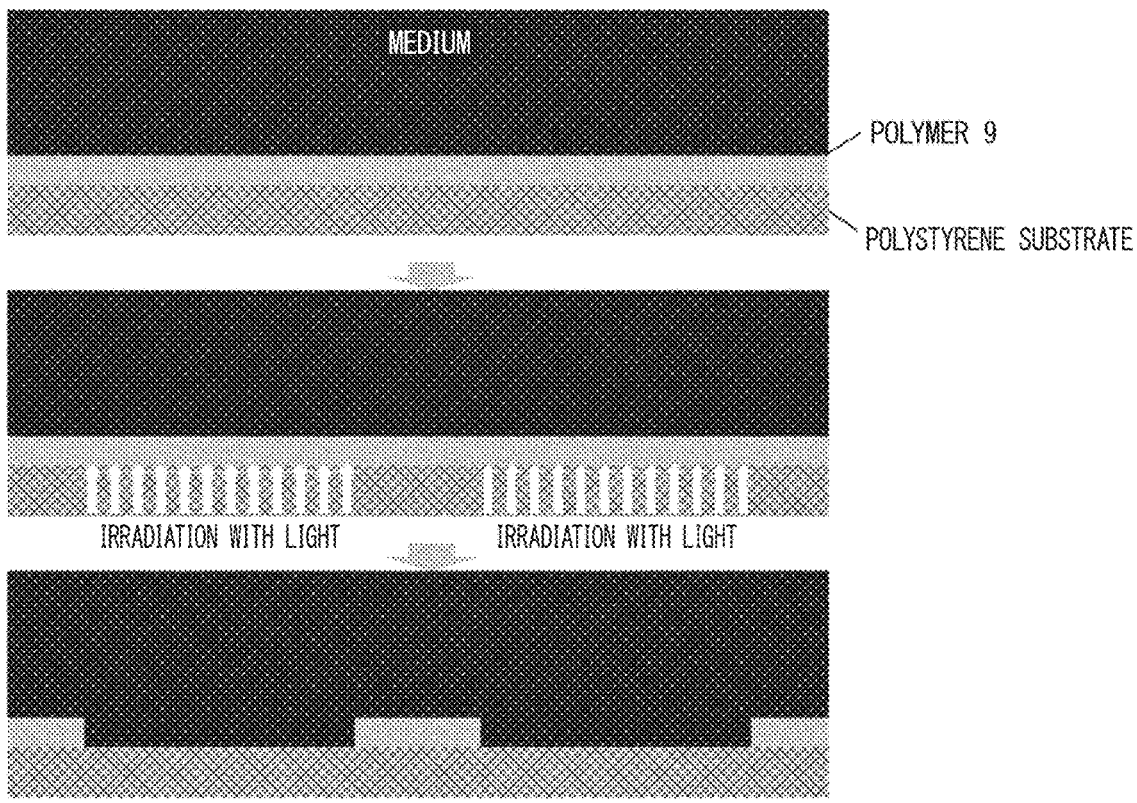
FIG. 13(a) is a schematic diagram for describing light-responsive dissolution of Example 22.
FIG. 13(b) is an image of a bottom surface of a composite material after the light-responsive dissolution.
Figure 13:
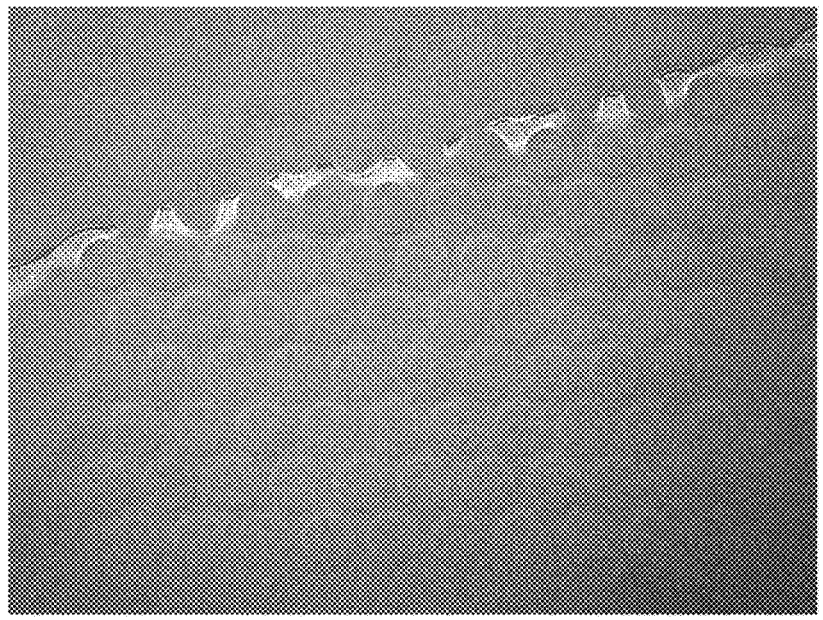

Polymer 9 (Compound 10 in which x=17, y=5, z=78) shown in FIG. 12 was prepared in the same manner as in Example 10. A solution of Polymer 9 in 1% TFE was spin-coated on a polystyrene substrate and heated at 85° C. for 2 hours to obtain a composite material. As shown in FIG. 13(a), in a case where Polymer 9 was irradiated with light having a wavelength of 365 nm and an intensity of 120 mW/cm$^2$ in a dot shape of a predetermined pattern for 2 seconds in a medium from a polystyrene substrate side of the composite material, Polymer 9 in a region which had been irradiated with light was dissolved in the medium.

Figure 14:
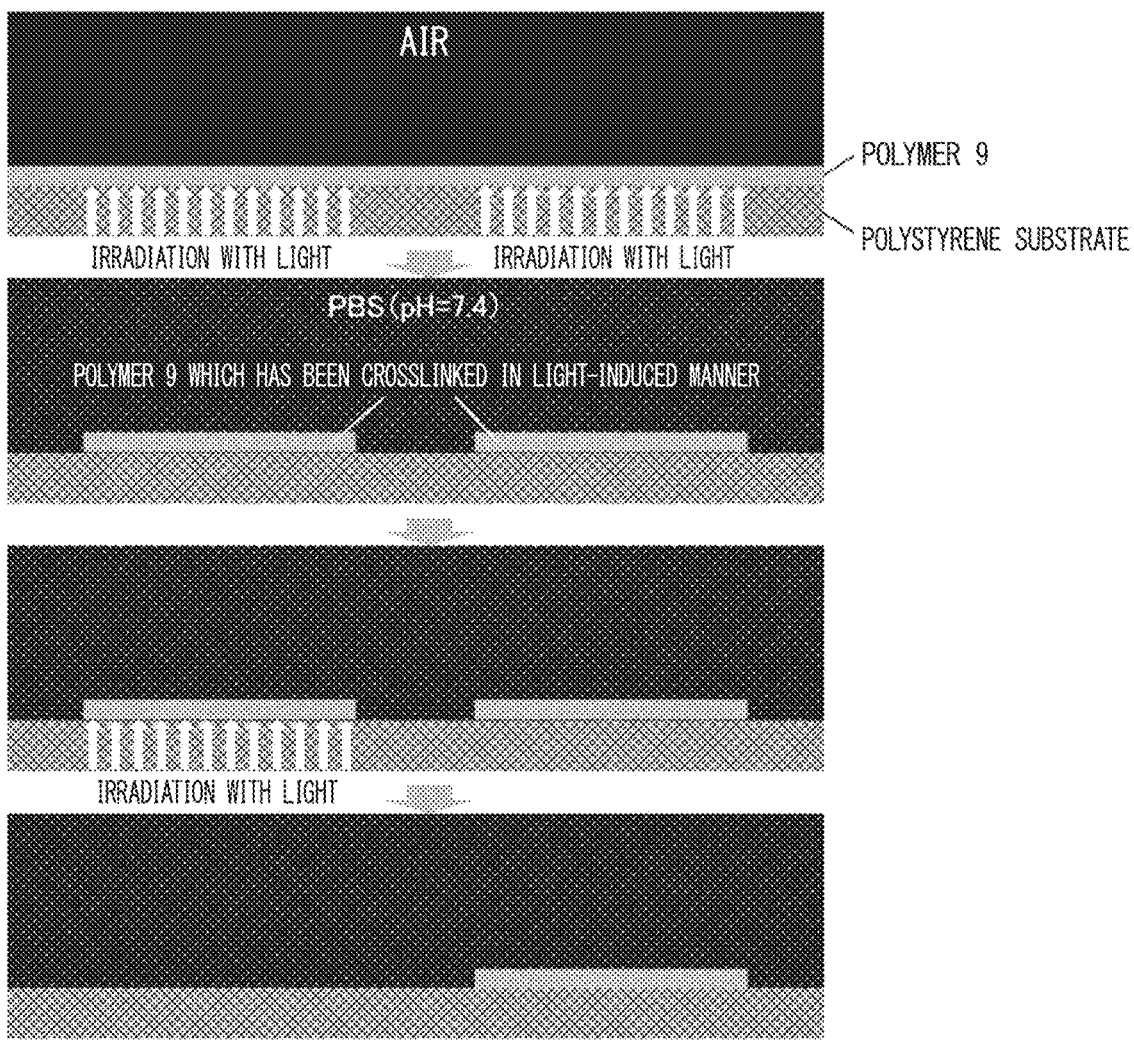
FIG. 14(a) is a schematic diagram for describing light-responsive crosslinking and light-responsive dissolution of a crosslinked body in Example 23.
FIG. 14(b) is an image of a bottom surface of a composite material after the light-responsive crosslinking.
FIG. 14(c) is an image of a bottom surface of a composite material after the light-responsive dissolution of the crosslinked body.
Figure 14:
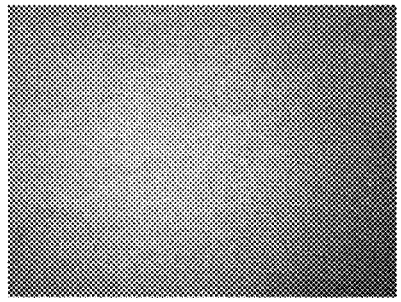
Figure 14:
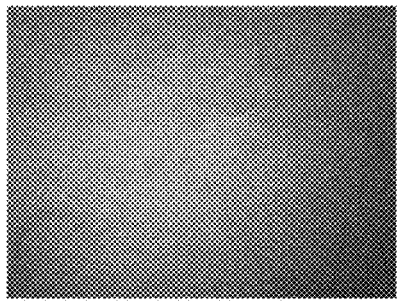

Example 23: Light-Responsive Crosslinking of Compound 10 (x=17, y=5, z=78) and Light-Responsive Dissolution of Crosslinked Product A solution of Polymer 9 shown in FIG. 12 in 1% TFE was spin-coated on a polystyrene substrate for tissue culture and heated at 85° C. for 15 minutes to obtain a composite material. As shown in FIG. 14(a), Polymer 9 was irradiated with light having a wavelength of 365 nm and an intensity of 66 mW/cm$^2$ in a dot shape of a predetermined pattern for 5 seconds from a polystyrene substrate side of the composite material in the air, and rinsed with water. Thereafter, the composite material was immersed in PBS at pH 7.4. As a result, in a region which had not been irradiated with light, Polymer 9 was gradually dissolved in PBS. On the other hand, in a region which had been irradiated with light, a crosslinked product of Polymer 9 remained on the polystyrene substrate. Furthermore, in a case where a part (rectangular shape) of the remaining Polymer 9 was irradiated with light having a wavelength of 365 nm and an intensity of 120 mW/cm$^2$ for 1 second from the polystyrene substrate side of the composite material in PBS, Polymer 9 in a region which had been irradiated with light was dissolved in PBS.

Example 24: Light-Responsive Peeling and Swelling of HPC Layer Derived from Compound 10 (x=17, y=5, z=78)

Figure 15:
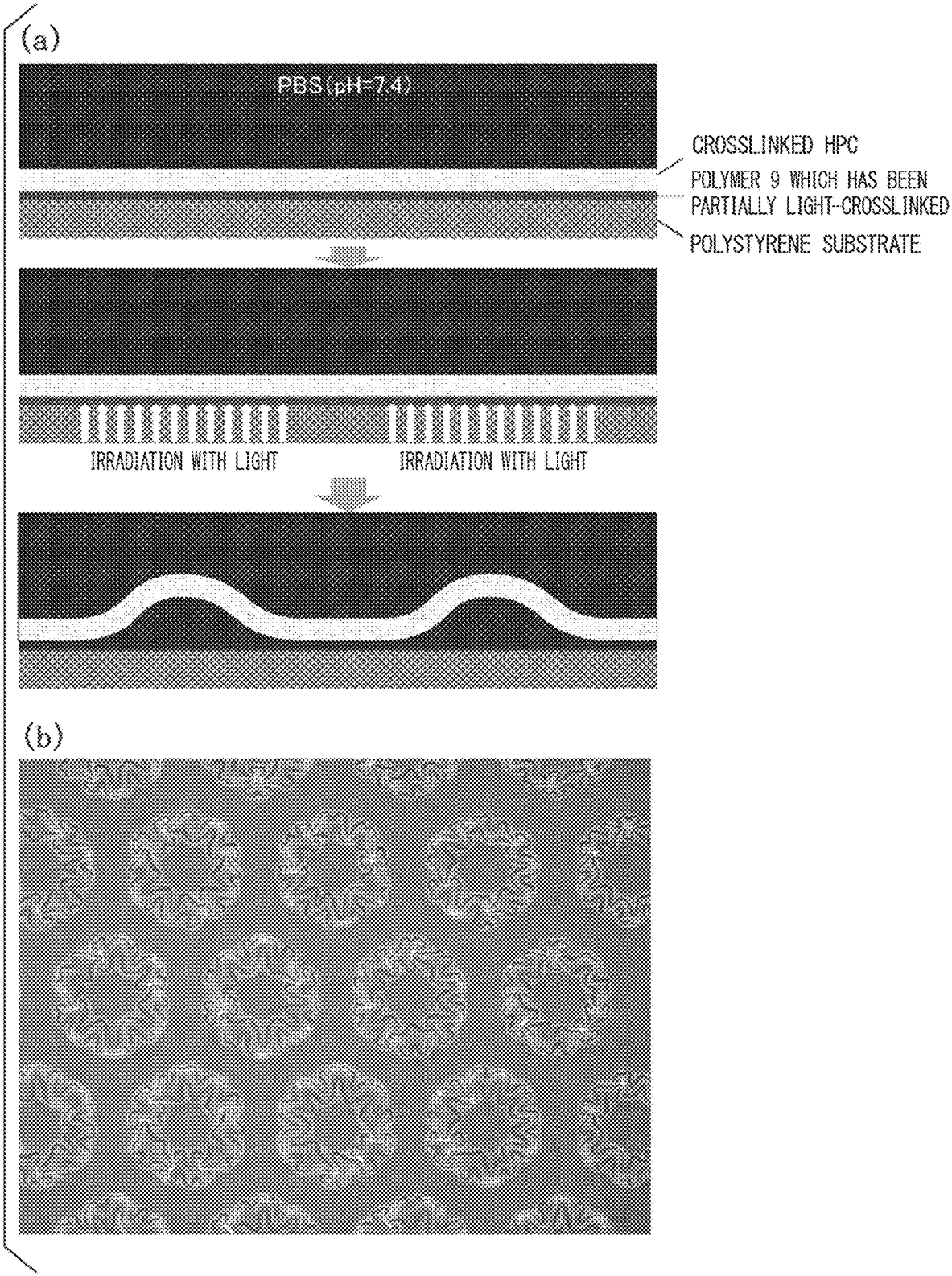
FIG. 15(a) is a schematic diagram for describing light-responsive peeling and swelling of Example 24.
FIG. 15(b) is an image of a bottom surface of a composite material after the light-responsive peeling and swelling.

A solution of Polymer 9 shown in FIG. 12 in 1% TFE was spin-coated on a polystyrene substrate and heated at 85° C. for 2 hours to obtain a composite material. The entire surface of a Polymer 9 layer of this composite material was irradiated with light having a wavelength of 365 nm and an intensity of 28 mW/cm$^2$ for 10 seconds, rinsed with water, and then dried. Furthermore, a methanol solution containing 3.6% of HPC, 0.044% of TMMGU, and 4.4 mmol/kg of $H_2SO_4$ was spin-coated on the Polymer 9 layer of the composite material and heated at 85° C. for 2 hours to form a crosslinked HPC layer. As shown in FIG. 15(a), Polymer 9 was irradiated with light having a wavelength of 365 nm and an intensity of 120 mW/cm$^2$ in a hexagonal shape of a predetermined pattern for 5 seconds from a polystyrene substrate side of the composite material in PBS at pH 7.4. In a region which had been irradiated with light, Polymer 9 was immediately peeled off from the polystyrene substrate and swelled.

Example 25: Light-Responsive Peeling of Cells from Compound 10 (x=17, y=5, z=78)

Figure 16:
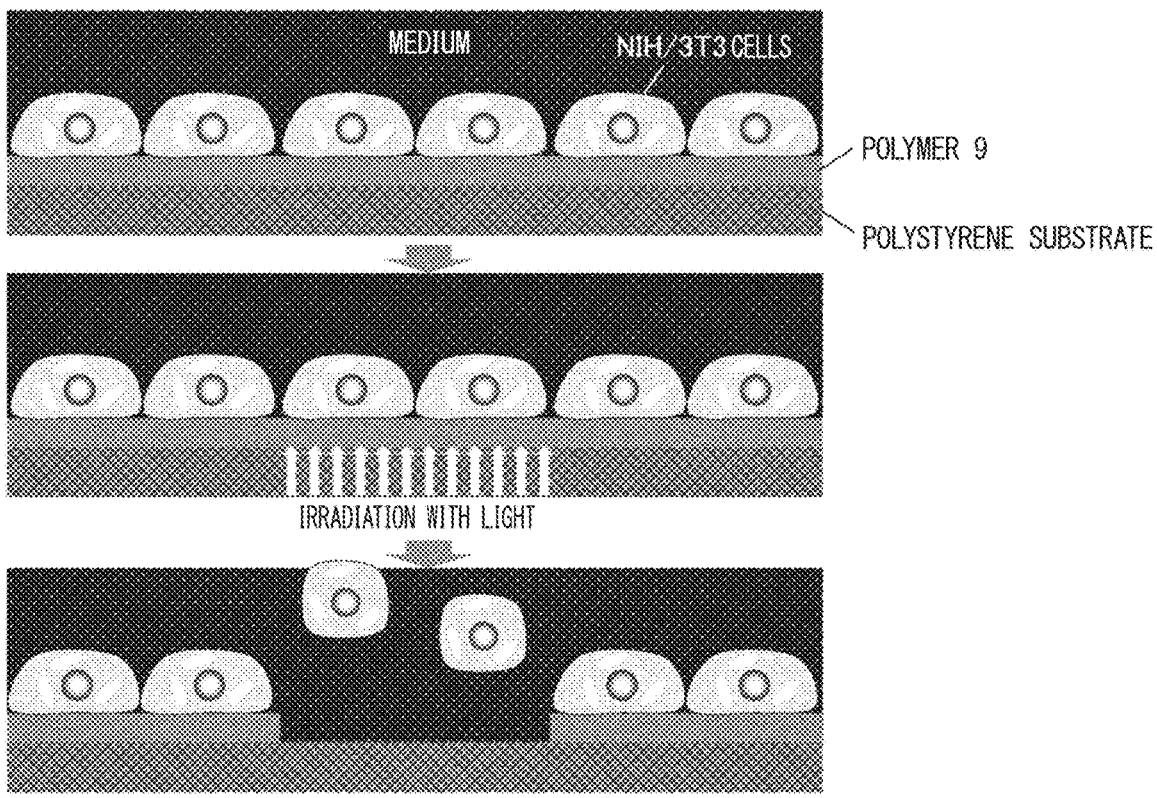
FIG. 16(a) is a schematic diagram for describing light-responsive peeling of Example 25.
FIG. 16(b) is an image of a bottom surface of a composite material after the light-responsive peeling.
Figure 16:
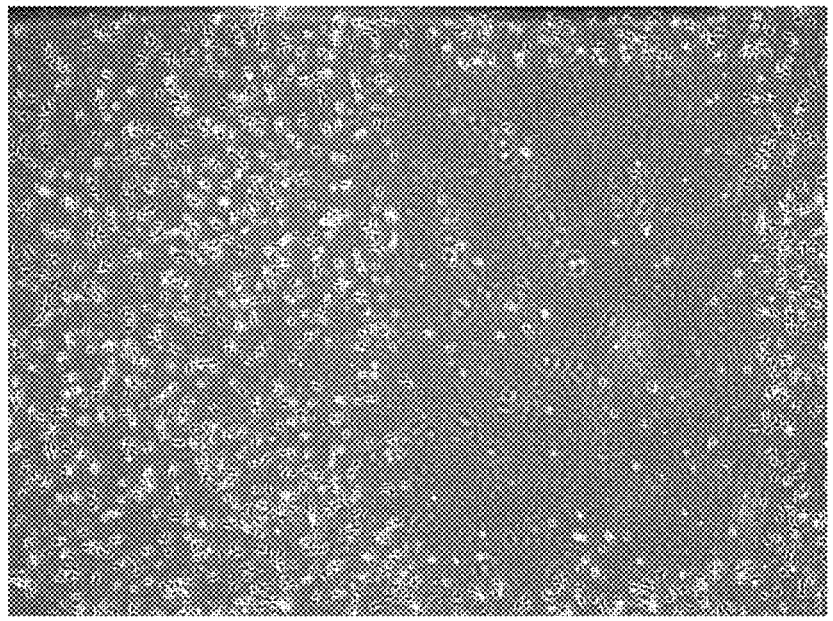

A solution of Polymer 9 shown in FIG. 12 in 1% TFE was spin-coated on a polystyrene substrate and heated at 85° C. for 2 hours to obtain a composite material. NIH/3T3 cells dispersed in a medium were seeded on this composite material. In a case of being cultured for half a day, as shown in FIG. 16(a), the cells adhered and spread over the entire surface of a Polymer 9 layer. Polymer 9 was locally irradiated with light having a wavelength of 365 nm and an intensity of 120 mW/cm$^2$ for 1 minute from a polystyrene substrate side of the composite material. As a result, in a region which had been irradiated with light, the spread cells were changed to a round shape. After 1 hour, in a case where a medium is gently sprayed over the entire surface of the composite material, the cells were peeled off from Polymer 9 in a region which had been irradiated with light.

Example 26: Light-Responsive Dissolution of Compound 12 (x=25, y=0, z=75)

Figure 17:
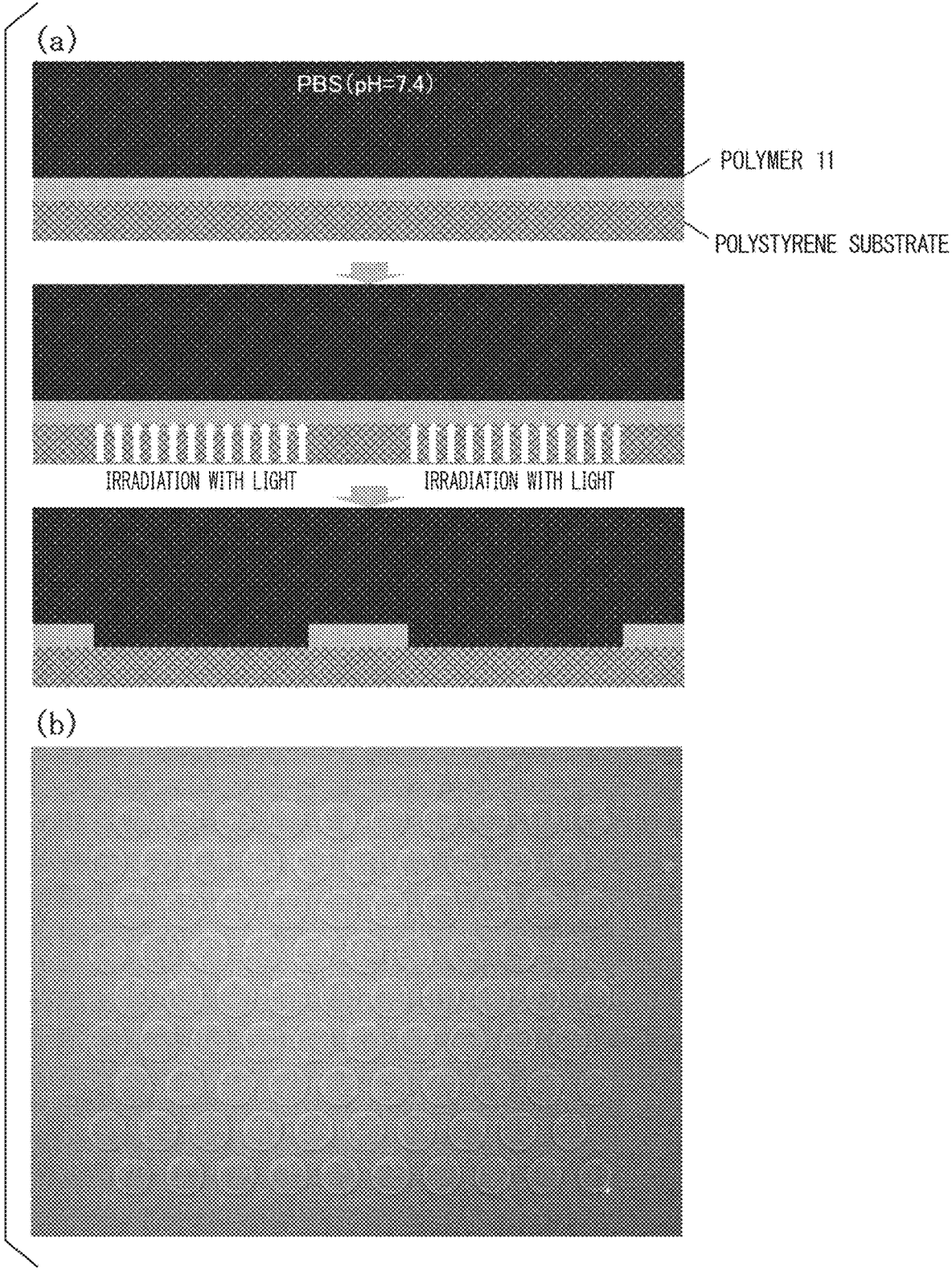
FIG. 17(a) is a schematic diagram for describing light-responsive dissolution of Example 26.
FIG. 17(b) is an image of a bottom surface of a composite material after the light-responsive dissolution.

Polymer 11 (Compound 12 in which x=25, y=0, z=75) shown in FIG. 12 was prepared in the same manner as in Example 12. A TFE solution containing 1.5% of Polymer 11 was spin-coated on a polystyrene substrate and heated at 85° C. for 2.5 hours to obtain a composite material. As shown in FIG. 17(a), in a case where Polymer 11 was irradiated with light having a wavelength of 365 nm and an intensity of 120 mW/cm$^2$ in a dot shape of a predetermined pattern for 2 seconds from a polystyrene substrate side of the composite material in PBS, Polymer 11 in a region which had been irradiated with light was dissolved in PBS.

Example 27: Light-Responsive Peeling of Compound 12 (x=25, y=0, z=75) and Cells

Figure 18:
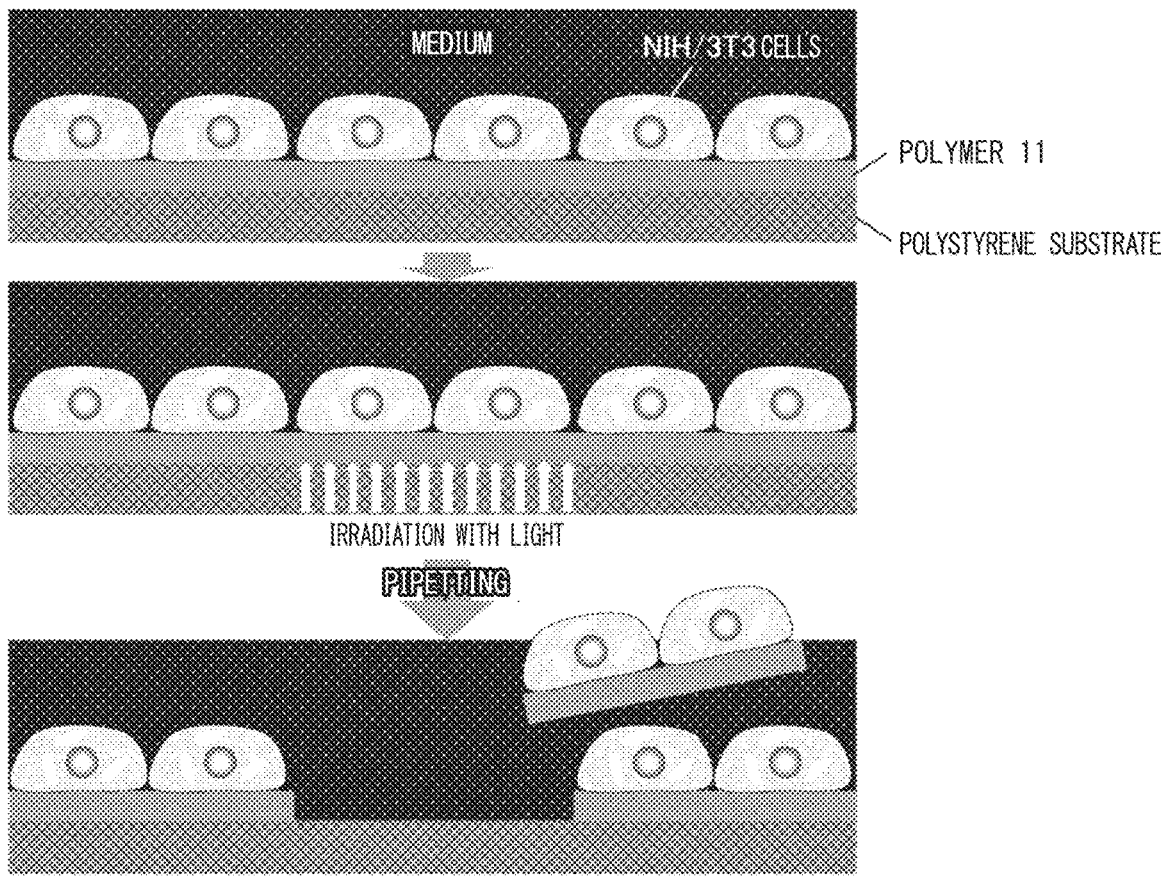
FIG. 18(a) is a schematic diagram for describing light-responsive peeling of Example 27.
FIG. 18(b) is an image of a bottom surface of a composite material after the light-responsive peeling.
Figure 18:
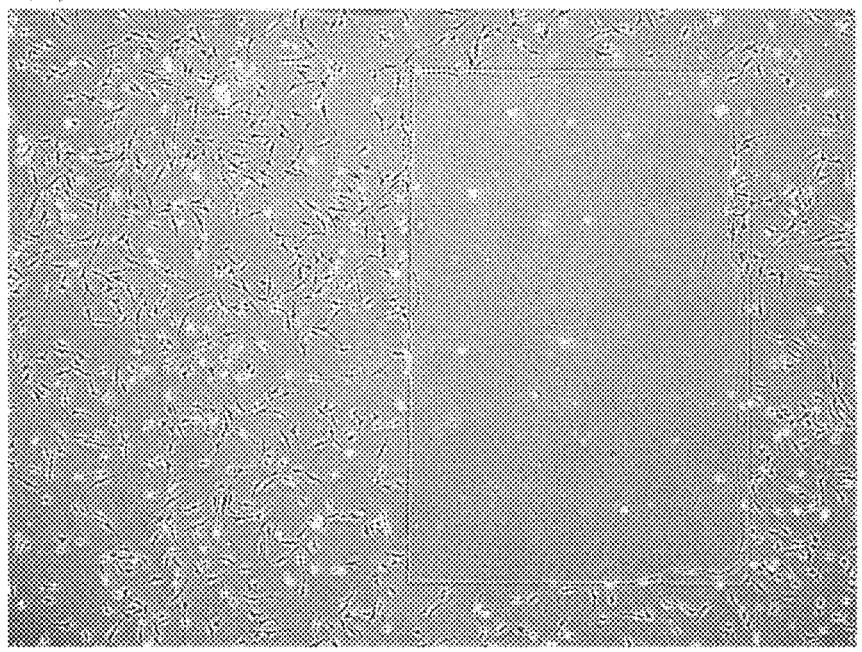

A TFE solution containing 1.5% of Polymer 11 was spin-coated on a polystyrene substrate and heated at 85° C. for 2.5 hours to obtain a composite material. NIH/3T3 cells dispersed in a medium were seeded on this composite material. In a case of being cultured for half a day, as shown in FIG. 18(a), the cells adhered and spread over the entire surface of a Polymer 11 layer. Polymer 11 was irradiated with light having a wavelength of 365 nm and an intensity of 66 mW/cm$^2$ in a local rectangular shape for 10 seconds from a polystyrene substrate side of the composite material. After 30 minutes, in a case where a medium was gently sprayed over the entire surface of the composite material, the cells and Polymer 11 were peeled off in a state of being integrated with each other from the polystyrene substrate in a region which had been irradiated with light.

Example 28: Temperature Dependency of Turbidity of Compound 12 (x=10, y=0, z=90 and x=4, y=0, z=96)

Figure 19:
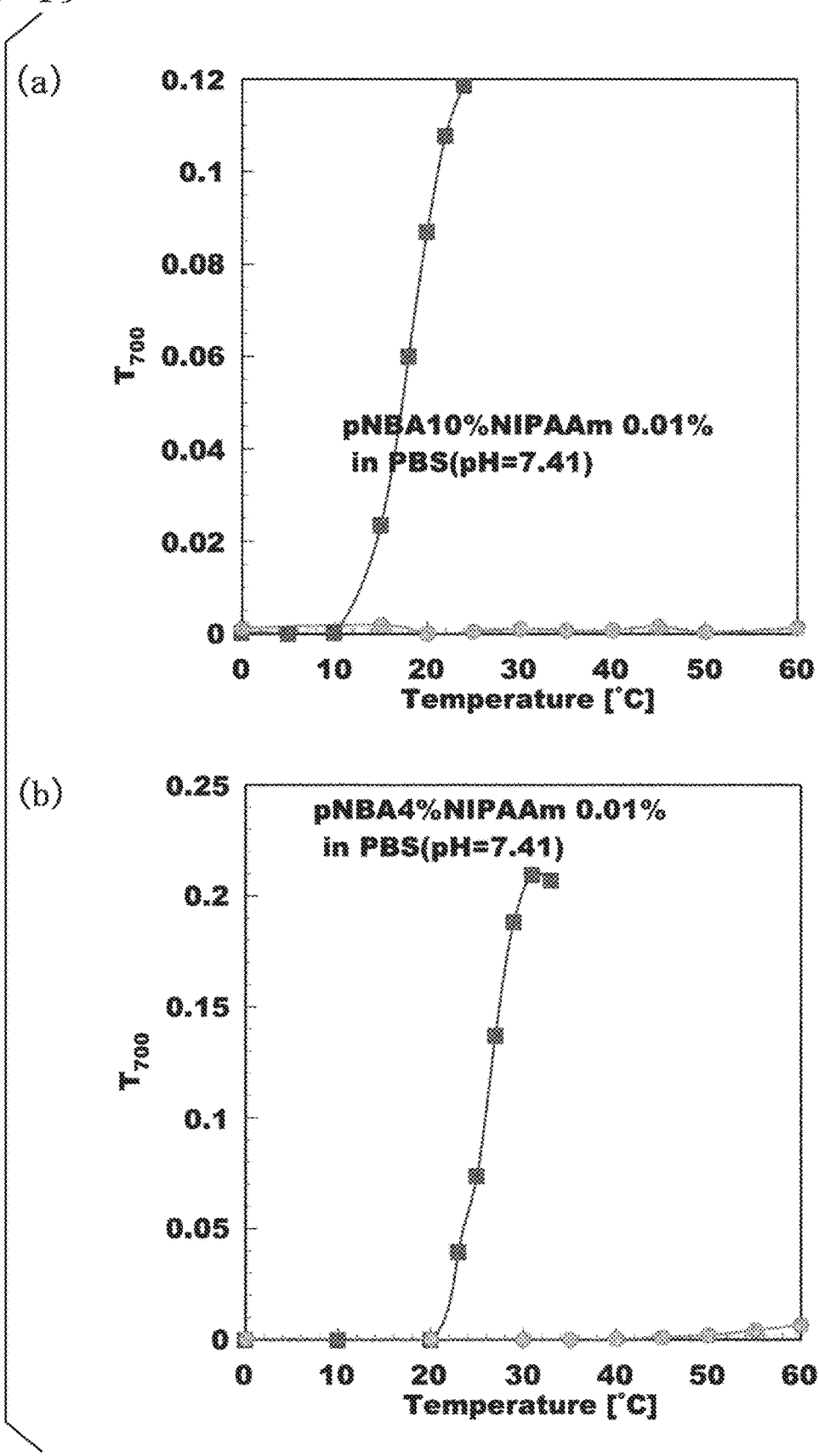
FIG. 19(a) and FIG. 19(b) are a graph relating to Polymer 12 and a graph relating to Polymer 14, respectively, for temperature dependency of turbidity at a wavelength of 700 nm of an aqueous solution of a polymer compound of the present embodiment.

Polymer 12 (Compound 12 in which x=10, y=0, z=90) and Polymer 14 (Compound 12 in which x=4, y=0, z=96) shown in FIG. 12 were prepared in the same manner as in Example 12. Two types of phosphate buffer aqueous solutions (both at pH 7.41) containing 0.01% of Polymer 12 and 0.01% of Polymer 14, respectively, were prepared. Temperature dependency of turbidity (optical path length of 1 cm) of these two types of aqueous solutions at a wavelength of 700 nm was measured before and after irradiation with ultraviolet light having a wavelength of 365 nm. Each aqueous solution after irradiation with ultraviolet light was an aqueous solution which had been irradiated with a sufficient amount of ultraviolet light. The results are shown in FIG. 19. Turbidity before irradiation with ultraviolet light is indicated by ■ and turbidity after irradiation with ultraviolet light is indicated by ○.

Lower critical solution temperatures (LCST) of the aqueous solution of Polymer 12 and the aqueous solution of Polymer 14 before irradiation with ultraviolet light were 10° C. and 20° C., respectively. LCST is a temperature at or below which a polymer is dissolved. On the other hand, in the aqueous solution of Polymer 12 and the aqueous solution of Polymer 14 after irradiation with ultraviolet light, LCST was not observed in a temperature range of 60° C. or less measured. From this, it can be confirmed that at pH 7.41, Polymer 12 is changed from a water-insoluble state to a water-soluble state by irradiation with ultraviolet light at least in a range of 10° C. to 60° C., and Polymer 14 is changed from a water-insoluble state to a water-soluble state by irradiation with ultraviolet light at least in a range of 20° C. to 60° C.

Example 29: Light-Responsive Peeling of Compound 12 (x=10, y=0, z=90) and Cells

Figure 20:
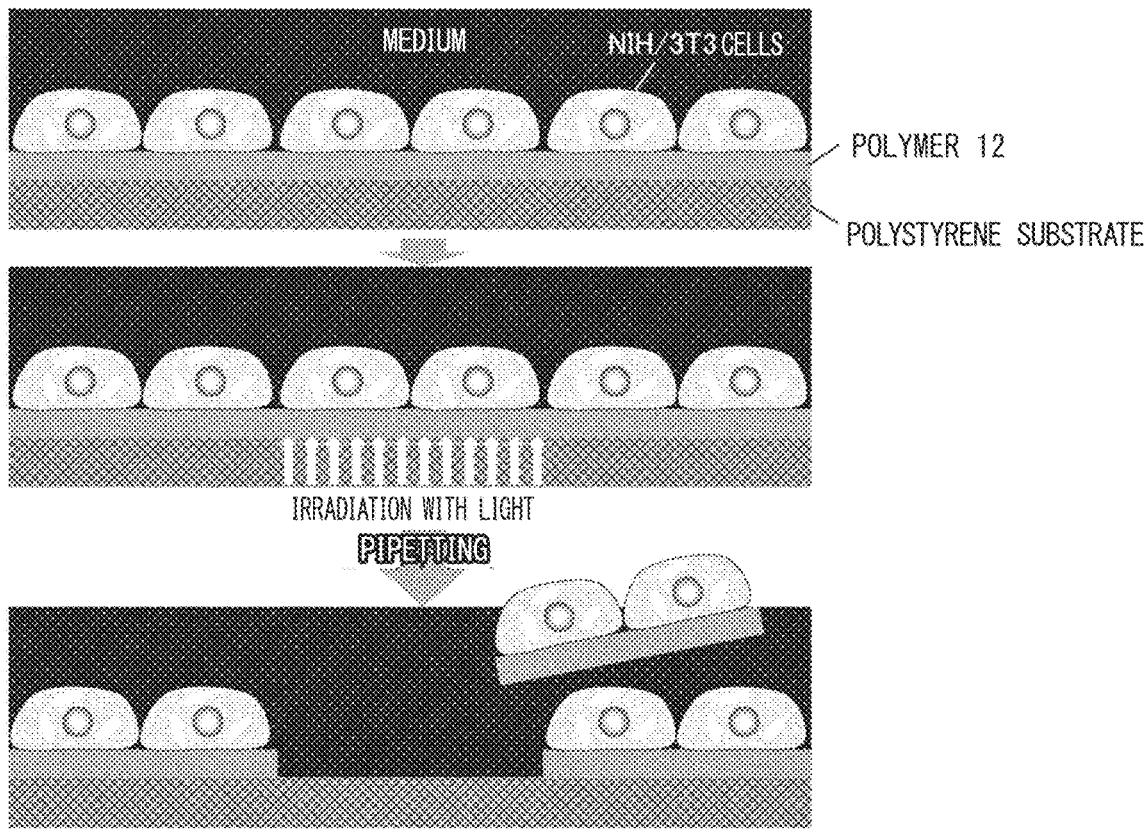
FIG. 20(a) is a schematic diagram for describing light-responsive peeling of Example 29.
FIG. 20(b) is an image of a bottom surface of a composite material before irradiation with ultraviolet light.
FIG. 20(c) is an image of the bottom surface of the composite material during irradiation with ultraviolet light.
FIG. 20(d) is an image of the bottom surface of the composite material immediately after irradiation with ultraviolet light.
FIG. 20(e) is an image of the bottom surface of the composite material after spraying with a medium.
Figure 20:
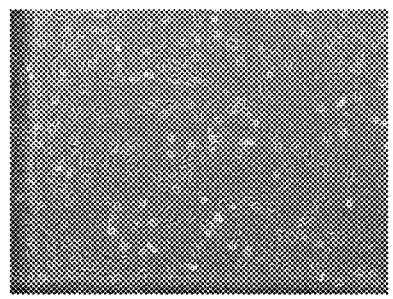
Figure 20:
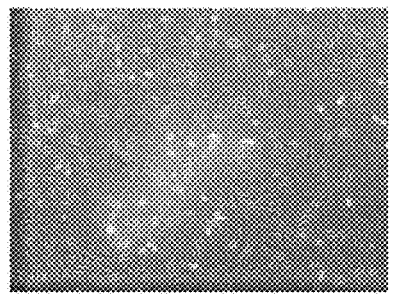
Figure 20:
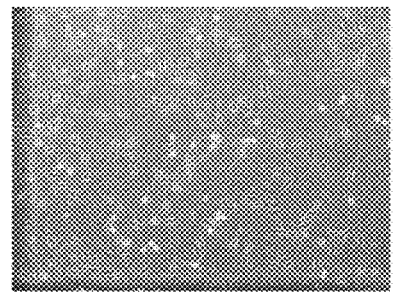
Figure 20:
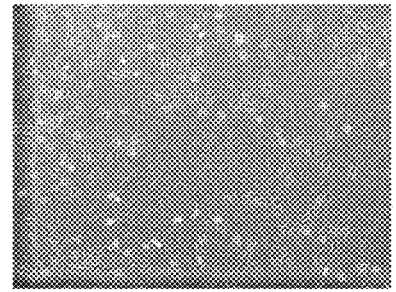

A mixed solution of 88% of a TFE solution containing 0.9% of Polymer 12 and 12% of n-BuOH was spin-coated on a polystyrene substrate and heated at 85° C. for 2 hours to obtain a composite material. After immersing this composite material in water at 37° C. for 1 hour, NIH/3T3 cells dispersed in a medium were seeded on this composite material. In a case of being cultured for half a day, as shown in FIG. 20(a), the cells adhered and spread over the entire surface of a Polymer 12 layer.

Then, a part of the cells was irradiated with light having a wavelength of 365 nm and an intensity of 120 mW/cm$^2$ for 3 seconds from a polystyrene substrate side of the composite material. Immediately after irradiation, in a case where a medium was gently sprayed over the entire surface of the composite material, the cells that adhered and spread only in a region which had been irradiated with light could be peeled off in a state of being integrated with Polymer 12 from the polystyrene substrate and recovered. A large number of cells were recovered under the same conditions and stained with trypan blue. As a result, 98% of the cells recovered from the region which had been irradiated with light survived.

Figure 21:
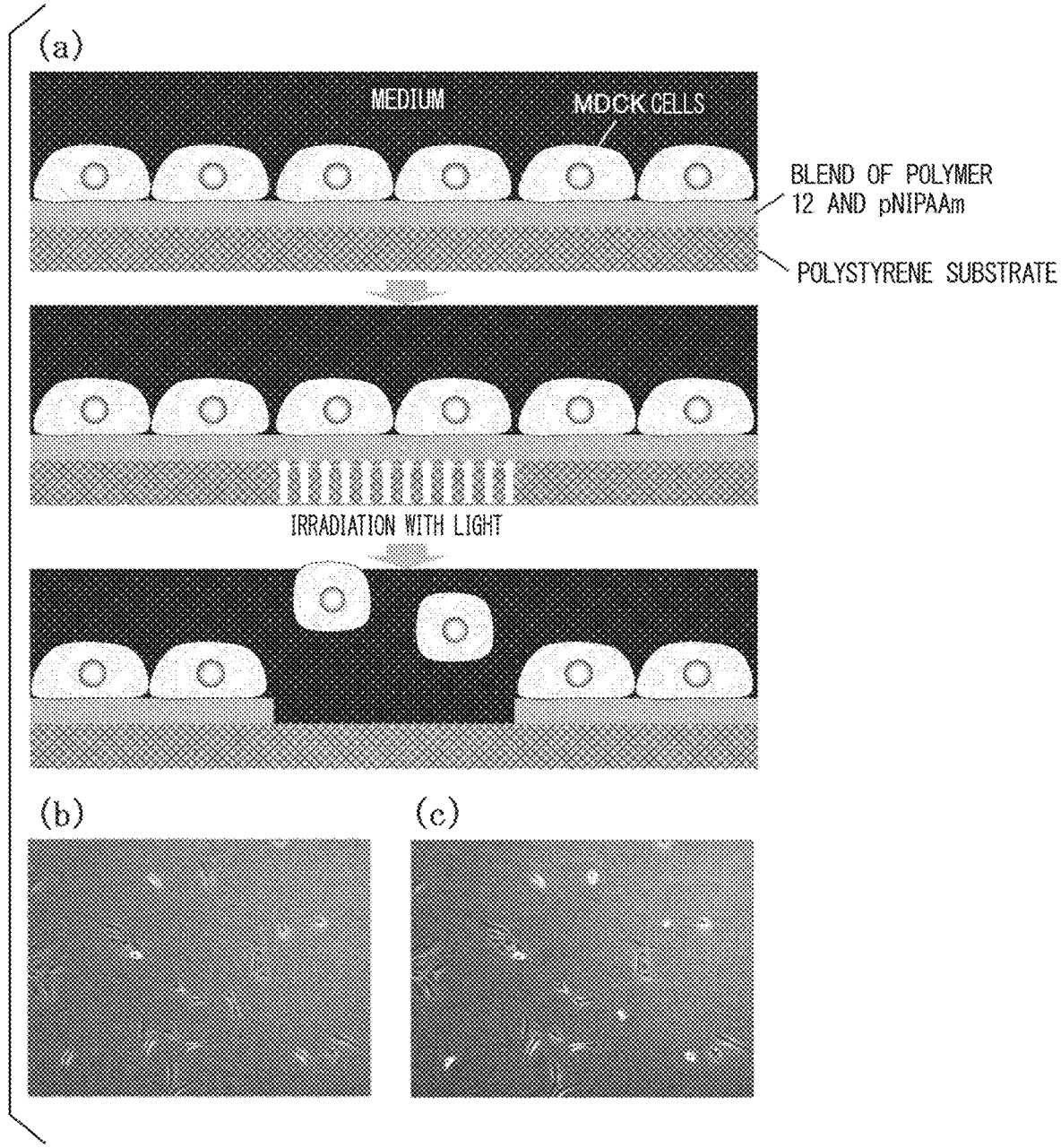
FIG. 21(a) is a schematic diagram for describing light-responsive peeling of Example 30.

Example 30: Light-Responsive Peeling of Cells from Composite Layer of Compound 12 (x=10, y=0, z=90) and pNIPAAm A TFE solution containing 0.91% of Polymer 12 and 0.36% of unmodified Poly(N-isopropylacrylamide) (pNIPAAm) was spin-coated on a polystyrene substrate and heated at 85° C. for 2.5 hours to obtain a composite material with a composite layer of Polymer 12 and pNIPAAm provided on a surface thereof. MDCK cells were dispersed in a medium and seeded on this composite material. In a case of being cultured for half a day, as shown in FIG. 21(a), the cells adhered and spread over the entire surface of this composite layer. A part of the cells on the composite material was irradiated with light having a wavelength of 365 nm and an intensity of 120 mW/cm$^2$ for 3 seconds from a polystyrene substrate side. In a region which had been irradiated with light, the composite layer was dissolved in the medium, and cells that adhered and spread on the dissolved composite layer were individually peeled off. It was demonstrated that manipulation can be carried out on a cell by cell basis using the polymer compound of the present invention.

Example 31: Light-Responsive Peeling of Composite Layer of Compound 12 (x=10, y=0, z=90) and pNIPAAm, and Cell Colony A mixed solution of 91% of a TFE solution containing 1.5% of Polymer 12 and 0.44% of unmodified pNIPAAm, and 9% of n-BuOH was spin-coated on a polystyrene substrate and heated at 85° C. for 2 hours to obtain a composite material with a composite layer of Polymer 12 and pNIPAAm provided on a surface thereof. In a state where a temperature was kept at room temperature, the surface of the composite material was coated with a membrane regulator (Matrigel, Corning Incorporated) and agglomerates of human iPS cells were further seeded thereon.

Figure 22:
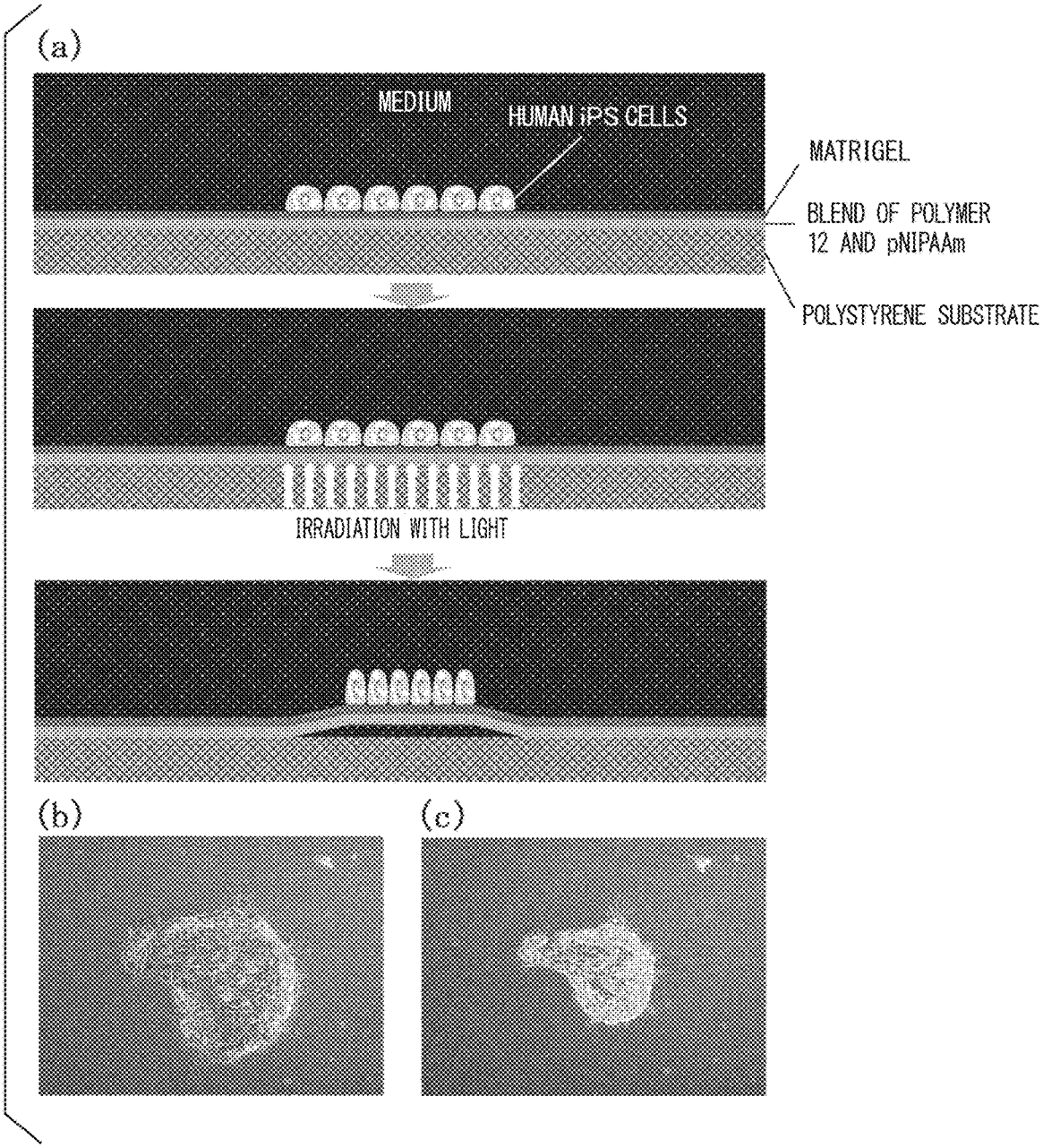
FIG. 22(a) is a schematic diagram for describing light-responsive peeling of Example 31.
FIG. 22(b) is an image of an iPS cell colony on a composite material before irradiation with ultraviolet light.
FIG. 22(c) is an image of the iPS cell colony on the composite material after irradiation with ultraviolet light.

In a case of being cultured for 2 days, colonies of human iPS cells adhered and spread on the entire surface of the composite material. A region of the composite layer to which one of the colonies was adhered was irradiated with light having a wavelength of 365 nm and an intensity of 120 mW/cm$^2$ for 3 seconds from a polystyrene substrate side. As shown in FIG. 22(a), in a region which had been irradiated with light, the composite layer was peeled off from the polystyrene substrate, and the colony that had adhered and spread shrunk significantly.

Example 32: Light-Responsive Peeling of Compound 12 (x=7, y=0, z=93) and Cell Colony Polymer 13 (Compound 12 in which x=7, y=0, z=93) shown in FIG. 12 was prepared in the same manner as in Example 12. A solution of Polymer 13 in 0.88% TFE was spin-coated on a polystyrene substrate and heated at 85° C. for 2.5 hours to obtain a composite material. In a state where a temperature was kept at room temperature, the surface of the composite material was coated with a membrane regulator (Matrigel, Corning Incorporated) and agglomerates of human iPS cells were further seeded thereon.

Figure 23:
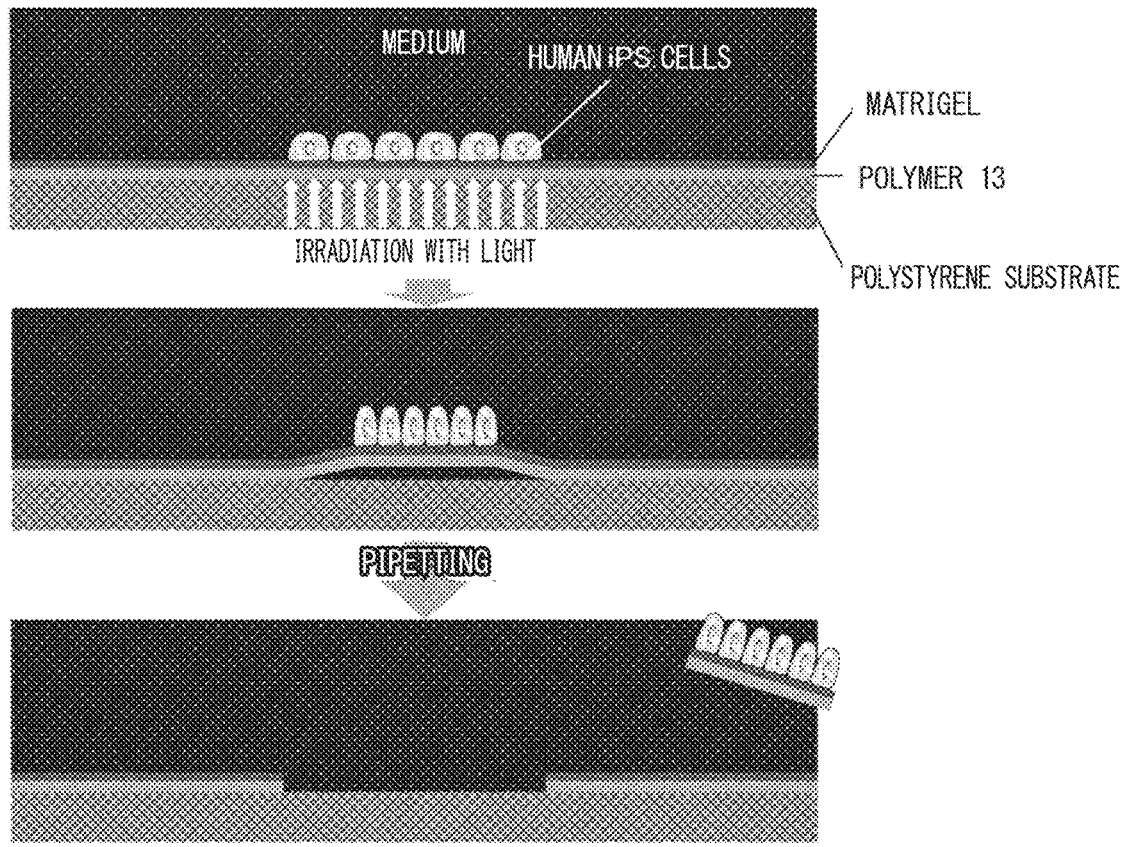
FIG. 23(a) is a schematic diagram for describing light-responsive peeling in Example 32.
FIG. 23(b) is an image of an iPS cell colony on a composite material before irradiation with ultraviolet light.
FIG. 23(c) is an image of the iPS cell colony on the composite material during irradiation with ultraviolet light.
FIG. 23(d) is an image of the iPS cell colony on the composite material immediately after irradiation with ultraviolet light.
FIG. 23(e) is an image of the iPS cell colony after irradiation with ultraviolet light and after spraying a medium onto the composite material.
Figure 23:
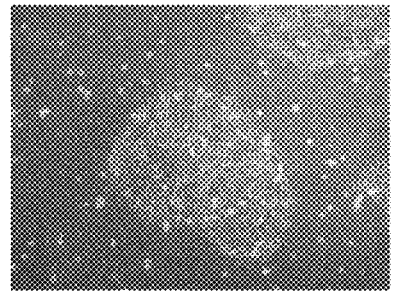
Figure 23:
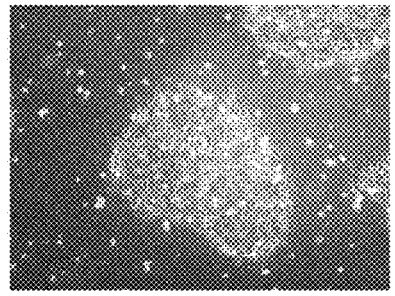
Figure 23:
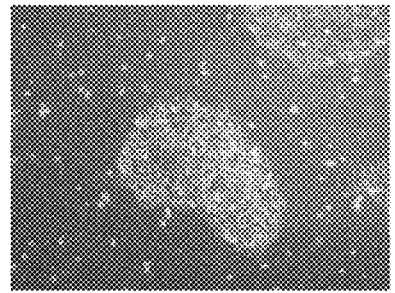
Figure 23:
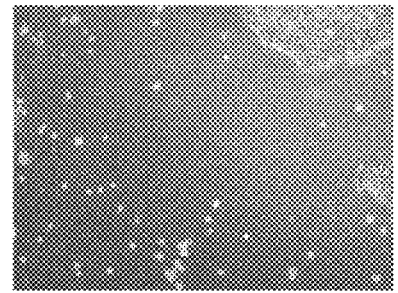

In a case of being cultured for 6 days, colonies of human iPS cells adhered and spread on the entire surface of the composite material. A region of Polymer 13 to which one of the colonies was adhered was irradiated with light having a wavelength of 365 nm and an intensity of 120 mW/cm$^2$ for 3 seconds from a polystyrene substrate side. As shown in FIG. 23(a), in a region which had been irradiated with light, a Polymer 13 layer was peeled off from the polystyrene substrate, and the colony that had adhered and spread shrunk significantly. Furthermore, in a case where a medium was gently sprayed on a surface of the composite material, the colony that had adhered and spread and Polymer 13 were separated and removed, in a state of being integrated with each other, from the polystyrene substrate.

Figure 24:
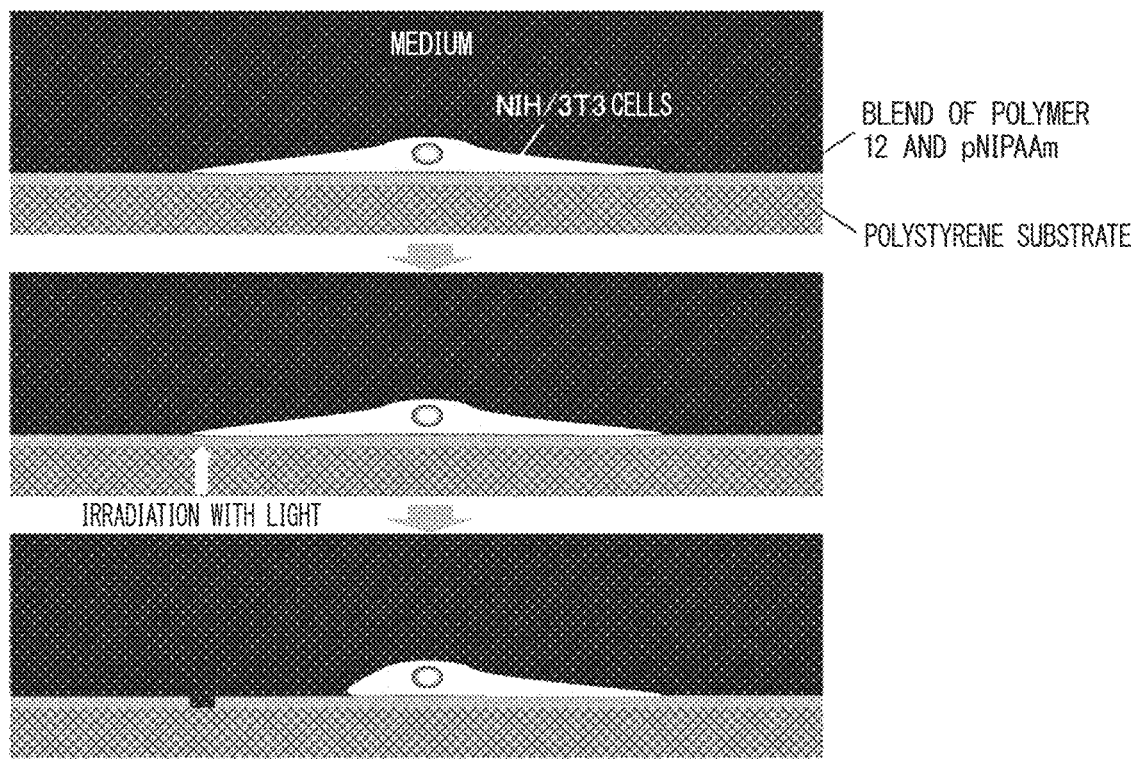
FIG. 24(a) is a schematic diagram for describing light-responsive peeling of Example 33.
FIG. 24(b) is an image of cells on a composite material before irradiation with ultraviolet light.
FIG. 24(c) is an image of the cells on the composite material after irradiation with ultraviolet light.
Figure 24:
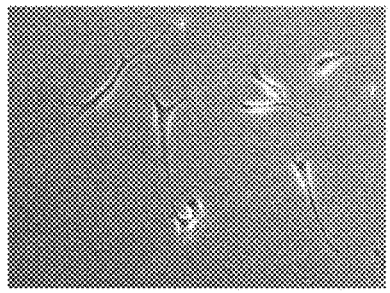
Figure 24:
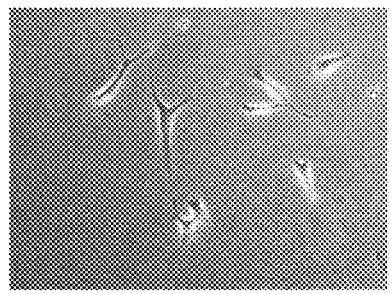

Example 33: Selective Light-Responsive Peeling of Intracellular Specific Site from Composite Layer of Compound 12 (x=10, y=0, z=90) and pNIPAAm A TFE solution containing 0.81% of Polymer 12 and 0.56% of unmodified pNIPAAm was spin-coated on a polystyrene substrate and heated at 85° C. for 2.5 hours to obtain a composite material with a composite layer of Polymer 12 and pNIPAAm provided on a surface thereof. NIH/3T3 cells dispersed in a medium were seeded on this composite material. In a case of being cultured for half a day, as shown in FIG. 24(a), the cells adhered and spread over the entire surface of this composite layer. A region of the composite layer where tips of pseudopodia of some cells were present was irradiated with light having a wavelength of 365 nm and an intensity of 120 mW/cm$^2$ for 3 seconds from a polystyrene substrate side. The tips of pseudopodia were dislocated from only a surface of the composite layer in a region which had been irradiated with light, and the pseudopodia shrank. It was demonstrated that a specific site of an individual cell can be manipulated independently using the polymer compound of the present invention.

Example 34: Synthesis of Compound 15 and Compound 16 (Reaction Scheme (XIV))

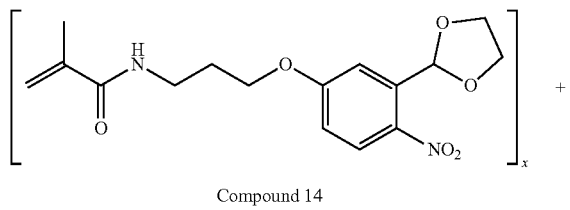

Compound 14

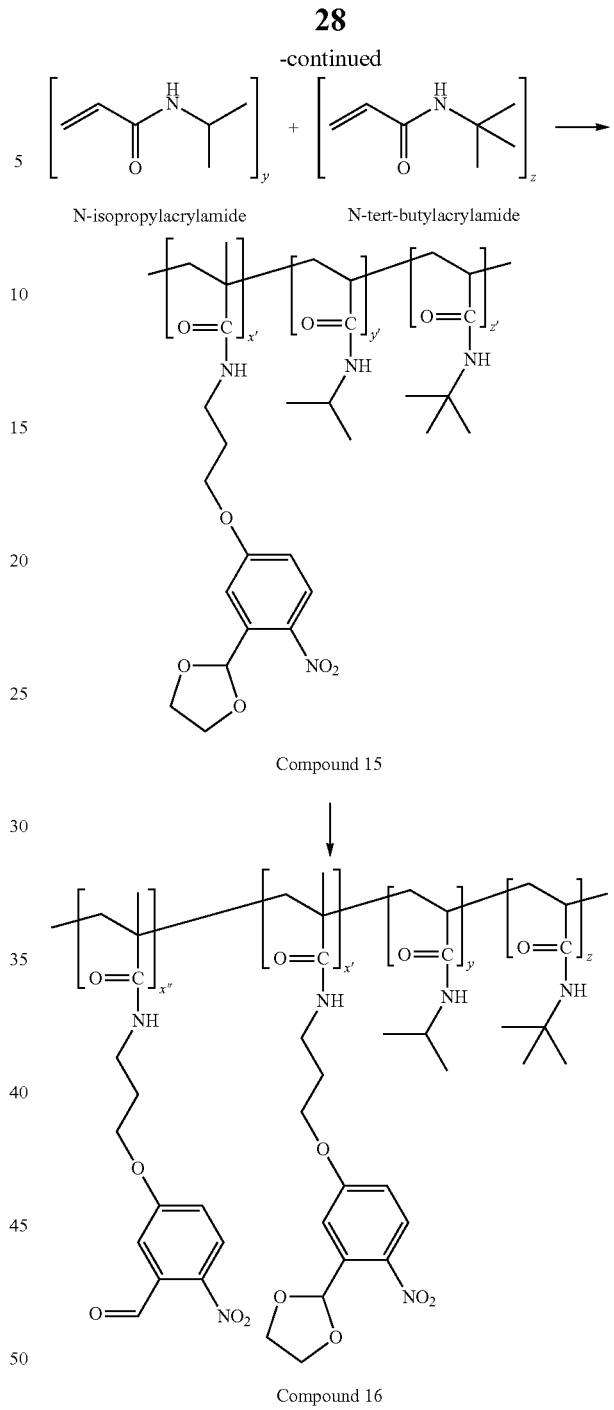

NBA polymers (Compound 15 and Compound 16) containing N-tert-butylacrylamide (NTBAAm) were synthesized as follows using Compound 14 which is a polymerizable monomer having an NBA group as a moderately hydrophobic monomer component. First, an anhydrous tetrahydrofuran solution containing Compound 14:N-isopropylacrylamide:N-tert-butylacrylamide:azoisobutyronitrile as a raw material molar ratio (x:y:z:AIBN) shown in Table 1 was stirred at 65° C. for a whole day and night under a nitrogen stream. After cooling, the precipitate generated by being added dropwise to ether was reprecipitated using a tetrahydrofuran-ether solution to obtain Compound 15.

TABLE 1

| Example | Raw material molar ratio x:y:z: AIBN | Yield amount (g) | Yield (%) | Compound 15 Compositional ratio (x': y' + z') | Compound 16 Deprotection rate (%) | Reaction condition for deprotection |
|---|---|---|---|---|---|---|
| 34-1 | 4:76:20:1 | 1.36 | 54 | 4:96 | 100 | 2N HCl/CHCl$_3$ |
| 34-2-1 | 10:40:50:1 | 1.22 | 43 | 12:88 | 79 | 2N HCl/CHCl$_3$ |
| 34-2-2 | | | | | 84 | 6N HCl/CHCl$_3$ |
| 34-2-3 | | | | | 100 | 2N HCl/THF |
| 34-2-4 | | | | | 100 | 6N HCl/THF |
| 34-2-5 | | | | | 100 | 2N HCl/dioxane |
| 34-3 | 10:70:20:1 | 1.22 | 44 | 11:89 | 100 | 2N HCl/CHCl$_3$ |
| 34-4 | 15:65:20:1 | 0.35 | 24 | 18:82 | 82 | 2N HCl/CHCl$_3$ |
| 34-5 | 10:0:90:1 | 0.15 | 5 | 12:88 | 86 | 2N HCl/CHCl$_3$ |
| 34-6 | 0:10:90:1 | 1.85 | 80 | 16:84 | — | |

A compositional ratio of Compound 15 was estimated from an integrated value of peaks derived from an aromatic, an NH group, and a hydrogen atom at a benzyl position appearing at around 6 to 8 ppm, and other peaks appearing at around 1 to 4 ppm in a $^1$H-NMR (CDCl$_3$) spectrum. In Example 34-6, a compositional ratio of Compound 15 was estimated based on a methine hydrogen peak (4 ppm) of an isopropyl group of N-isopropylacrylamide.

Hydrochloric acid was added to a chloroform solution of Compound 15, tetrahydrofuran, or 1,4-dioxane, and the mixture was stirred at 60° C. for 3 days. The precipitate generated by dilution with ether was reprecipitated with tetrahydrofuran-ether to obtain Compound 16. A deprotection rate of Compound 16 was set as 100% in a case of confirming disappearance of a peak derived from acetal which had protected an aldehyde group appearing at 4 ppm, and the presence of a single peak derived from an aromatic appearing at around 7 to 8 ppm in $^1$H-NMR (CDCl$_3$ or CD$_3$COCD$_3$) spectrum. On the other hand, in a case of confirming two types of peaks which are derived from acetal which has protected an aldehyde group appearing at 4 ppm and peaks derived from an aromatic appearing at around 7 to 8 ppm, the deprotection rate of Compound 16 was estimated based on a peak derived from an aldehyde group appearing at around 11 ppm.

Figure 25:
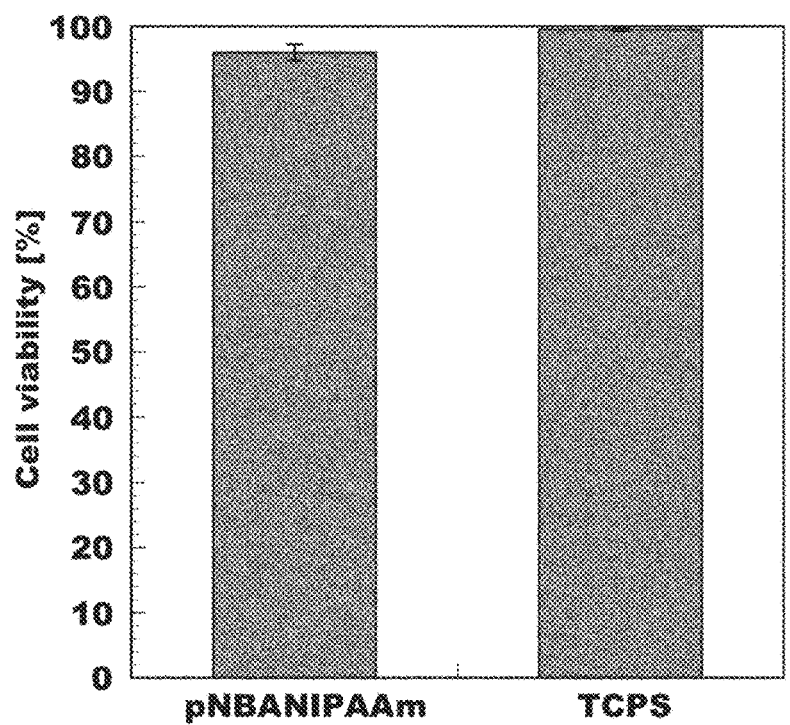
FIG. 25 is a graph showing survival rates of cells recovered by light-responsive peeling and by ordinary enzymatic peeling from a pNBANIPAAm-coated layer.

Example 35: Survival Rate of Cells Recovered by Light-Responsive Peeling from pNBANIPAAm-Coated Layer PNIPAAm (Compound 14 in FIG. 12. Hereinafter, pNI-PAAm having an NBA group introduced through an ether group is referred to as "pNBANIPAAm" in some cases) which had been modified with an NBA group at an introduction rate of 4 mol % via an ether group was coated on a substrate. NIH/3T3 cells were seeded on the coated layer and cultured at 37° C. for 2 days. Then, light having a center wavelength of 365 nm and an intensity of 40 mW/cm$^2$ was irradiated from a bottom side of the substrate for 10 seconds, and a medium was gently sprayed on a surface to recover the cells. After carrying out dispersion to a single cell with a phosphate buffer solution at pH 7.4 containing 1 mM EDTA, staining with trypan blue was carried out. The numbers of stained cells and non-stained cells were counted, and a survival rate of the NIH/3T3 cells was quoted 96% (left of the graph in FIG. 25).

In addition, a survival rate of NIH/3T3 cells which were recovered after 0.05 w/v % trypsin-0.53 mM EDTA solution was allowed to act on a common culture dish at 37° C. for 2 minutes was quoted in the same manner. As a result, the survival rate was 98% (right of the graph in FIG. 25). It was found that there was almost no difference between the survival rate of the cells peeled by light-responsive dissolution of pNBANIPAAm and a survival rate of cells recovered by an ordinary enzymatic peeling.

Example 36: Light-Responsive pH Changes in NBA Copolymer Aqueous Solution

Figure 26:
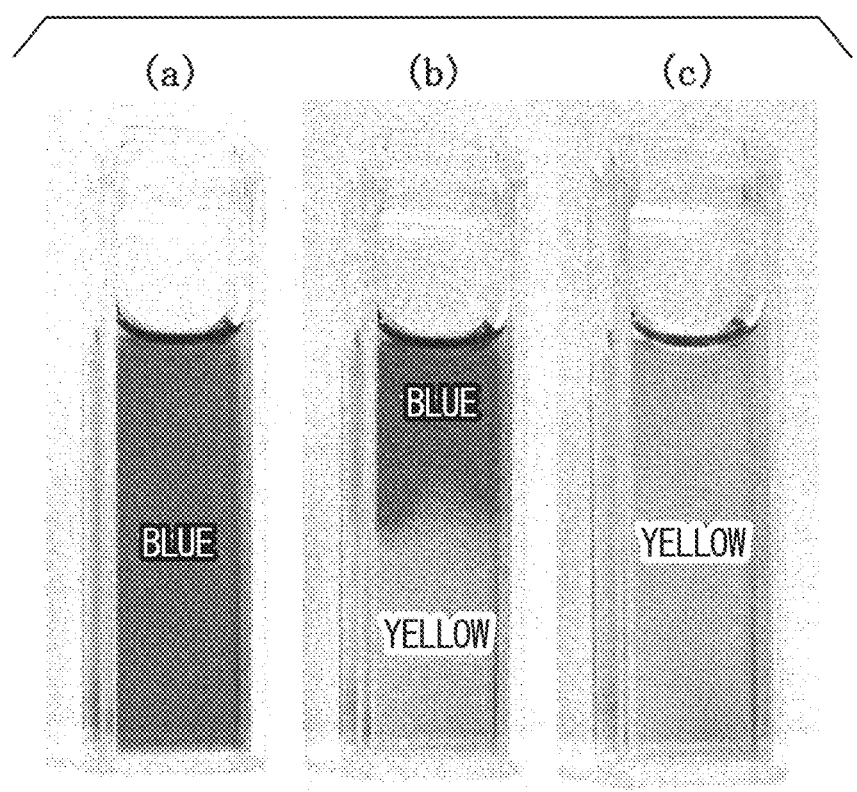

In a tetrahedral transmission optical cell (cuvette) having an optical path length of 1 cm, a trace amount of BTB was added to a 0.01% aqueous solution of pNBANIPAAm having an introduction rate of NBA group of 10 mol %. About 1% of a 0.01 N NaOH aqueous solution was further added to prepare a weakly basic blue aqueous solution as shown in FIG. 26(a). Then, a lower half of the aqueous solution in the cuvette was irradiated with ultraviolet light having a center wavelength of 365 nm. As shown in FIG. 26(b), the aqueous solution was rapidly changed to yellow in a region which had been irradiated with light.

Furthermore, in a case where the entire aqueous solution was irradiated with light, the whole inside of the cuvette was changed to yellow as shown in FIG. 26(c). In other words, irradiation with light caused decreased pH in the aqueous solution. From this result, it was found that photoreaction of an NBA group at a polymer side chain produces an o-nitrosobenzoic acid group which is a weak acid and releases a proton so that a pH is decreased, and such a release of a proton ionizes the polymer.

Example 37: pH Dependency of Light-Responsive Dehydration Properties

A 1% aqueous solution of pNBANIPAAm having an introduction rate of NBA group of 10 mol %, and buffer solutions or hydrochloric acid aqueous solutions at various pH were mixed in a cuvette so as to be 0.01% aqueous solutions of pNBANIPAAm. While gradually increasing a temperature of the aqueous solution from 0° C. to 60° C., an optical density of the aqueous solution at which absorbance of light having a wavelength of 700 nm is 0 was measured and used as turbidity. Thereafter, the aqueous solution was again cooled to 0° C., and the aqueous solution was irradiated with ultraviolet light having a center wavelength of 365 nm until a spectral change was saturated. Then, while gradually increasing the temperature of the aqueous solution, turbidity of the aqueous solution at each temperature was measured. This result is shown in FIG. 27.

Figure 27:
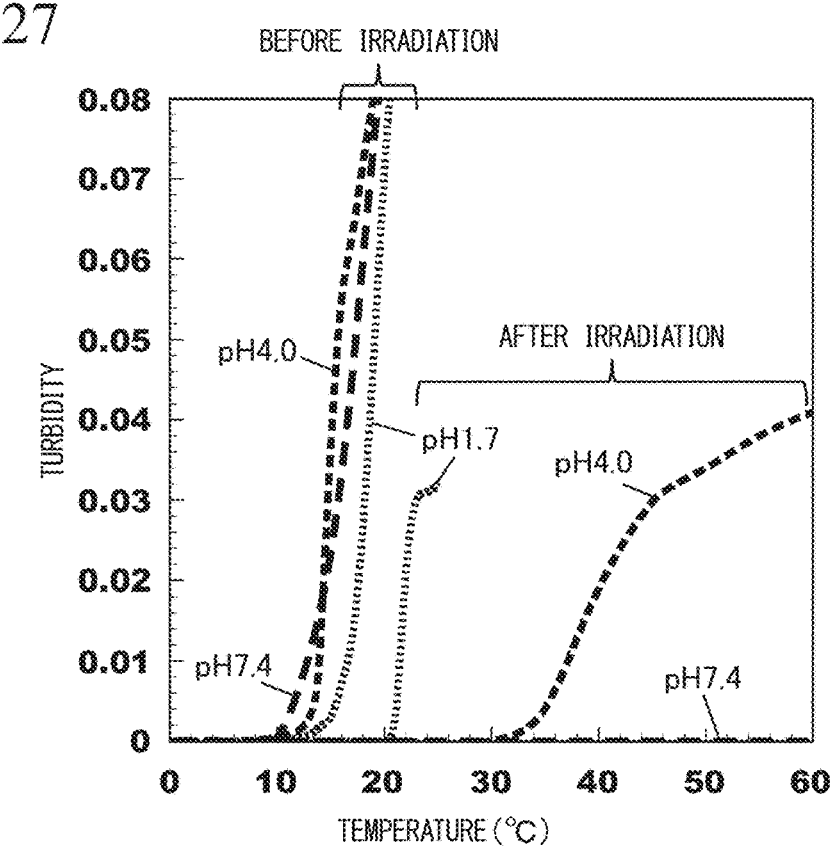
FIG. 27 is a graph showing light-responsiveness of turbidity at each temperature of a pNBANIPAAm aqueous solution which is measured under several pH conditions.

As shown in FIG. 27, at pH 1.7 to 7.4, a transition temperature (11° C. to 15° C.) of the aqueous solution before irradiation with ultraviolet light was considerably lower than a transition temperature of a pNIPAAm homopolymer aqueous solution which is 31° C. The higher the transition temperature, a higher polymer solubility is exhibited. From this result, it was found that solubility of pNIPAAm is decreased due to introduction of NBA. On the other hand, in the aqueous solution after irradiation with ultraviolet light, the transition temperature of the aqueous solution at pH 7.4 was not observed at 60° C. or lower. On the contrary, the transition temperature of the aqueous solution at pH 4.0 was observed at around 33° C., and the transition temperature of the aqueous solution at pH 1.7 was observed at around 21° C. From these results, it was shown that o-nitrosobenzoic acid, which is a weak acid, was produced due to pNBANI-PAAm being irradiated with light.

Figure 28:
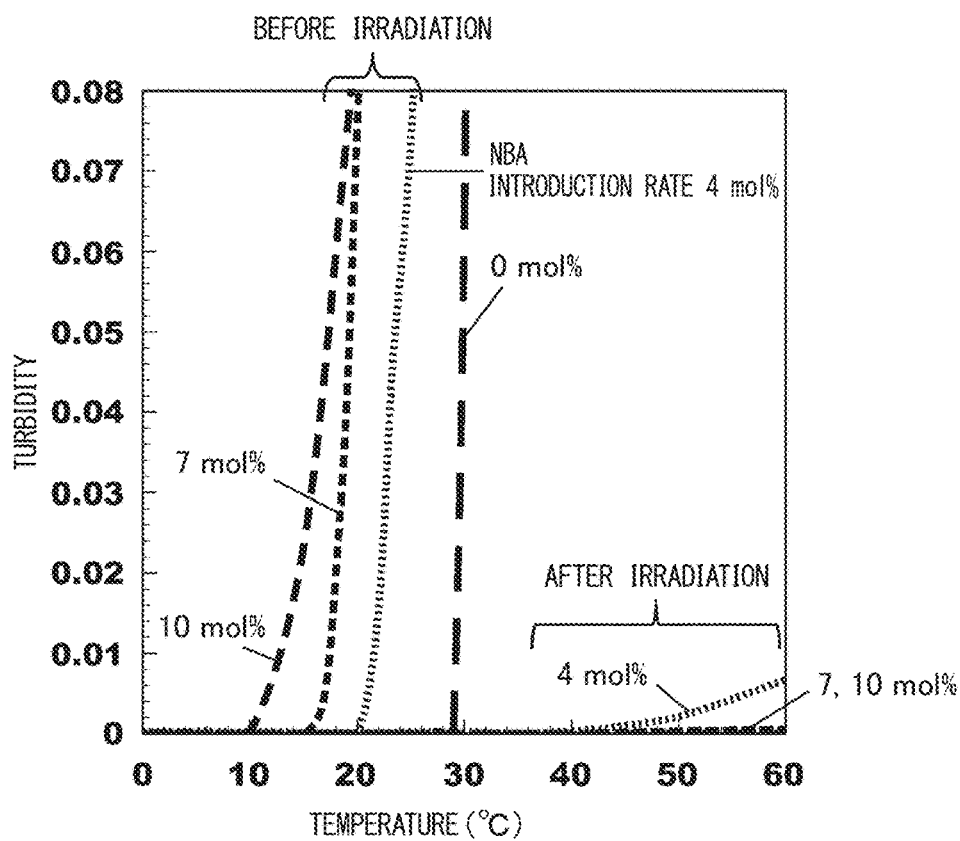
FIG. 28 is a graph showing light-responsiveness of turbidity at each temperature of a pNBANIPAAm aqueous solution which is measured under several NBA introduction rate conditions.

Example 38: Dependence of Light-Responsive Dehydration Properties on NBA Introduction Rate In the same manner as in Example 37, turbidities at 700 nm of phosphate buffer solutions at pH 7.4 containing 0.01% of four types of pNBANIPAAm having introduction rates of NBA group of 0 mol %, 4 mol %, 7 mol %, and 10 mol % were measured at 0° C. to 60° C. The result is shown in FIG. 28. As shown in FIG. 28, as the introduction rate of NBA group was increased, a transition temperature of the aqueous solution before irradiation with ultraviolet light was decreased. In other words, as the introduction rate of NBA group was increased, solubility of the polymer was decreased. On the other hand, the transition temperature after irradiation with ultraviolet light was remarkably increased as the introduction rate of NBA group was increased.

Figure 29:
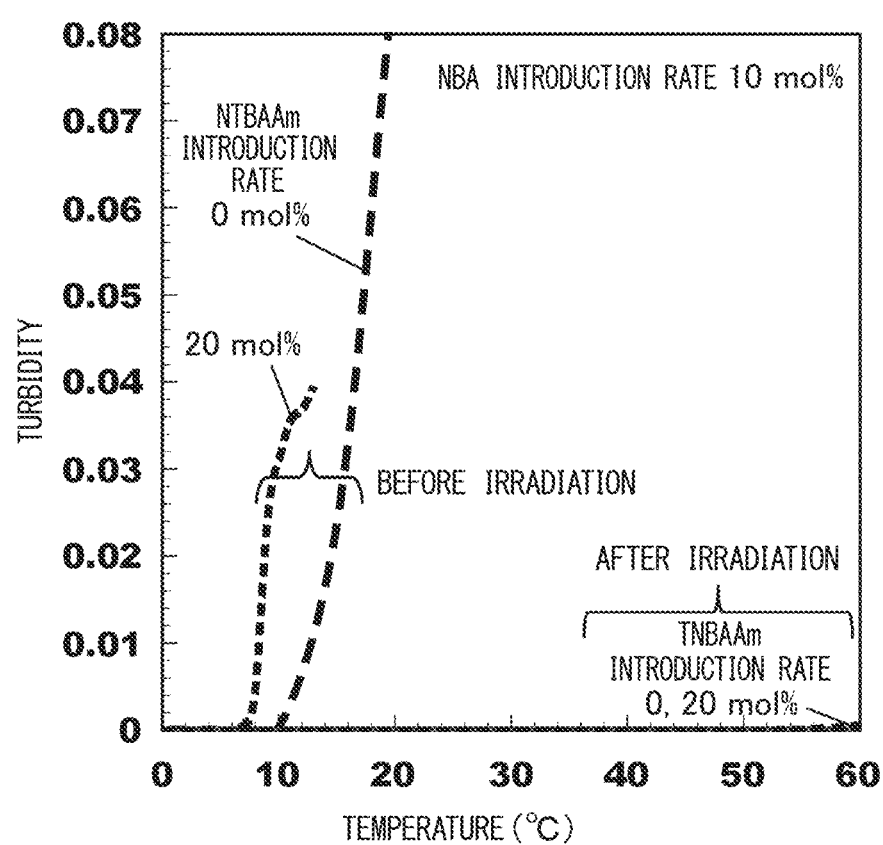
FIG. 29 is a graph showing light-responsiveness of turbidity at each temperature of a pNBANIPAAm (NBA introduction rate: 10 mol %) aqueous solution that contains 0 or 20 mol % of NTBAAm monomer component.

Example 39: Dependence of Light-Responsive Dehydration Properties on NTBAAm Introduction Rate In the same manner as in Example 37, turbidity at 700 nm of a 0.01% phosphate buffer solution (pH 7.4) of pNIPAAm containing no NTBAAm, and a 0.01% phosphate buffer solution (pH 7.4) of pNIPAAm containing 20 mol % of NTBAAm in pNBANIPAAm having an introduction rate of NBA group of 10 mol % were measured at 0° C. to 60° C. The result is shown in FIG. 29. As shown in FIG. 29, a transition temperature of the pNIPAAm aqueous solution containing NTBAAm before irradiation with ultraviolet light was lower than the transition temperature of the pNIPAAm aqueous solution not containing NTBAAm before irradiation with ultraviolet light. In other words, due to introduction of NTBAAm, dark place stability of the pNIPAAm polymer was increased. On the other hand, the transition temperature after irradiation with ultraviolet light was remarkably increased regardless of the presence or absence of NTBAAm.

Example 40: Light-Responsive Dissolution of pNBANIPAAm-Coated Film

Figure 30:
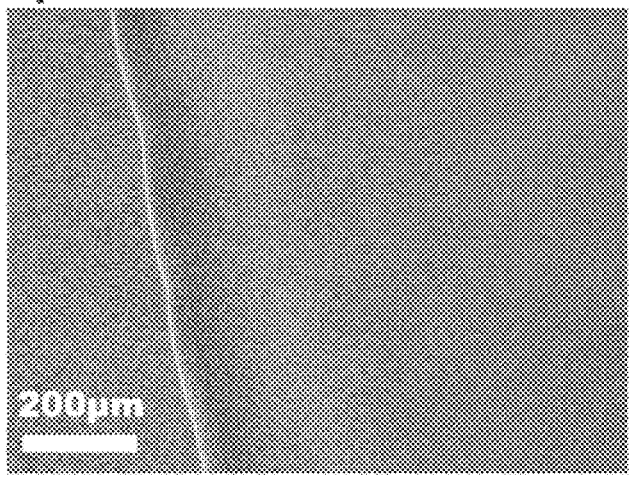
Figure 30:
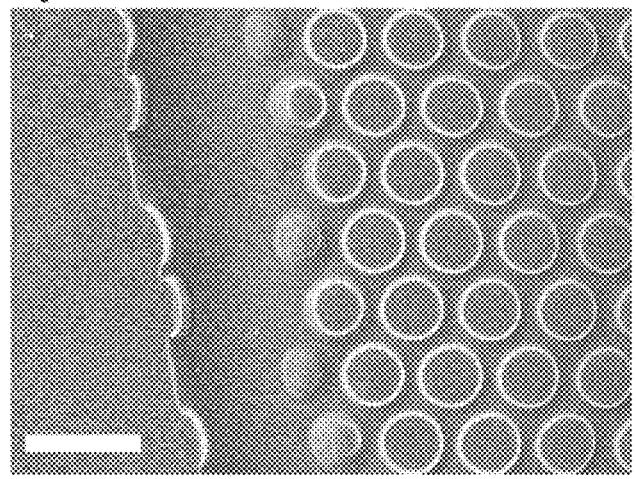
Figure 30:
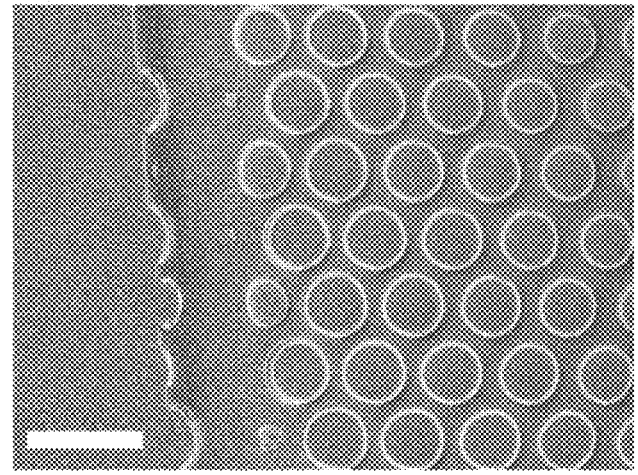

In the respective pH buffer solutions (25° C.) at pH 4.0, pH 5.0, and pH 7.4, a layer coated with pNBANIPAAm at an introduction rate of NBA group of 10 mol % was irradiated with ultraviolet light along a fine polka-dot pattern with a diameter of 100 µm, and light-responsive dissolution properties were observed. The results are shown in FIG. 30. As shown in FIG. 30(a), at pH 4.0, a polymer film was not dissolved even in a case of being irradiated with a sufficient amount of ultraviolet light. As shown in FIG. 30(b) and FIG. 30(c), at pH 5.0 and pH 7.4, the polymer film was rapidly dissolved in response to irradiation with ultraviolet light. The pNBANIPAAm-coated film was kept in an insoluble state for one month in a state of being immersed in a buffer solution at 37° C. and pH 7.4. After that, it was observed that in a case of being irradiated with light, this pNBANIPAAm-coated film was sensitively dissolved.

Figure 31:
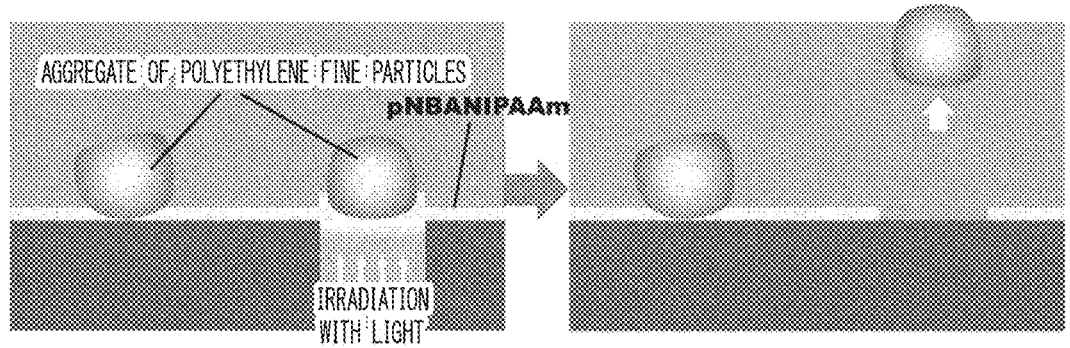
FIG. 31(a) and FIG. 31(b) are a schematic cross-sectional diagram and a bottom image, respectively, showing a light-selective release of fine PE particles which are immobilized on a surface of a PS base material via pNBANIPAAm.
Figure 31:
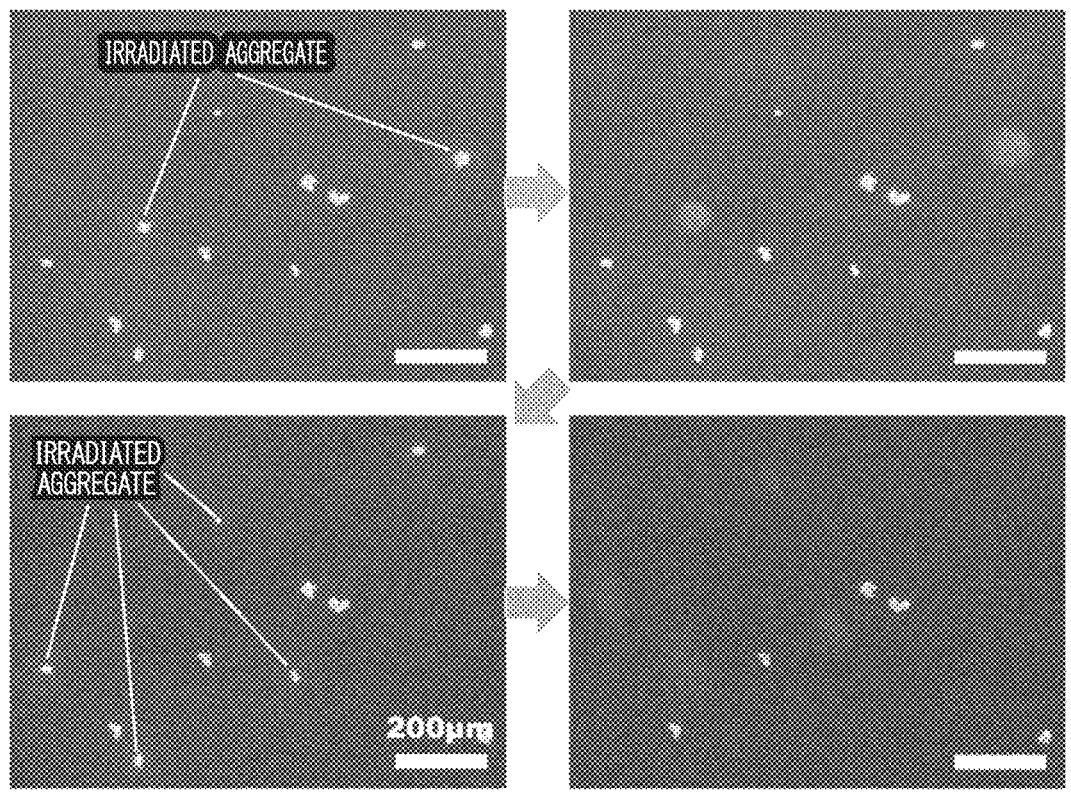

Example 41: Control of Release with Light of Polyethylene Fine Particles Immobilized on pNBANIPAAm A dispersion in which a trace amount of polyethylene fine particles was dispersed in a TFE solution of pNBANIPAAm having an introduction rate of NBA group of 10 mol % was cast on a polystyrene base material. A sample in which the polyethylene fine particles were immobilized on a surface of a polystyrene base material via pNBANIPAAm was obtained. While observing with a microscope, in a phosphate buffer solution at pH 7.4, a region where predetermined fine particle aggregates exist was irradiated with light having a wavelength of 365 nm from a bottom surface of the base material. It was observed that pNBANIPAAm was dissolved and only fine particles which had been irradiated with light floated selectively. The result is shown in FIG. 31. From this result, it was demonstrated that a minute object which cannot be peeled off from a base material by manipulation by hand can be peeled off from the base material by control of light.

Figure 32:
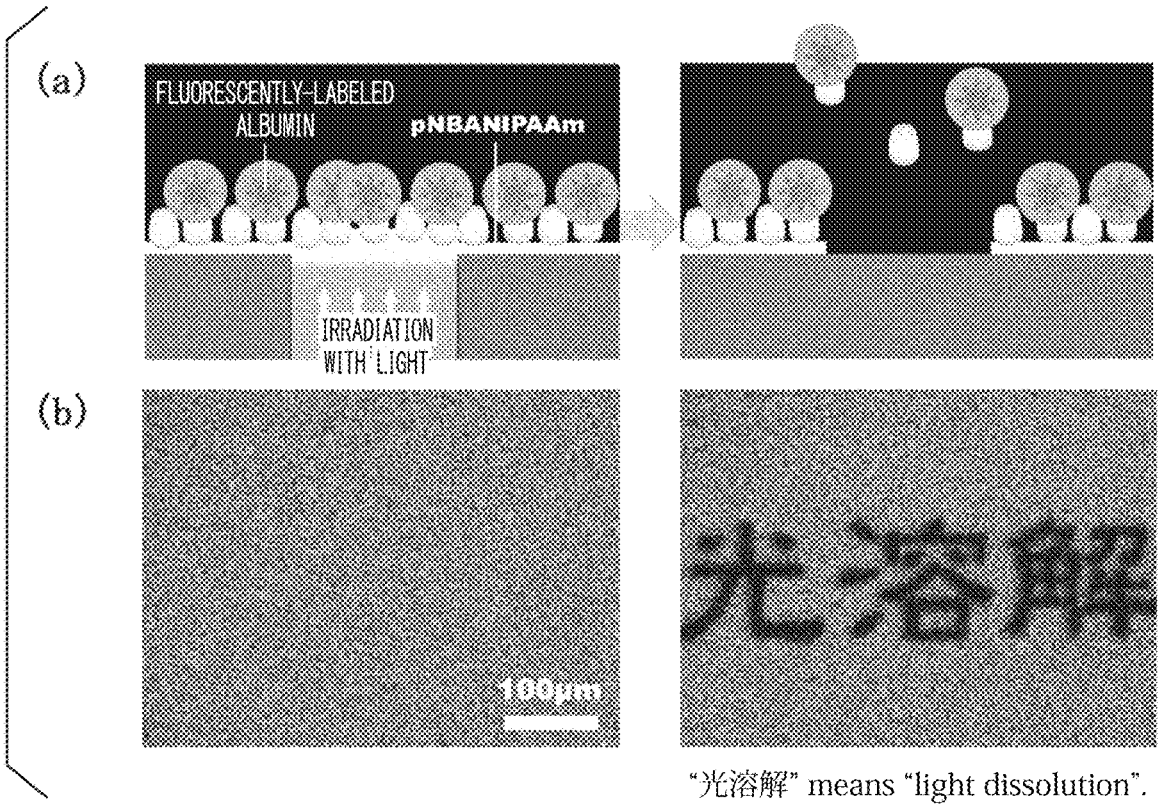
FIG. 32(a) and FIG. 32(b) are a schematic cross-sectional diagram and a bottom image, respectively, showing a light-selective release of fluorescently labeled BSA which is immobilized on a surface of a PS base material via pNBA-NIPAAm.

Example 42: Control of Release with Light of Fluorescently-Labeled Bovine Serum Albumin Immobilized on pNBANIPAAm PNBANIPAAm having an introduction rate of NBA group of 7 mol % was coated on a polystyrene base material. A phosphate buffer solution (pH 7.4) of bovine serum albumin (RBSA) fluorescently-labeled with rhodamine was placed on the pNBANIPAAm film. Then, the resultant was allowed to stand at 37° C. for 30 minutes to obtain a sample in which RBSA was immobilized on a surface of the base material via a thin layer of pNBANIPAAm. The sample was irradiated with light of a minute text pattern from a bottom surface side of the base material, and fluorescence distribution before and after irradiation was observed with a confocal laser scanning microscope. FIG. 32(a) schematically shows how RBSA is released by light. FIG. 32(b) shows fluorescence distribution images before irradiation with light (left) and after irradiation with light (right). As shown in FIG. 32(b), fluorescence disappeared only from an area which had been irradiated with light. That is, RBSA immobilized on the surface of the base material was selectively released from the surface of the base material by local irradiation with light.

Example 43: Patterning of Cultured Cells and Light-Selective Peeling Using NBA Copolymer-Coated Membrane on Cell Adhesion Inhibition Surface A basic methanol solution that contains 0.20% of pNIPAAm containing 5 mol % of methacrylic acid and 0.039% of polyethylene glycol having glycidyl groups at both ends was spin-coated on a surface of a polystyrene base material. Then, heating was carried out at 80° C. for 2 hours to prepare a cell adhesion inhibition surface. A TFE solution that contains 1.3% of NIPAAm containing 10 mol % of NBA group and 20 mol % of NTBAAm and 0.23% of unmodified pNIPAAm was spin-coated on the cell adhesion inhibition surface and heated at 85° C. for 1.5 hours.

Figure 33:
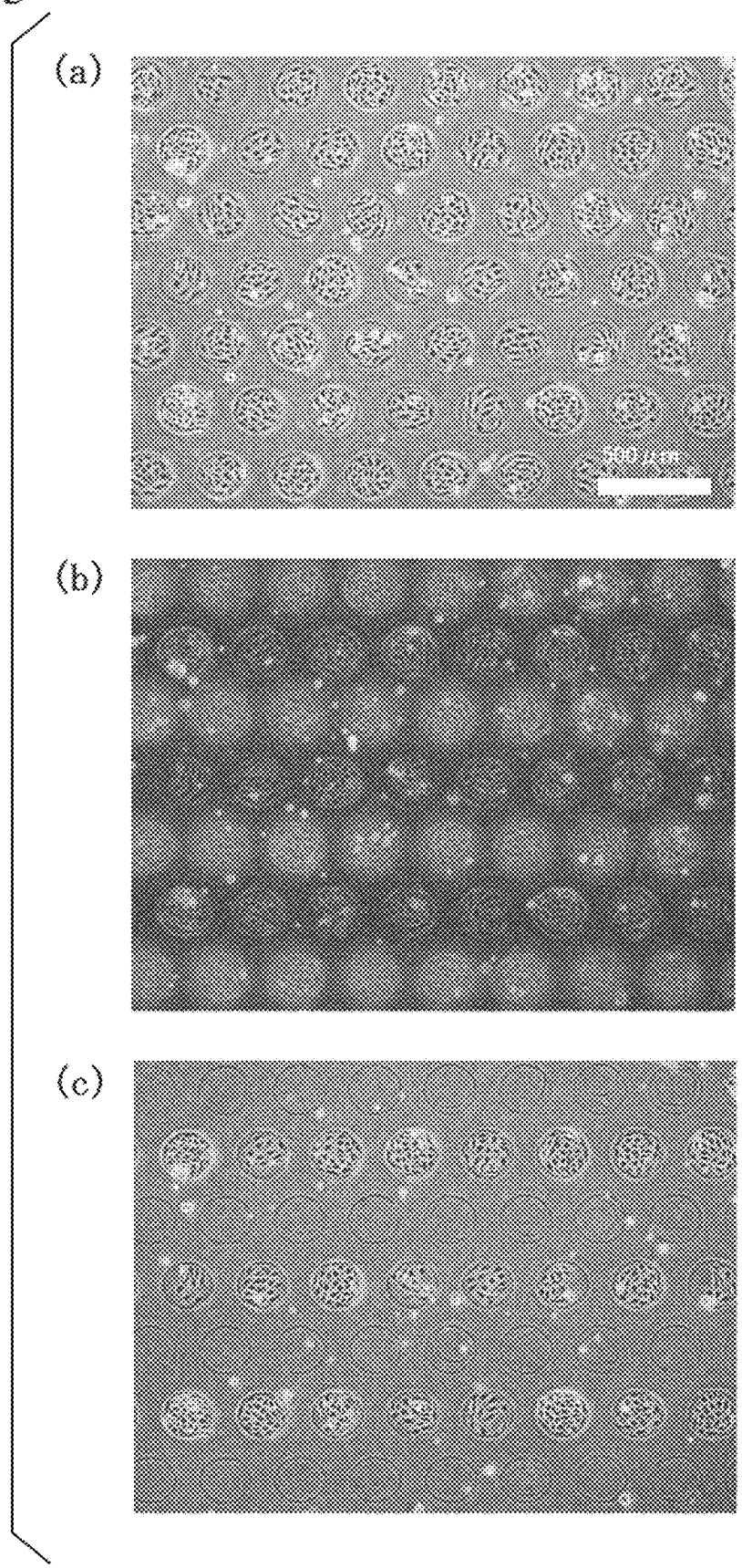

Thereafter, a phosphate buffer solution at pH 7.4 was placed thereon, and light having a wavelength of 365 nm and an intensity of 30 mW/cm$^2$ was irradiated for 6 seconds along an inversion pattern of a dot pattern, so that a blended polymer in an area which had been irradiated with light and a blended polymer layer having a dot-patterned shape was obtained. A dispersion in which MDCK cells were dispersed in a medium was seeded on the blended polymer layer and cultured for half a day. This result is shown in FIG. 33.

As shown in FIG. 33(a), it was confirmed that the cells adhered and spread only on the blended polymer layer having a dot-patterned shape. Then, as shown in FIG. 33(b), about a certain half of the dot regions (laterally striped shape) was irradiated with light having a wavelength of 365 nm and an intensity of 30 mW/cm² for about 40 seconds. Thereafter, in a case where a medium was gently sprayed on the surface, as shown in FIG. 33(c), the cells were selectively peeled off from only a stripe-shaped dot region which had been irradiated with light. From these results, it was demonstrated that due to light manipulation, cell patterning, and selective peeling and recovery of cells can be done therefrom.

Figure 34:
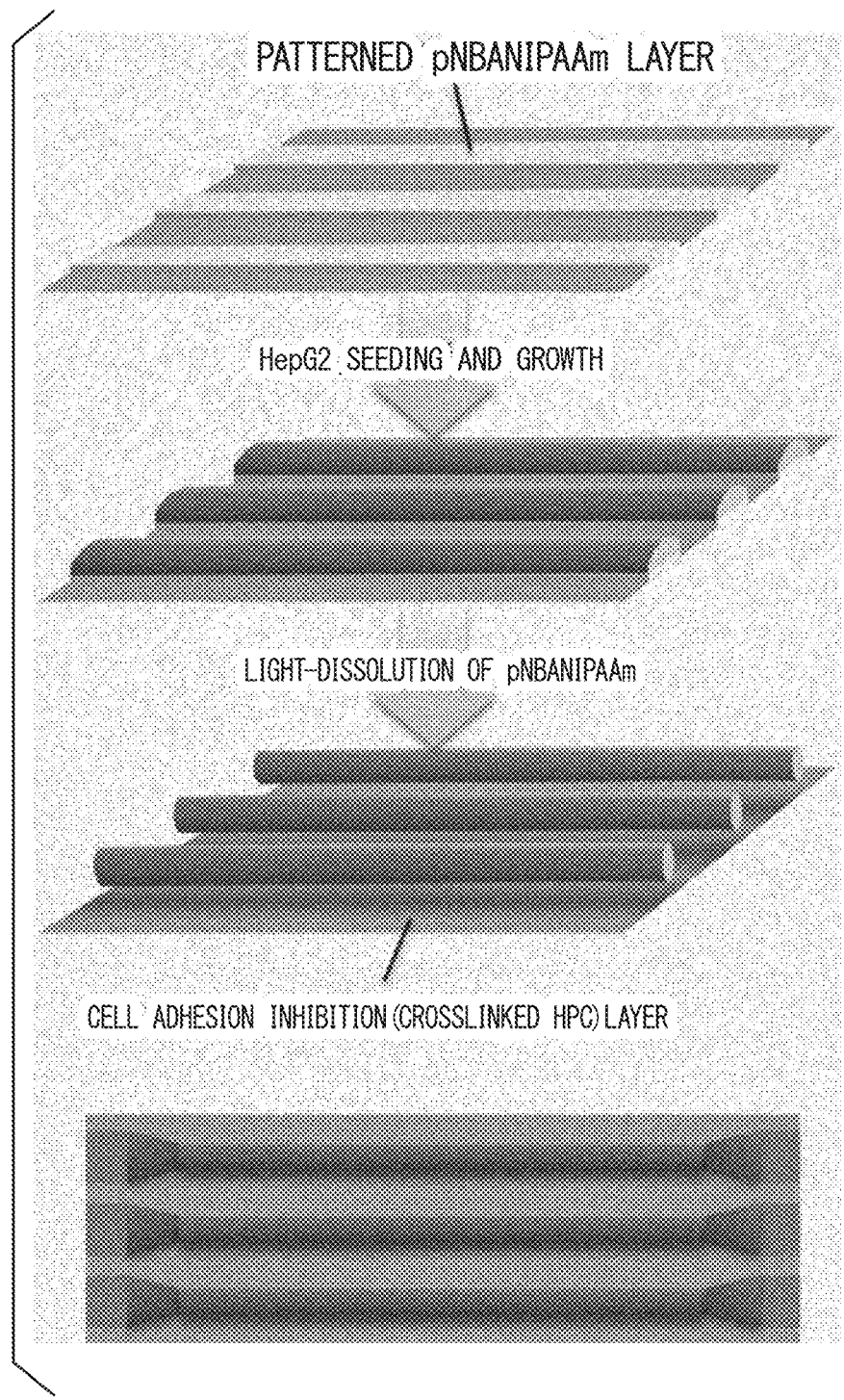
FIG. 34 is a schematic diagram showing a process of forming a string-like cellular organized body using an NBA copolymer.

Example 44: Formation of String-Like Cellular Organized Body Using NBA Copolymer Attempts have been made to evaluate hepatic metabolism and hepatotoxicity of drugs or the like using a culture system of hepatic parenchymal cells or a cell line derived therefrom. However, it is a problem that almost no liver-specific function is developed with ordinary culturing methods. For this reason, culturing as an organized body in which cells are aggregated has been studied as a technique for improving a decrease in function. However, difficulty of supplying oxygen and nutrients to an inside of a cell agglomerate is a problem. Therefore, attempts were made to construct a string-like organized body structure immobilized on a culture substrate by applying optical properties of an NBA-modified polymer, as a structure in which a medium flows through a gap between the organized body and the base material. A process of forming this structure is schematically shown in FIG. 34.

First, an acidic methanol solution containing 0.30% of hydroxypropyl cellulose and 0.042% of polyethylene glycol having carboxyl groups at both ends was spin-coated on a surface of a polystyrene base material. Then, this was heated at 85° C. for 3 hours to prepare a cell adhesion inhibition surface. Thereafter, a 1.6% TFE solution of pNIPAAm containing 15 mol % of NBA group and 20 mol % of NTBAAm was spin-coated on the cell adhesion inhibition surface. This was heated at 85° C. for 1 hour and then coated with fibronectin.

Figure 35:
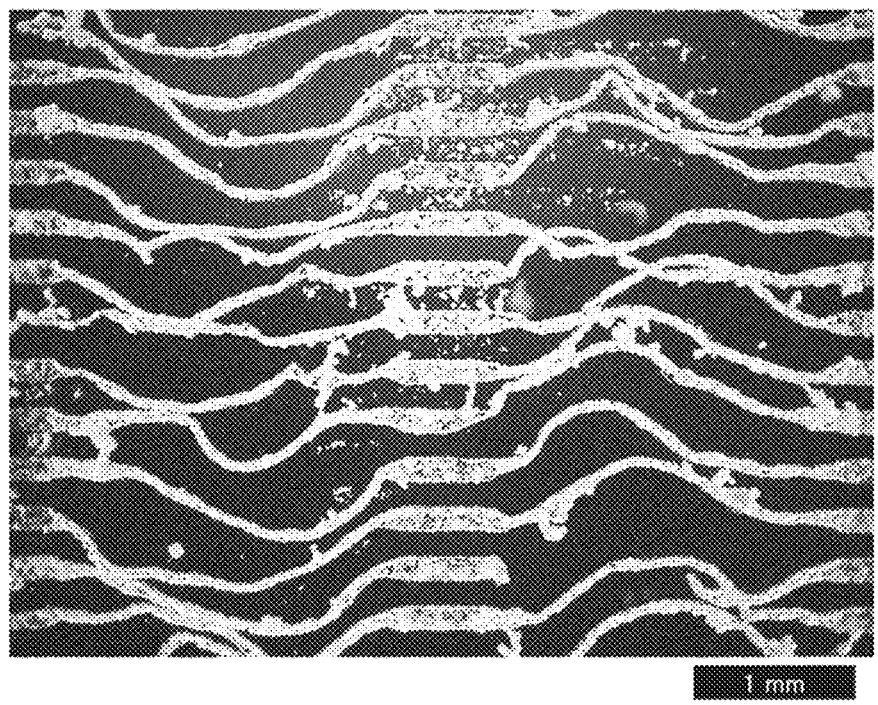
FIG. 35 is an image of a string-like organized body formed of HepG2 cells which are partially immobilized on a surface of a base material.

The fibronectin coat was irradiated with light in a stripe-shaped pattern in a phosphate buffer solution at pH 7.4, and a light-responsive polymer layer was dissolved and removed from an area which had been irradiated with light. HepG2 cells, which are a cell line derived from human hepatic parenchymal cells, were seeded thereon and adhered in a pattern on the light-responsive polymer layer remaining in the stripe shape. After culturing for 2 days, it was confirmed that a string-like organized body floating from the base material could be formed by causing a part of the light-responsive polymer layer to which HepG2 cells adhered to be left by local irradiation with light and to be peeled off from a surface of the base material. This image is shown in FIG. 35.

Figure 36:
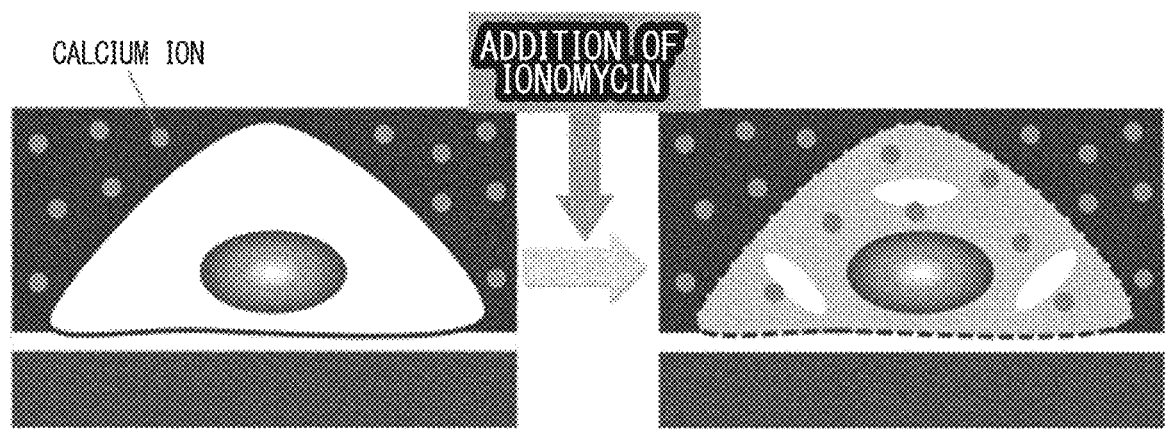
FIG. 36 is a schematic diagram for describing an action of ionomycin on cultured cells.

Example 45: Light-Responsive Ionomycin Supply from Culture Substrate Using NBA Copolymer In a cell culture system, calcium ions are contained in a medium at a concentration of the order of mM. However, due to work of a calcium ion pump present in a cell membrane, calcium ions are kept at a very low concentration of the order of nM in cells of the cell culture system. In a case where ionomycin is added to the cells of the cell culture system, ionomycin is taken into cell membranes and induces calcium permeation in the cell membranes. In a case where the calcium permeation in the cell membrane is remarkable, cell death is caused. This mechanism is schematically shown in FIG. 36.

Figure 37:
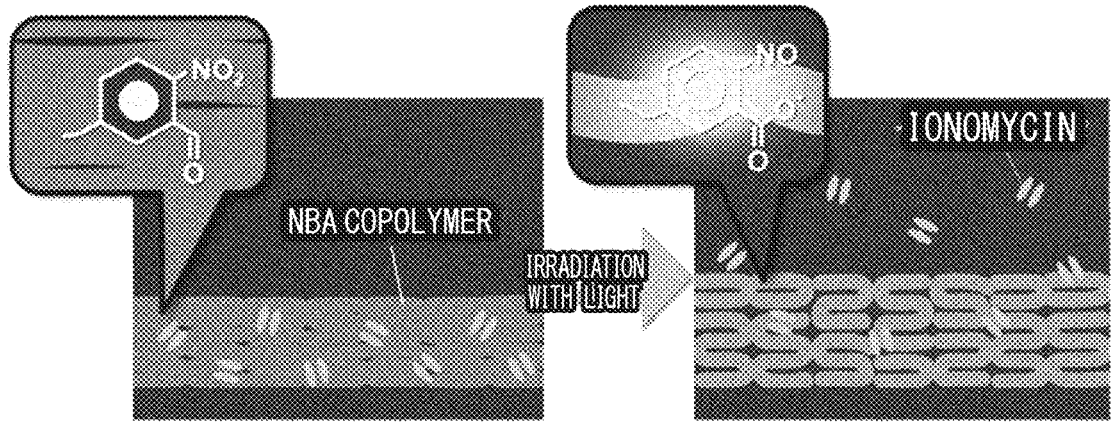
FIG. 37(a) is a schematic diagram for describing immobilization of ionomycin by an NBA copolymer and release with light.
FIG. 37(b) is an image of local cell death caused by pattern irradiation onto NIH/3T3 cells.
Figure 37:
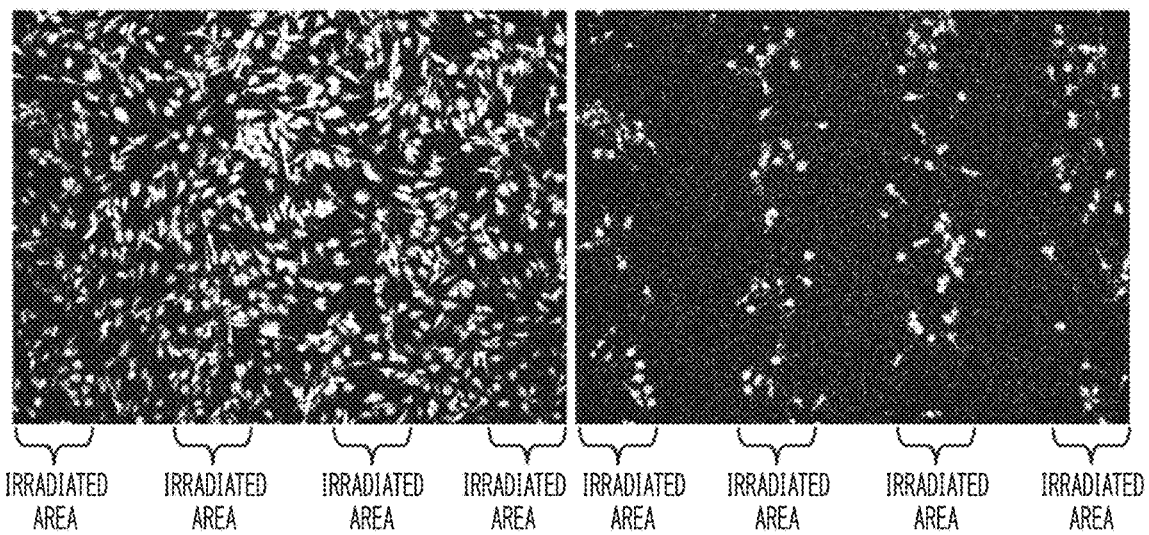

As an example of a technology for controlling light emission of a compound having a physiological activity, a base material capable of stably immobilizing ionomycin and capable of being supplied to a predetermined place at a predetermined timing was prepared. A TFE solution that contains PNIPAAm containing 10 mol % of NBA group and 50 mol % of NTBAAm, and ionomycin was spin-coated on a surface of a polystyrene base material. NIH/3T3 cells were seeded thereon and cultured for half a day. Thereafter, in a case where ultraviolet light having a wavelength of 365 nm was locally irradiated in a common medium, cell death was caused only in the irradiated area. A mechanism for immobilization of ionomycin and release with light is schematically shown in FIG. 37(a). In addition, an image showing this local cell death is shown in FIG. 37(b).

On the other hand, in a case where the common medium was replaced with a medium not containing calcium ions before irradiation with light, cell death was not induced. This result shows that the cell death caused by irradiation with light is due to inflow of calcium ions into cells led by ionomycin. In addition, in a case of using a polymer with an NTBAAm content of 20 mol %, retention of ionomycin of a polymer was insufficient. For this reason, even in a dark place, it was observed that ionomycin was released from the polymer into a culture system and cells were damaged as a whole. Furthermore, in a case of using a polymer in which a monomer other than a monomer component of NBA group was NTBAAm, ionomycin was not released even by irradiation with light and cell damage was not induced.

The invention claimed is:
1. A polymer compound, comprising:
a main chain; and
a side chain,
wherein the side chain contains an aromatic ring,
the aromatic ring contains a first carbon atom in which a hydrogen atom bonded thereto is substituted with a nitro group and a second carbon atom in which a hydrogen atom bonded thereto is substituted with an aldehyde group or a functional group represented by Formula (1), and
the first carbon atom and the second carbon atom are adjacent in the same benzene ring

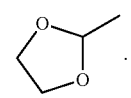

(1)

2. The polymer compound according to claim 1, which is represented by Formula (2),

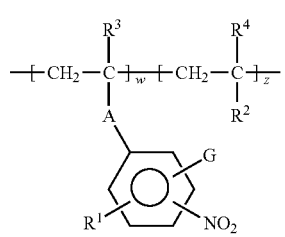

(2)

where A is a single bond or a functional group,
R¹ is an aldehyde group or a functional group represented by Formula (1),
R¹ and NO₂ are bonded to adjacent carbon atoms,
R² is at least one member selected from hydrogen, an alkyl group, a functional group represented by Formula (3), and a functional group represented by Formula (4)

($R^6$ and $R^7$ are hydrogen, an alkyl group, or an aromatic ring, and $R^8$ is an alkyl group), $$O=C-N(R^6)(R^7) \quad (3)$$

$$O=C-O-R^8 \quad (4)$$

$R^3$ and $R^4$ are hydrogen or an alkyl group,

G is 3 or less alkyl groups with which hydrogen in the benzene ring may be substituted, and w and z represent molar percentages, in which $0<w\leq100$ and $0\leq z<100$.

3. A polymer compound represented by Formula (5), $$\text{---}[CH_2\text{---}C(R^3)(A)]_x\text{---}[CH_2\text{---}C(R^9)(B)]_y\text{---}[CH_2\text{---}C(R^4)(C(=O)N(R^6)(R^7))]_z\text{---} \quad (5)$$

(with A bearing a phenyl substituted by O=CH and $NO_2$; B bearing a phenyl substituted by 1,3-dioxolane and $NO_2$)

where A and B are a single bond or a functional group, $R^3$, $R^4$, and $R^9$ are hydrogen or an alkyl group, $R^6$ and $R^7$ are hydrogen, an alkyl group, or an aromatic ring, and x, y, and z represent molar percentages, in which $0\leq x<100$, $0\leq y<100$, and $0\leq z<100$ (where x=y=0 is excluded).

4. A composite material, comprising:

a base material; and a layer containing the polymer compound according to claim 1 provided on a surface of the base material.

5. A light-driven actuator, comprising:

a light source; and the composite material according to claim 4.

6. A method for manipulating a cell, comprising:

a culturing step of culturing cells on a surface of the layer containing the polymer compound in the composite material according to claim 4;

a light-irradiating step of causing at least a part of a region of the surface of the layer containing the polymer compound to be irradiated with light, after the culturing step; and a removing step of removing cells that exist in the region which has been irradiated with light in the light-irradiating step.

7. The method for manipulating a cell according to claim 6, wherein in the removing step, a portion of the layer containing the polymer compound is dissolved in water and a portion of the cultured cells is removed.

8. A compound represented by Formula (6)

(6) (methacrylate ester of phenol bearing a 1,3-dioxolane substituent and $NO_2$)

9. A compound represented by Formula (7)

(7) (methacrylamide with propyl linker to phenoxy bearing 1,3-dioxolane and $NO_2$)

* * * * *